US008569273B2

(12) United States Patent
Abelson et al.

(10) Patent No.: US 8,569,273 B2
(45) Date of Patent: Oct. 29, 2013

(54) OPHTHALMIC FORMULATIONS OF CETIRIZINE AND METHODS OF USE

(75) Inventors: Mark Barry Abelson, Andover, MA (US); Matthew J. Chapin, Amesbury, MA (US); Paul Gomes, Haverhill, MA (US); George Minno, Windham, NH (US); Jackie Nice, Medford, MA (US)

(73) Assignee: Aciex Therapeutics, Inc., Boston, MA (US)

( * ) Notice: Subject to any disclaimer, the term of this patent is extended or adjusted under 35 U.S.C. 154(b) by 0 days.

(21) Appl. No.: 12/888,117

(22) Filed: Sep. 22, 2010

(65) Prior Publication Data

US 2011/0257136 A1 Oct. 20, 2011

Related U.S. Application Data

(63) Continuation-in-part of application No. 12/724,128, filed on Mar. 15, 2010.

(60) Provisional application No. 61/161,006, filed on Mar. 17, 2009, provisional application No. 61/174,850, filed on May 1, 2009.

(51) Int. Cl.
*A61K 31/56* (2006.01)
*A61P 27/14* (2006.01)

(52) U.S. Cl.
USPC ............................................................. 514/171

(58) Field of Classification Search
None
See application file for complete search history.

(56) References Cited

U.S. PATENT DOCUMENTS

| | | | |
|---|---|---|---|
| 4,407,791 A | 10/1983 | Stark | |
| 4,525,358 A | 6/1985 | Baltes et al. | |
| 5,188,826 A * | 2/1993 | Chandrasekaran et al. | 424/78.04 |
| 5,419,898 A * | 5/1995 | Ikejiri et al. | 424/78.04 |
| 5,698,558 A | 12/1997 | Gray | |
| 6,103,735 A | 8/2000 | Aslanian et al. | |
| 6,436,924 B2 | 8/2002 | Poppe et al. | |
| 6,649,602 B1 | 11/2003 | Yanni | |
| 6,827,946 B2 | 12/2004 | Hirsh | |
| 2002/0037297 A1 | 3/2002 | Crespo et al. | |
| 2004/0198743 A1 | 10/2004 | Hey et al. | |
| 2004/0198828 A1 | 10/2004 | Abelson et al. | |
| 2005/0239745 A1 | 10/2005 | Abelson et al. | |
| 2006/0025391 A1 * | 2/2006 | Lulla et al. | 514/171 |
| 2006/0183698 A1 | 8/2006 | Abelson | |
| 2006/0216353 A1 | 9/2006 | Liversidge et al. | |
| 2006/0228306 A1 | 10/2006 | Lane | |
| 2007/0020330 A1 | 1/2007 | Dang et al. | |
| 2007/0275974 A1 | 11/2007 | Fanara et al. | |
| 2008/0085922 A1 | 4/2008 | Raja et al. | |
| 2008/0254029 A1 | 10/2008 | Yanni et al. | |

FOREIGN PATENT DOCUMENTS

| | | |
|---|---|---|
| EP | 0433766 A1 | 6/1991 |
| EP | 0920315 B1 | 6/1999 |
| RU | 2220740 C1 | 1/2004 |
| WO | WO-9746243 A1 | 12/1997 |
| WO | WO-9806394 A1 | 2/1998 |
| WO | WO-9915203 A1 | 4/1999 |
| WO | WO-03049770 A1 | 6/2003 |
| WO | WO-2004066960 A2 | 8/2004 |
| WO | WO-2004069338 A1 | 8/2004 |
| WO | WO-2005030331 A1 | 4/2005 |
| WO | WO-2005107711 A2 | 11/2005 |
| WO | WO-2006102494 A2 | 9/2006 |
| WO | WO-2007117971 A2 | 10/2007 |

OTHER PUBLICATIONS

Goodman and Gilman's The Pharmacological Basis of Therapeutics (Tenth Edition (2001), McGraw Hill, Chapter I, pp. 3-29.*
"United States Pharmacopeia" (http://en.wikipedia.org/wiki/United_States_Pharmacopeia#_Product_quality.E2.80.93standards_and_verification) accessed from the internet on Oct. 22, 2012.*
Abelson et al., "A Randomized, Double-Blind, Parallel-Group Comparison of Olopatadine 0.1% Ophthalmic Solution Versus Placebo for Controlling the Signs and Symptoms of Seasonal Allergic Conjunctivitis and Rhinoconjunctivitis", *Clinical Therapeutics*, 25(3):931-947 (2003).
Berger et al., "Effects of adjuvant therapy with 0.1% olopatadine hydrochloride ophthalmic solution on quality of life in patients with allergic rhinitis using systemic or nasal therapy", *Ann. Allergy Asthma Immunol.*, 95(4):361-371 (2005).
Crampton et al., "A Comparison of the Relative Clinical Efficacy of a Single Dose of Ketotifen Fumarate 0/025% Ophthalmic Solution Versus Placebo in Inhibiting the Signs and Symptoms of Allergic Rhinoconjunctivitis as Induced by the Conjunctival Allergen Challenge Model", *Clinical Therapeutics*, 24(11):1800-1808 (2002).
Lanier et al., Comparison of the Efficacy of Combined Fluticasone Propionate and Olopatadine Versus Combined Fluticasone Propionate and Fexofenadine for the treatment of Allergic Rhinoconjunctivitis Induced by Conjunctival Allergen Challenge, *Clin. Ther.*, 24(7):1161-1174 (2002).
Ousler et al., "An evaluation of the ocular drying effects of 2 systemic antihistamines: loratadine and cetirizine hydrochloride", *Ann. Allergy Asthma Immunol.*, 93(5):460-464 (2004).
Spangler et al., "Randomized, Double-Masked Comparison of Olopatadine Ophthalmic Solution, Mometasone Furoate Monohydrate Nasal Spray, and Fexofenadine Hydrochloride Tablets Using the Conjunctival and Nasal Allergen Challenge Models", *Clin. Ther.*, 25(8):2245-2267 (2003).

* cited by examiner

*Primary Examiner* — Dennis Heyer
(74) *Attorney, Agent, or Firm* — Mintz Levin Cohn Ferris Glovsky and Popeo, P.C.; Ivor R. Elrifi; Cynthia A. Kozakiewicz

(57) ABSTRACT

The present invention provides stable topical formulations of cetirizine that provide a comfortable formulation when instilled in the eye and is effective in the treatment of allergic conjunctivitis and/or allergic conjunctivitis. The invention further provides methods of treating allergic conjunctivitis rhinitis, and/or allergic rhinoconjunctivitis in a subject in need of such treatment by topical application of the cetirizine formulations of the invention directly to the eye.

14 Claims, 46 Drawing Sheets

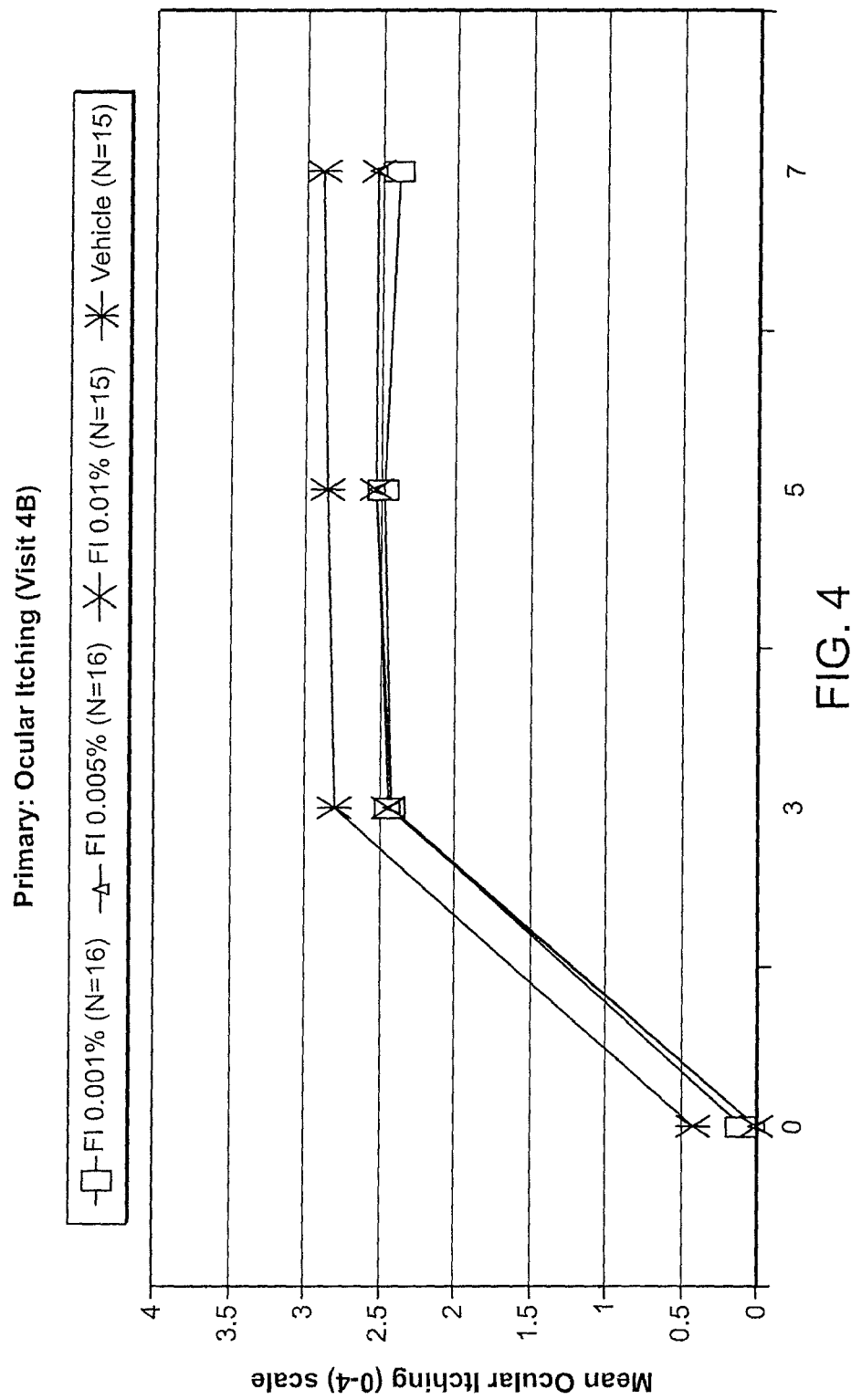

SAFETY-ADVERSE EVENTS

- Fluticasone 0.001%- 1 Event- 6.3% of Subjects
  – Vision blurred

- Fluticasone 0.005%- 2 Events- 12.5% of Subjects
  – Conjunctival hemorrhage
  – Dry eye

- Fluticasone 0.01%- 5 Events- 18.8% of Subjects
  – 3 Instillation site pain
  – 1 Instillation site irritation
  – 1 Headache

- Vehicle- 1 Event- 6.3% of Subjects
  – 1 Gastroenteritis Viral

FIG. 22

Visit 3: 15 Minute Onset

| Treatment | 3 | 5 | 7 |
|---|---|---|---|
| Combo (N=18) | -1.74* | -1.83* | -1.79* |
| Pataday[1] | -1.30* | -1.50* | -1.40* |
| Alcaftadine | -1.50* | -1.49* | -1.47* |

Red: Clinically significant differences
*: P<0.05 Combo vs vehicle

1 CAC 27 minutes onset

Visit 4A- 16 Hour Duration

| Treatment | 3 | 5 | 7 |
|---|---|---|---|
| Combo (N=18) | -1.43* | -1.35* | -1.30* |
| Pataday | -0.90 | -1.00* | -0.87 |
| Alcaftadine | -1.73 | -1.49 | -1.58 |

Combo better than Pataday at onset and duration
Combo better than Alcaftadine at onset

FIG. 35

Visit 3: 15 Minute Onset

| Treatment | 0 | 3 | 5 | 7 |
|---|---|---|---|---|
| Combo (N=18) | -0.08 | -1.74* | -1.83* | -1.79* |
| Cetirizine (N=17) | +0.09 | -1.93 | -1.81 | -1.43 |
| Fluticasone (N=17) | -0.03 | -0.69 | -0.77 | -0.85 |

Visit 4A - 16 Hour Duration

| Treatment | 0 | 3 | 5 | 7 |
|---|---|---|---|---|
| Combo (N=18) | -0.39* | -1.43* | -1.35* | -1.30* |
| Cetirizine (N=17) | -0.12 | -1.08 | -0.90 | -1.02 |
| Fluticasone (N=17) | -0.33 | -1.14 | -0.94 | -1.09 |

Visit 4B - 8 Hour Rechallenge

| Treatment | 0 | 3 | 5 | 7 |
|---|---|---|---|---|
| Combo (N=18) | -0.23ᵗ | -1.77* | -1.47* | -1.21* |
| Cetirizine (N=17) | +0.03 | -1.49 | -1.06 | -0.90 |
| Fluticasone (N=17) | -0.19 | -0.95 | -0.69 | -0.76 |

Red: Clinically significant differences
\*: P<0.05 Combo vs vehicle

FIG. 40

Visit 3: 15 Minute Onset

| Treatment | 0 | 7 | 15 | 20 |
|---|---|---|---|---|
| Combo (N=18) | -0.15 | -0.85* | -0.65* | -0.65* |
| Cetirizine (N=17) | +0.09 | -0.41 | -0.24 | -0.12 |
| Fluticasone (N=17) | -0.05 | -0.22 | -0.12 | -0.09 |

Visit 4A - 16 Hour Duration

| Treatment | 0 | 7 | 15 | 20 |
|---|---|---|---|---|
| Combo (N=18) | -0.18 | -0.50* | -0.54* | -0.43* |
| Cetirizine (N=17) | -0.08 | -0.18 | -0.25 | -0.06 |
| Fluticasone (N=17) | -0.11 | -0.19 | -0.21 | -0.24 |

Visit 4B - 8 Hour Rechallenge

| Treatment | 0 | 7 | 15 | 20 |
|---|---|---|---|---|
| Combo (N=18) | -0.53* | -0.63* | -0.74* | -0.78* |
| Cetirizine (N=17) | -0.23 | -0.22 | -0.37 | -0.35 |
| Fluticasone (N=17) | -0.35 | -0.16 | -0.31 | -0.34 |

*: P<0.05 Combo vs vehicle

FIG. 41

Visit 3: 15 Minute Onset

| Treatment | 0 | 3 | 5 | 7 |
|---|---|---|---|---|
| Cetirizine (N=17) | -0.17 | +0.19 | -0.02 | -0.36 |
| Fluticasone (N=17) | -0.05 | -1.05* | -1.06* | -0.94* |

Visit 4A - 16 Hour Duration

| Treatment | 0 | 3 | 5 | 7 |
|---|---|---|---|---|
| Cetirizine (N=17) | -0.27 | -0.35 | -0.45 | -0.28 |
| Fluticasone (N=17) | -0.06 | -0.29 | -0.41 | -0.21 |

Visit 4B - 8 Hour Rechallenge

| Treatment | 0 | 3 | 5 | 7 |
|---|---|---|---|---|
| Cetirizine (N=17) | -0.26 | -0.28 | -0.41 | -0.31 |
| Fluticasone (N=17) | -0.04 | -0.82* | -0.78* | -0.45 |

*: $P<0.05$ Combo vs individual component
t: $P=0.0605$

FIG. 42

Visit 3: 15 Minute Onset

| Treatment | 0 | 7 | 15 | 20 |
|---|---|---|---|---|
| Cetirizine (N=17) | -0.24 | -0.44$^t$ | -0.41 | -0.53$^t$ |
| Fluticasone (N=17) | -0.10 | -0.63* | -0.53* | -0.56$^t$ |

Visit 4A - 16 Hour Duration

| Treatment | 0 | 7 | 15 | 20 |
|---|---|---|---|---|
| Cetirizine (N=17) | -0.10 | -0.32* | -0.29$^t$ | -0.37* |
| Fluticasone (N=17) | -0.07 | -0.31$^t$ | -0.33$^t$ | -0.19 |

Visit 4B- 8 Hour Rechallenge

| Treatment | 0 | 7 | 15 | 20 |
|---|---|---|---|---|
| Cetirizine (N=17) | -0.30$^t$ | -0.41* | -0.47* | -0.43* |
| Fluticasone (N=17) | -0.18 | -0.47* | -0.53* | -0.44* |

\*: $P<0.05$ Combo vs individual component
t: $0.05<P<0.10$

FIG. 43

Visit 3: 15 Minute Onset

| Treatment | 0 | 7 | 15 | 20 |
|---|---|---|---|---|
| Combo (N=18) | -0.12 | -0.93* | -0.65* | -0.62$^t$ |
| Cetirizine (N=17) | +0.08 | -0.53 | -0.29 | -0.27 |
| Fluticasone (N=17) | +0.08 | -0.02 | -0.07 | -0.04 |

Visit 4A - 16 Hour Duration

| Treatment | 0 | 7 | 15 | 20 |
|---|---|---|---|---|
| Combo (N=18) | -0.23 | -0.65* | -0.59* | -0.51* |
| Cetirizine (N=17) | -0.04 | -0.22 | -0.20 | -0.13 |
| Fluticasone (N=17) | -0.16 | -0.32 | -0.26 | -0.32 |

Visit 4B- 8 Hour Rechallenge

| Treatment | 0 | 7 | 15 | 20 |
|---|---|---|---|---|
| Combo (N=18) | -0.40* | -0.97* | -1.10* | -0.95* |
| Cetirizine (N=17) | -0.18 | -0.36 | -0.49 | -0.47 |
| Fluticasone (N=17) | -0.44 | -0.33 | -0.44 | -0.42 |

Red: Clinically significant differences
*: P<0.05 Combo vs vehicle

FIG. 44

OPHTHALMIC FORMULATIONS OF CETIRIZINE AND METHODS OF USE

REFERENCE TO RELATED APPLICATIONS

This application is a continuation in part of U.S. Ser. No. 12/724,128, filed Mar. 15, 2010 and claims priority to U.S. Provisional Application No. 61/161,006, filed Mar. 17, 2009 and U.S. Provisional Application No. 61/174,850, filed May 1, 2009, the contents of which are each hereby incorporated by reference in their entireties.

FIELD OF THE INVENTION

The invention relates to compositions comprising cetirizine, alone or in combination with one or more additional active agents such as a steroid and/or a vasoconstrictor, and methods for using the same for treating allergic conjunctivitis, rhinitis and/or allergic rhinoconjunctivitis.

BACKGROUND OF THE INVENTION

There exists a need for topical ophthalmic pharmaceutical products to effectively treat allergic conjunctivitis, rhinitis and/or allergic rhinoconjunctivitis, disorders that presents with both acute allergic signs and symptoms (i.e., intermittent seasonal or perennial allergy) and late phase inflammatory reactions (i.e., chronic, refractory or persistent allergy). It has been estimated that 46% (~70 million) of the adult allergy patients in the United States suffer from both the acute and late phase conditions of allergic conjunctivitis, whereas only 19% suffer from only acute or late phase allergy, respectively. It is estimated that allergic rhinoconjunctivitis (a combination of ocular and nasal symptoms) may occur in up to 90% of patients with allergies. The average age of allergy sufferers—between 20 and 40 years—coincides with the average age of the work force and the most productive period of an individual's life.

Both seasonal and perennial allergic conjunctivitis (ocular allergies) are characterized by ocular itching, redness, lid swelling, chemosis (swelling of the conjunctiva), and tearing. Rhinitis (nasal allergies) manifests as a runny nose (rhinorrhea), sneezing, nasal congestion, nasal itching, and itching of the palate and/or ear. It can be difficult for a physician to distinguish allergic conjunctivitis from the ocular component of allergic rhinoconjunctivitis because both allergic reactions can occur simultaneously or be triggered by the same types of stimuli. It is further difficult to distinguish acute allergic symptoms from late phase symptoms of allergic conjunctivitis, as each of these conditions can persist simultaneously or morph back and forth in any given individual. The signs and symptoms of allergic conjunctivitis, rhinitis, and allergic rhinoconjunctivitis can significantly impact the quality of life of patients, from social interactions, productivity at work and school, to the ability to perform visual tasks such as working on a computer or reading.

Acute symptoms of allergic conjunctivitis are characterized by the clinical signs and symptoms of eye itching, redness, tearing, and swelling. Late phase or allergic inflammation reactions of allergic conjunctivitis include redness, lid swelling and tearing, and in some cases itching, as well as the predominance of congestion in the nose. Acute allergic symptoms are predominantly caused by the activation of mast cells, which when stimulated by an allergen (pollen, dust, dander) releases a host of substances that produce the signs and symptoms of allergic conjunctivitis (itching, redness, swelling, and tearing). Histamine is the primary mediator released and stimulates receptors on nerve endings and blood vessels to produce itching and redness. There are two histamine receptors that have been identified on the ocular surface. H1 receptors on nerve endings lead to itching, and H1 and H2 receptors on blood vessels lead to dilation of the blood vessels, leading to redness, and leakage of fluid from the vessels into the surrounding tissue producing swelling. Late phase inflammatory reactions are mediated by activation of inflammatory cells.

Like allergic conjunctivitis, allergic rhinitis and rhinoconjunctivitis is an allergen-induced, mast cell-mediated response. The reaction is triggered when airborne allergens bind to antibodies attached to the surface of mast cells in the eye and/or nose. Mast cells, in turn, release chemical mediators, which account for the immediate reaction in sensitized individuals exposed to allergen. Some of these mediators, such as histamine, directly affect blood vessels and nerves, leading to the signs and symptoms of allergic disease. Other released mediators cause the influx of white blood cells to the site, which leads to sustained symptoms in severe cases and particularly congestion in the nose.

Allergic conjunctivitis, rhinitis, and rhinoconjunctivitis may also co-exist with other external ocular conditions and diseases, such as dry eye, urban allergy, or irritations caused by pollutants or other causes. This leads to a compromised tear film, which serves to protect the ocular surface from allergens.

Currently available treatments for eye allergy include: drops which can wash allergens off the ocular surface and act as a barrier for the eye (e.g. artificial tears), drugs which block histamine from binding to the histamine receptors (e.g. antihistamines), drugs that block the release of histamine and other substances from the mast cell (e.g. mast cell stabilizers), drugs with multiple modes of action (e.g. antihistamine/mast cell stabilizing agents), corticosteroids, and drugs that can actively constrict blood vessels thus reducing redness and swelling (e.g. vasoconstrictors). The criteria which may be considered in evaluating the appropriateness of an agent for a patient include: efficacy at onset of action, duration of action, how well it controls the individual signs and symptoms of allergic conjunctivitis, comfort of the formulation when instilled in the eye, and safety of the formulation when instilled in the eye. The comfort of an ophthalmic product depends on the active pharmaceutical ingredient itself, as well as the nature of the formulation and the vehicle that makes up the product. Oral antihistamines have been shown to induce decreased tear production and lead to dryness of the ocular surface, which can exacerbate ocular discomfort and can make the eye susceptible to irritation by an ophthalmic product.

The currently available treatments which contain a single active agent, such as an antihistamine or a mast cell stabilizer, typically provide relief for only acute allergic conjunctivitis and don't address the signs and symptoms of the late phase inflammatory reactions (i.e., chronic, refractory, or persistent allergy).

Currently available treatments for rhinitis and allergic rhinoconjunctivitis include eyedrops (for the ocular component), nasal sprays, and systemic oral agents. Currently approved anti-allergy eyedrops are indicated for ocular allergy and nasal sprays are targeted for nasal allergy. Systemic agents, while they are marketed to treat both nasal and ocular symptoms, several well controlled clinical trials conducted to ophthalmic standards have shown that systemic antihistamines are inferior to eyedrops in treating the ocular signs and symptoms (Spangler et al., Clin. Ther. 25(8), 2245-2267 (2003), are not in fact clinically effective on eye allergy to the level acceptable by the ophthalmic division at the FDA, and actually have been shown by objective measures to reduce tear production on the eye by 50%, causing ocular dryness (Ousler et al, Ann Allergy Asthma Immunol. November; 93(5):460-4 (2004)). Further studies have shown that the concomitant use of an eyedrop and nasal steroid is more effective than a systemic agent in treating the combined ocular and nasal signs and symptoms of allergy (i.e. due to topical ocular therapy being superior than systemic therapy in treating ocular signs and symptoms) (Lanier et al. Clin. Ther. 24(7), 1161-1174 (2002)).

Cetirizine hydrochloride is a racemic selective H1 receptor inverse agonist which functions as an antihistamine. It is a major metabolite of hydroxyzine and a derivative of piperazine. The levorotary enantiomer of cetirizine is known as levocetirizine. Cetirizine hydrochloride is FDA approved for oral use and is used as a systemic antihistamine for the treatment of allergies, hay fever, angioedema, and urticaria. It has been historically difficult to prepare cetirizine as an ophthalmic solution with satisfactory safety and stability profiles. Cetirizine has the disadvantage of forming aggregates in solution at low concentrations (typically less than 1% (w/v)), thereby decreasing the stability as an aqueous solution. Moreover, higher concentrations of cetirizine (1% and above) are strongly irritating and thus unsuitable for direct ocular or nasal administration. U.S. Pat. No. 5,419,898 addresses these issues by using a cyclodextrin compound to increase the solubility and stability of cetirizine for ophthalmic use. However, a cyclodextrin-free stable ophthalmic formulation containing cetirizine as the only active ingredient that is both comfortable in the eye and effective to mitigate the symptoms of allergic conjunctivitis has never been previously achieved. Further it is desired to if possible avoid the need for using a cyclobetadextran (CBD) as no current ophthalmic products use CBD, there exists potential stability problems over time, and pharmacokinetics may be impacted due to interaction of the active ingredient with the CBD.

There thus exists a need to develop an effective, stable yet comfortable and safe cetirizine formulations for ophthalmic administration for the treatment of allergic conjunctivitis, rhinitis, (i.e., the acute phase, the late inflammatory phase, or both) and allergic rhinoconjunctivitis. Such formulations for administration directly to the eye would be advantageous over systemic oral formulations and nasal sprays due to faster action and avoidance of the side effects associated with systemic administration.

SUMMARY OF THE INVENTION

The present invention provides comfortable topical ophthalmic formulations for the treatment of both acute and late phase signs of allergic conjunctivitis, rhinitis, as well as rhinoconjunctivitis which contain a combination of ingredients which act synergistically to relieve the signs and symptoms of allergic conjunctivitis and/or rhinitis and/or rhinoconjunctivitis, particularly ocular itching and/or nasal symptoms (e.g., ocular itching, redness, swelling, tearing, running nose, nasal itching, itchy palate, itchy ear, sneezing, nasal/sinus congestion). In contrast to oral administration of allergy medication, topical ophthalmic allergy formulations of the invention alleviate or reduce drowsiness and systemic exposure to large doses. In particular, the formulations described herein provide stable formulations comprising a low concentration of cetirizine suitable for ophthalmic use in a comfortable ophthalmic formulation when instilled in the eye. By suitable for ophthalmic uses meant that the formulation is stable, comfortable, efficacious and safe when instilled in the eye.

The present invention is based on the surprising discovery that stable topical ophthalmic formulations comprising a low concentration of cetirizine can be prepared without the use of a cyclodextrin or other solubilizer compound, that is both comfortable when instilled in the eye and effective to mitigate the symptoms of allergic conjunctivitis, rhinitis, and/or rhinoconjunctivitis, particularly ocular itching and/or nasal symptoms (e.g., ocular itching, redness, swelling, tearing, running nose, nasal itching, itchy palate, itchy ear, sneezing, nasal/sinus congestion). The invention also provides methods for the treatment of allergic conjunctivitis, rhinitis, and/or rhinoconjunctivitis in a subject in need of such treatment by administering a cetirizine formulation of the invention directly to the eye of the subject. Surprisingly, once a day dosing of the low concentration cetirizine formulations of the invention is effective to mitigate the symptoms of allergic conjunctivitis, rhinitis, and/or rhinoconjunctivitis, particularly ocular itching and/or nasal symptoms (e.g., ocular itching, redness, swelling, tearing, running nose, nasal itching, itchy palate, itchy ear, sneezing, nasal/sinus congestion). Of note, surprisingly the formulations when applied to the eye have a significant impact on nasal symptoms even though the amount of active pharmaceutical ingredient applied to the eye in the eyedrop is significant less than the amount needed to apply in other marketed formulations of nasal sprays.

The invention also provides stable ophthalmic formulations of cetirizine in combination with one or more active ingredients including but not limited to a vasoconstrictor such naphazoline or oxymetazoline, and/or a steroid such as fluticasone, or combinations thereof. The combination formulations of cetirizine are effective in mitigating the signs and symptoms of both acute and late phase allergic conjunctivitis, rhinitis, and/or rhinoconjunctivitis such as ocular itching, redness, chemosis, tearing and lid swelling, and nasal symptoms such as nasal congestion, nasal itching, sneezing, rhinorrhea, itch palate, and itchy ear, as well as allergic rhinoconjunctivitis which may contain both ocular and nasal components.

More specifically, the combination formulations of the invention (e.g., cetirizine and fluticasone) provide a comprehensive treatment benefit for both acute and late phase reactions of allergic conjunctivitis, rhinitis, and rhinoconjunctivitis that cannot be achieved by the use of a single anti-allergic, or other active agent, alone. Antihistamines and mast cell stabilizers such as cetirizine do not effectively block all allergic and pro-inflammatory mediators from the mast cell. Cetirizine, and other antihistamines and mast cell stabilizers, effectively masks itching but has minimal effects on redness, tearing, swelling and inflammation. However, when cetirizine is combined with another active agent which can halt the transcription and production of inflammatory mediators and down-regulate the production of anti-inflammatory mediator, such as a steroid (e.g., fluticasone), treatment of the signs and symptoms of acute and late phase allergic conjunctivitis ((i.e., the aggregate disease), rhinitis, and rhinoconjunctivitis is achieved. Likewise, such combination formulations provide a comprehensive treatment benefit for rhinitis and rhinoconjunctivitis that cannot be achieved by the use of a single anti-allergic, or other active agent alone, for these same reasons.

In one particular embodiment, the cetirizine formulation of the invention comprises a stable ophthalmic formulation of cetirizine as the only active ingredient at a concentration of 0.01% to 1.0% (w/v), preferably 0.05% to 0.5% (w/v), more preferably 0.08% to 0.12% (w/v) or any specific value within said ranges. Preferably, cetirizine is in the form of cetirizine hydrochloride or dihydrochloride. Surprisingly, the stable cetirizine formulation is achieved without the use of a cyclodextrin, or other solubilizing compound, which were described as being required in U.S. Pat. No. 5,419,898.

In another particular embodiment, the invention provides a stable ophthalmic formulation of cetirizine in combination with fluticasone. Preferably, cetirizine is in the form of cetirizine hydrochloride or dihydrochloride. In certain embodiments, cetirizine is present in the formulation at a concentration of 0.05% to 1.0% (w/v), or any specific value within said range. For example, cetirizine is formulated at a concentration of 0.050% to 0.075%, 0.075% to 0.1%, 0.1% to 0.25%, 0.25% to 0.50%, 0.50% to 0.75%, or 0.75% to 1.0% (w/v), or any specific value within said ranges). In particular embodiments, cetirizine is formulated at a concentration of 0.05%, 0.06%, 0.07% 0.08%, %, 0.09%, 0.1%, 0.12%, 0.13%, 0.14%, 0.15%, 0.2%, 0.25%, 0.3%, 0.35%, 0.4%, 0.45%, 0.5%, 0.6%, 0.7%, 0.8%, 0.9%, or 1.0% (w/v). In certain embodiments, fluticasone is present in the formulation at a concentration of 0.001% to 1.0% (w/v), or any specific value within said range. Preferably, fluticasone is present in the formulation at a concentration of 0.001% and 0.2% (w/v), or any specific value within said range. For example, fluticasone is formulated at a concentration of 0.001%, 0.002%, 0.003%, 0.004%, 0.005%, 0.006%, 0.007%, 0.008%, 0.009%, 0.01%, 0.015%, 0.025%, or 0.2% (w/v). In a particular embodiment, cetirizine is present in the formulation at a concentration of 0.1% (w/v) and fluticasone is present in the formulation at a concentration of 0.005% (w/v). In a another particular embodiment, cetirizine is present in the formulation at a concentration of 0.08% to 0.12% (w/v) and fluticasone is present in the formulation at a concentration of 0.004% to 0.006% (w/v). In another particular embodiment, cetirizine is present in the formulation at a concentration of 0.25% (w/v) and fluticasone is present in the formulation at a concentration of 0.01% (w/v). The stable cetirizine/fluticasone formulation is achieved without the use of a cyclodextrin, or other solubilizing compound. The cetirizine alone, and combination formulations of the invention (e.g., cetirizine/fluticasone) are stable and comfortable upon instillation in the eye. Surprisingly, the cetirizine/fluticasone formulations of the invention do not increase intraocular pressure in the eye after repeated use (e.g., after 14 days) and that it was possible to identify a clinically effective dose when used once daily (QD). As such the cetirizine combination formulations of the invention are safe for ocular use.

In certain embodiments, the cetirizine alone and cetirizine combination formulations of the invention are formulated in a vehicle comprising 1% Polyethylene Glycol 400, NF; 0.2% Dibasic Sodium Phosphate, Anhydrous, USP; 0.25% Hypromellose, USP; 0.1% Polysorbate 80, NF; 1.2% to 1.8% Glycerin (or any specific value within said range), USP; 0.025% Edetate Disodium, USP; 0.01% Benzalkonium Chloride, NF (pH 7.0).

In some embodiments, the stable ophthalmic cetirizine formulations of the invention comprise a tear substitute. In particular embodiments, the tear substitute is hydroxypropylmethyl cellulose (Hypromellose or HPMC). According to some embodiments, the concentration of HPMC ranges from about 0.1% to about 2% w/v, or any specific value within said range. According to some embodiments, the concentration of HPMC ranges from about 0.5% to about 1% w/v, or any specific value within said range. In a preferred embodiments, the concentration of HPMC ranges from about 0.1% to about 1.0% w/v, or any specific value within said range (e.g., 0.1-0.2%, 0.2-0.3%, 0.3-0.4%, 0.4-0.5%, 0.5-0.6%, 0.6-0.7%, 0.7-0.8%, 0.8-0.9%, 0.9-1.0%; about 0.2%, about 0.21%, about 0.22%, about 0.23%, about 0.24%, about 0.25%, about 0.26%, about 0.27%, about 0.28%, about 0.29%, about 0.30%, about 0.70%, about 0.71%, about 0.72%, about 0.73%, about 0.74%, about 0.75%, about 0.76%, about 0.77%, about 0.78%, about 0.79%, about 0.80%, about 0.81%, about 0.82%, about 0.83%, about 0.84%, about 0.85%, about 0.86%, about 0.87%, about 0.88%, about 0.89%, or about 0.90%).

In another particular embodiment the tear substitute is carboxymethyl cellulose (CMC). According to some embodiments, the concentration of CMC ranges from about 0.1% to about 2% w/v, or any specific value within said range. According to some embodiments, the concentration of CMC ranges from about 0.1% to about 1% w/v, or any specific value within said range. In a preferred embodiments, the concentration of CMC ranges from about 0.7% to about 0.9% w/v, or any specific value within said range (i.e., about 0.70%, about 0.71%, about 0.72%, about 0.73%, about 0.74%, about 0.75%, about 0.76%, about 0.77%, about 0.78%, about 0.79%, about 0.80%, about 0.81%, about 0.82%, about 0.83%, about 0.84%, about 0.85%, about 0.86%, about 0.87%, about 0.88%, about 0.89%, or about 0.90%).

In yet another particular embodiment, the stable ophthalmic cetirizine formulations of the invention comprise a polymeric, mucoadhesive vehicle. Examples of mucoadhesive vehicles suitable for use in the methods or formulations of the invention include but are not limited to aqueous polymeric suspensions comprising one or more polymeric suspending agents including without limitation dextrans, polyethylene glycol, polyvinylpyrolidone, polysaccharide gels, Gelrite®, cellulosic polymers, and carboxy-containing polymer systems. In a particular embodiment, the polymeric suspending agent comprises a crosslinked carboxy-containing polymer (e.g., polycarbophil). In another particular embodiment, the polymeric suspending agent comprises a polyethylene glycol (PEG). Examples of cross-linked carboxy-containing polymer systems suitable for use in the topical stable ophthalmic cetirizine formulations of the invention include but are not limited to Noveon AA-1, Carbopol®, and/or DuraSite® (InSite Vision).

Optionally, the formulations of the invention contain a preservative. In particular embodiments the preservative is benzalkonium chloride or a derivative thereof (e.g., Polyquad®), sorbate, sodium perborate, or a stabilized oxychloro complex (e.g., Purite®).

According to some embodiments, the ophthalmic formulations of the present invention has a viscosity that ranges from about 30 to about 150 centipoise (cpi), preferably about 50 to about 120 cpi, even more preferably about 60 to about 115 cpi (or any specific value within said ranges). According to preferred embodiments, the ophthalmic formulations of the present invention has a viscosity that ranges from about 60 to about 80 cpi, or any specific value within said range (i.e., about 60 cpi, about 61 cpi, about 62 cpi, about 63 cpi, about 64 cpi, about 65 cpi, about 66 cpi, about 67 cpi, about 68 cpi, about 69 cpi, about 70 cpi, about 71 cpi, about 72 cpi, about 73 cpi, about 74 cpi, about 75 cpi, about 76 cpi, about 77 cpi, about 78 cpi, about 79 cpi, or about 80 cpi).

The invention also provides methods of treating and preventing the symptoms of allergic conjunctivitis by administering a stable cetirizine formulation of the invention (i.e., cetirizine alone or in combination with an additional active agent such as a steroid (e.g., fluticasone) or a vasoconstrictor (e.g., naphazoline or oxymetazoline) directly to the eye of a subject in need of such treatment or prevention. The formulation of the invention is administered once a day (q.d.). Once a day administration is particularly advantageous it limits drug exposure and therefore reduced unwanted side effects. In certain embodiments, the methods of the invention (i.e., administration of a formulation of the invention directly to the eye) are also effective to treat nasal symptoms associated with allergic conjunctivitis, rhinitis, and rhinoconjunctivitis. The invention also provides methods of treating and preventing the symptoms of allergic rhinoconjunctivitis by administering a stable cetirizine formulation of the invention (i.e., cetirizine alone or in combination with an additional active agent such as a steroid (e.g., fluticasone) or a vasoconstrictor (e.g., naphazoline or oxymetazoline) directly to the eye of a subject in need of such treatment or prevention. The active drug of the eyedrop then drains through the nasolacrimal duct into the nasal mucosal tissue to exert surprising effects. By providing a treatment option in eye drop form, the present invention will improve quality of life in patients with allergic conjunctivitis, rhinoconjunctivitis, and rhinitis (See e.g., Berger et al., *Ann. Allergy Asthma Immunol.* October 95(4), 361-71 (2005).

The invention further provides kits comprising a pharmaceutical composition of cetirizine formulated for ophthalmic use and instructions for such use. Other features and advantages of the invention will become apparent from the following detailed description and claims.

BRIEF DESCRIPTION OF THE DRAWINGS

FIG. 4 is a line graph comparing the efficacy of Fluticasone 0.001%, 0.005% and 0.01% as compared to vehicle in reducing ocular itching assessed on a scale of 0 (no itching) to 4 (severe itching) over time.

FIG. 22 is a chart summarizing the incidence of adverse events associated with instillation of Fluticasone 0.001%, 0.005% and 0.01% in the eye.

FIG. 35 are tables showing comparison of 0.1% cetirizine/ 0.005% Fluticasone with Pataday and Alcaftadine treatment on mean itching score at visit 3 and 4A post CAC.

FIG. 40 are tables showing comparison of 0.1% cetirizine/ 0.005% Fluticasone with Vehicle treatment on mean ocular itching treatment differences by visit.

FIG. 41 are tables comparison of 0.1% cetirizine/0.005% Fluticasone with vehicle on mean conjunctival redness treatment differences by visit.

FIG. 42 are tables showing comparison of 0.1% cetirizine/ 0.005% Fluticasone with individual component treatment on mean ocular itching treatment differences by visit FIG. 43 are tables comparison of 0.1% cetirizine/0.005% Fluticasone with individual component on mean conjunctival redness treatment differences (Active-Vehicle) by visit.

FIG. 44 are tables showing of 0.1% cetirizine/0.005% Fluticasone with Vehicle: ciliary redness treatment differences by visit.

DETAILED DESCRIPTION OF THE INVENTION

Figure 1A:
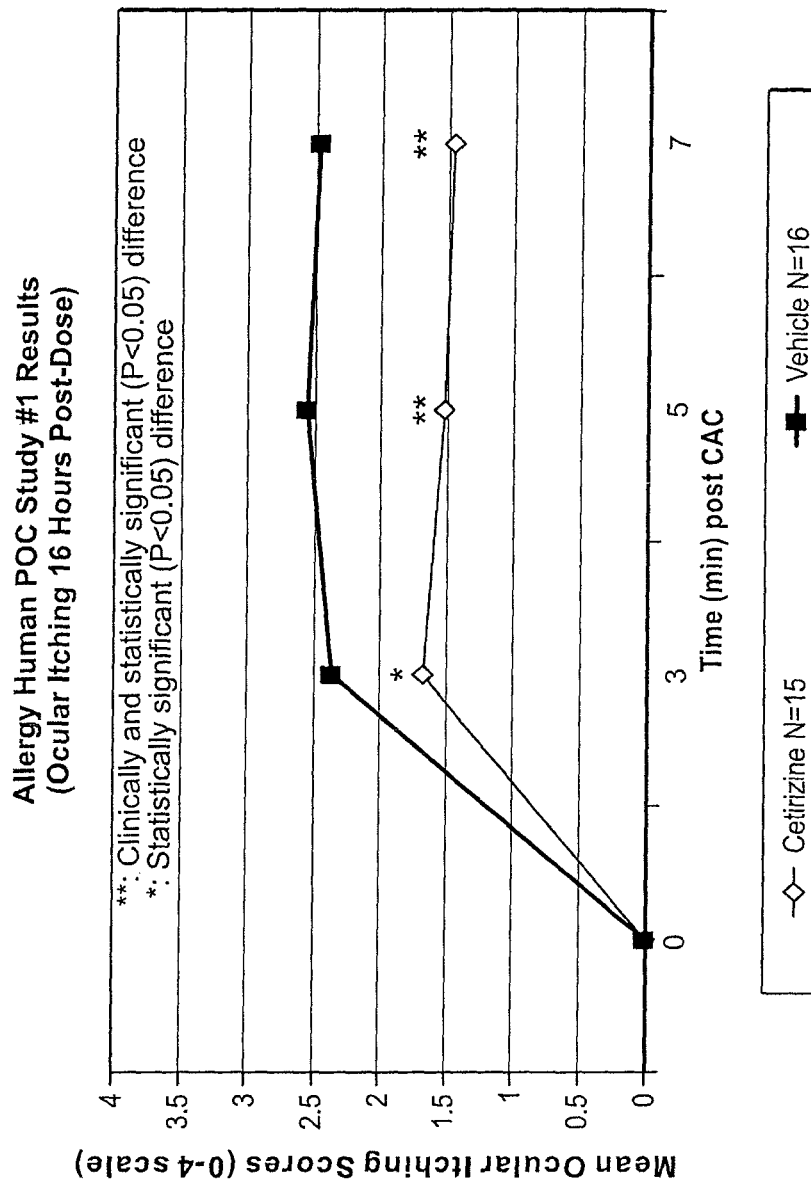
FIG. 1A is a line graph depicting the efficacy of a 0.1% cetirizine formulation reducing of ocular itching as compared to a vehicle control. The mean ocular itching score (scale of 0 to 4) is shown at 0, 3, 5, and 7 minutes after conjunctival challenge with allergen.

The invention is based in part on the discovery that low concentrations of cetirizine (i.e., less than 1%) can be prepared as a stable ophthalmic formulation, without the use of a cyclodextrin or other solubilizing compound. Such formulations are comfortable and safe for ocular use and effective at reducing the symptoms of allergic conjunctivitis, rhinitis, and/or allergic rhinoconjunctivitis, particularly ocular itching, redness, swelling, and tearing and/or nasal symptoms (e.g., itchy, running nose, sneezing, nasal/sinus congestion, itchy palate, itchy ear). The invention is further based upon the surprising discovery that formulation of 0.01% cetirizine and 0.005% Fluticasone provide a greater reduction of the symptoms of allergic conjunctivitis, rhinitis, and/or allergic rhinoconjunctivitis, particularly ocular itching, redness, swelling, and/or nasal symptoms (e.g., itchy, running nose, sneezing, nasal/sinus congestion) than either component when administered alone at the same concentration or at higher concentrations when administered together. More surprisingly, the combination when administered to the eye also provides reduction of nasal symptoms at least to the level seen with much higher doses in existing marketed nasal products.

The historical difficulty in preparing cetirizine as an ophthalmic solution with satisfactory safety and stability profiles is well recognized in the art due to the fact that cetirizine aggregates in solution at low concentrations, and is highly irritating to the ocular surface at high concentrations, being a strong acid. Without intending to be bound by any theory, it was believed necessary to reduce the possibility of salt formation and metal based degradation in order to arrive at a stable formulation. As such, the addition of counter ions or metal based buffers that could promote salt formation, precipitation, or metal based degradation were minimized or excluded from the cetirizine formulations of the invention. Furthermore, it was discovered that the pH could be adjusted to approximately 7.0 with no adverse effects on stability, to improve the comfort of the formula.

The invention features novel topical ophthalmic formulations comprising an effective amount of cetirizine, or a pharmaceutically acceptable salt thereof, in a pharmaceutically acceptable carrier. Pharmaceutically acceptable cetirizine salts include cetirizine hydrochloride or cetirizine dihydrochloride. In particular embodiments, the invention provides stable ophthalmic formulations of cetirizine as the only active agent in the formulations. The invention also features ophthalmic formulations of cetirizine in combination with one or more additional active ingredients selected from oxymetazoline, naphazoline and fluticasone. In a preferred embodiment, the invention features an ophthalmic formulation of 0.1% cetirizine and 0.005% Fluticasone. Such preferred combination formulations are effective in further mitigating the acute and late phase signs and symptoms of allergic conjunctivitis, rhinitis, and rhinoconjunctivitis, such as ocular itching, redness, chemosis, lid swelling and also nasal symptoms. Such formulations are also effective in mitigating the signs and symptoms of rhinoconjunctivitis, such as runny nose (rhinorrhea), sneezing, nasal/sinus congestion, nasal itching, itchy palate, itchy ear, and red, watery, swollen, and/or itchy eyes.

The comfort, safety, efficacy, solubility, and stability of the ophthalmic formulations of the invention could not have been predicted by one skilled in the art. Many antihistamines have been developed over the years by various companies for different indications. However, not all of these can be formulated or are effective as an eyedrop. Likewise not all antihistamines have the same duration of action. For example the potent antihistamine levocabastine has a duration of 2-4 hours; recently approved bepotastine (Bepreve®-ISTA), indicated for twice daily dosing, has an 8 hour duration; olopatadine 0.1% (Patanol®) indicated for twice daily dosing, has an 8 hour duration; and olopatadine 0.2% (Pataday®), indicated for once daily dosing, has a 16 hour duration of action. Therefore the efficacy is not predictable. In one study (Berdy et al, 1990), a panel of antihistamines were screened yet only a few were suitable for the eye based on comfort, formulation, irritation, and efficacy. As evidenced by Berdy et al., one skilled in the art could not have predicted which of the antihistamines would be ideal for ocular use or for treating ocular allergy. The invention is based, in part, upon the surprising and unpredictable discovery that an antihistamine and a steroid, (in particular of cetirizine and fluticasone) when combined, act synergistically to treat both the acute and late phase reactions of allergic conjunctivitis, rhinitis as well as allergic rhinoconjunctivitis.

In some embodiment, the cetirizine formulations of the invention comprise one or more tear substitute components. The cetirizine component provides relief of the symptoms of allergic conjunctivitis, and the one or more tear substitute component provides ocular surface protection via enhancement of the tear film (as evident by increased tear film break up time), and can act to enhance dwell time on the ocular surface thus increasing duration of activity. An effective amount of such formulations may be used to treat and/or prevent signs and symptoms associated with acute and/or late phase allergic conjunctivitis, rhinitis, and/or rhinoconjunctibitis, urban allergy, dry eye and/or general eye irritation, and can also be used to treat another eye disorder if it contains a drug for that disorder. An effective amount of such formulations may also be used to treat and/or prevent signs and symptoms of allergic rhinoconjunctivitis. Such formulations provide a comfortable ophthalmic formulation when instilled in the eye and have enhanced efficacy and/or duration of action over formulations of cetirizine that are not combined with such other agents.

The superior efficacy of the combination cetirizine/tear substitute formulations is attributed to, among other things, the synergistic effect of the combination of ingredients in them. The combination of cetirizine and tear substitute, act synergistically to provide a longer dwell time of the cetirizine on the ocular surface, thus increasing duration and efficacy of action, and to prolong the integrity of the tear film thereby providing protection of the ocular surface (e.g., by increasing the tear film break up time and/or the Ocular Protection Index). As such, the compositions of the invention are comfortable upon instillation into the eye, and may be used for relief of acute or chronic allergic conjunctivitis, dry eye, rhinitis, and rhinoconjunctivits, or urban allergy, and are particularly suitable for both intermittent and long term use.

Synergy, in general, may be defined as two or more agents working together to produce a result not obtainable by any of the agents independently. In particular in the context of the present invention synergy is a result greater than the results of the individual agents at the same concentration as in the combination. Synergy may also be defined as clinical superiority of the two or more agent compared to the individual agents alone. By clinical superiority is meant that the difference between the combination treatment and treatment with the individual agents alone at the same concentration is clinically or statistically significant. Clinical significance is meant that the treatment provides a clinical benefit, that is a reduction of a sign or symptom of the disease or disorder being treated.

Formulations

In the context of this patent all concentrations are given for the cetirizine free base. The concentration for the cetirizine salt (e.g. cetirizine hydrochloride or dihydrochloride) can be calculated by multiplying the free base concentration by 1.188. e.g. 0.1% cetirizine free base is equivalent to 0.1188% cetirizine dihydrochloride salt (0.1%×1.188=0.11881%).

Preferably, the ophthalmic formulations according to the present invention are formulated as solutions, suspensions, ointments, gels, emulsions, oils, and other dosage forms for topical administration. Aqueous solutions are generally preferred, based on ease of formulation, as well as a patient's ability to easily administer such compositions by means of instilling one to two drops of the solutions in the affected eyes. However, the compositions may also be suspensions, viscous or semi-viscous gels, or other types of solid or semi-solid compositions or sustained release devices or mechanisms that are placed in or around the eye. In one embodiment, the cetirizine formulations of the invention are aqueous formulations. The aqueous formulations of the invention are typically more than 50%, preferably more than 75%, and most preferably more than 90% by weight water. Preferably, the aqueous formulation does not contain a cyclodextrin or other solubilizer compound because cyclobetadextran may in some cases inpact stability, or pharmacokinetics of the drug. Stable aqueous formulations of cetirizine are achieved by minimizing/excluding the addition of counter ions or metal based buffers that could promote salt formation, precipitation, or metal based degradation. In another embodiment, the cetirizine formulations are lyophilized formulations.

Active Agents

Cetirizine is the primary active agent in the ophthalmic formulations of the present invention, and in certain embodiments, the only active agent in the formulations of the invention. In certain embodiments of the invention, cetirizine, or a pharmaceutically acceptable salt thereof, is formulated at a concentration of 0.01% to 1.0% (w/v). Preferably, cetirizine is in the form of cetirizine hydrochloride or dihydrochloride. In certain embodiments, cetirizine is formulated at a concentration of 0.05% to 0.075%, 0.075% to 0.1%, 0.08% to 0.12%, 0.1% to 0.25%, 0.25% to 0.50%, 0.50% to 0.75%, or 0.75% to 1.0% (w/v). In particular embodiments, cetirizine is formulated at a concentration of 0.05% to 1.0% (w/v), or any specific value within said range. For example, cetirizine is formulated at a concentration of 0.05%, 0.06%, 0.07%, 0.08%, 0.09%, 0.1%, 0.12%, 0.13%, 0.14%, 0.15%, 0.16%, 0.17%, 0.18%, 0.19% 0.2%, 0.25%, 0.3%, 0.35%, 0.4%, 0.45%, 0.5%, 0.6%, 0.7%, 0.8%, 0.9%, or 1.0% (w/v). (w/v). In one embodiment, the cetirizine formulation of the invention comprises cetirizine hydrochloride or dihydrochloride as the only active ingredient at a concentration of 0.01% to 1.0%

(w/v), preferably 0.05% to 0.5% (w/v), more preferably 0.1% to 0.25% (w/v), most preferably 0.08% to 0.12% (w/v) (or any specific value within said ranges).

Cetirizine may be formulated with other active agents as described herein. For example, cetirizine may be formulated with one or more additional anti-allergic agents. The term "anti-allergenic agent" refers to a molecule or composition that treats allergic conjunctivitis, rhinitis and/or rhinoconjunctivitis or reduces a symptom of allergic conjunctivitis, rhinitis and/or rhinoconjunctivitis. The term "allergic conjunctivitis" refers to any allergic disease of the eye, e.g., seasonal/perennial allergic conjunctivitis, vernal keratoconjunctivitis, giant papillary conjunctivitis, perennial allergic conjunctivitis and atopic keratoconjunctivitis. The signs and symptoms of ocular allergies include chemosis, eye itching, tearing, redness and swelling, and may also co-exist with nasal symptomotology. The term "rhinitis" refers to any allergic or non-allergic disorder of the nose, e.g. seasonal or perennial allergic rhinitis, vasomotor rhinitis, and the signs and symptoms include nasal itching, sneezing, rhinorrhea, nasal congestion, itchy palate, itchy ear. The term "allergic rhinoconjunctivitis" refers to a combination of nasal and ocular symptoms characterized by inflammation of the lining of the tissue of the eyes and nose due to an allergy with or without infection, causing nasal discharge, mucus, sneezing, irritation, swollen, and red, watery, itchy eyes. Non-limiting examples of anti-allergic agents include "antihistamines" or drugs which block histamine from binding to the histamine receptors, "mast cell stabilizers" or drugs that block the release of histamine and other substances from the mast cell, "drugs with multiple modes of action" or drugs that are anti-allergenic agents having multiple modes of action (e.g. drugs that are antihistamines and mast cell stabilizers, drugs with antihistamine, mast cell stabilizing and anti-inflammatory activity, etc.), steroids, and nonsteroidal anti-inflammatory drugs or "NSAIDs."

In certain embodiments, cetirizine is formulated with one or more additional active agents selected from a mast cell stabilizer such as nedocromil, iodoxamide, cromolyn, or cromolyn sodium; a non-steroidal anti-inflammatory drug ("NSAID") such as diclofenac or ketorolac tromethamine, bromfenac, or nepafenac; a vasoconstrictor such as naphazoline, tetrahydrozoline or oxymetazoline; a topical steroid such as fluticasone, beclomethasone, budesonide, diflorasone, triaminicinolone, clobetasol, difluprednate, prednisolone, dexamethasone, halobetasol, or mometasone; an antihistamine such as antazoline, astemizole, alcaftadine, azelastine, bepotastine, bilastine, brompheniramine, chlorpheniramine, clemastine, desloratidine, dexbrompheniramine, diphenhydramine, doxylamine, ebastine, emedastine, epinastine, fexofenadine, hydroxyzine, ketotifen, levocabastine, levocetirizine, loratidine, mequitazine, mizolastine, olopatadine, oxatomide, phenindamine, pheniramine, pyrilamine, terfenidine, and triprolidine; or an alpha-adrenergic agonist such as epinephrine, fenoxazoline, indanazoline, naphazoline, oxedrine, phenylephrine, tefazoline, tetryzoline, tramazoline, tymazoline, oxymetazoline, or xylometazoline.

In certain embodiments, cetirizine is formulated with one or more additional active agents such as a vasoconstrictor (e.g., naphazoline or oxymetazoline), or a steroid (e.g., fluticasone).

Naphazoline (in the hydrochloride form) is the common name for 2-(1-naphthylmethyl)-2-imidazoline hydrochloride. It is a sympathomimetic agent with marked alpha adrenergic activity. It is a vasoconstrictor with a rapid action in reducing swelling when applied to mucous membrane. It acts on alpha-receptors in the arterioles of the conjunctiva to produce constriction, resulting in decreased congestion. Oxymetazoline is a selective alpha-1 agonist and partial alpha-2 agonist topical decongestant, used in the form of oxymetazoline hydrochloride in commercially available nasal sprays. Oxymetazoline has sympathomimetic properties, and thus constricts the blood vessels of the nose and sinuses via activation of alpha-2 adrenergic receptors. Fluticasone is a potent synthetic corticosteroid often prescribed as treatment for asthma and allergic rhinitis.

In certain embodiments, cetirizine is formulated at a concentration of from 0.05% to 0.50% (w/v), in combination with naphazoline at a concentration of from 0.01% to 0.5% (w/v), preferably 0.01% to 0.1% (w/v), preferably 0.05% to 0.1% (w/v), more preferably 0.09% to 0.1% (w/v). In particular embodiments, cetirizine is formulated at a concentration of 0.01%, 0.05%, 0.06%, 0.07%, 0.08%, 0.09%, 0.10%, 0.15%, 0.20%, 0.25%, 0.30%, 0.35%, 0.45%, or 0.50% (w/v) in combination with naphazoline at a concentration of 0.01%, 0.02%, 0.03%, 0.04%, 0.05%, 0.06% 0.07%, 0.08%, 0.09% or 0.10% (w/v).

In certain embodiments, cetirizine is formulated at a concentration of from 0.05% to 0.50% (w/v) in combination with oxymetazoline at a concentration of from 0.01% to about 0.2% (w/v), preferably 0.01% to 0.1% (w/v), more preferably 0.03% to 0.05% (w/v). In particular embodiments, cetirizine is formulated at a concentration of 0.05%, 0.06%, 0.07%, 0.08%, 0.09%, 0.10%, 0.15%, 0.20%, 0.25%, 0.30%, 0.35%, 0.45%, or 0.50% (w/v) in combination with oxymetazoline at a concentration of 0.01%, 0.02%, 0.03%, 0.04%, 0.05%, 0.06%, 0.07% 0.09% or 0.10% (w/v).

In certain embodiments, cetirizine is formulated at a concentration of from 0.05% to 0.50% (w/v) in combination with fluticasone at a concentration of from 0.001% to 1.0% (w/v), preferably 0.001% to 0.2% (w/v), or any specific value within said ranges. In particular embodiments, cetirizine is formulated at a concentration of 0.05%, 0.06%, 0.07%, 0.08%, 0.09%, 0.10%, 0.12% 0.15%, 0.20%, 0.25%, 0.30%, 0.35%, 0.45%, or 0.50% (w/v) in combination with fluticasone at a concentration of 0.001%, 0.002%, 0.003%, 0.004%, 0.005%, 0.006%, 0.007%, 0.008%, 0.009%, 0.01%, 0.015%, 0.05%, 0.1%, 0.2%, 0.5%, or 1% (w/v). In a particular embodiment, the cetirizine is present in the formulation at a concentration of 0.25% (w/v) and the fluticasone is present in the formulation at a concentration of 0.01% (w/v). In another particular embodiment, the cetirizine is present in the formulation at a concentration of 0.1% (w/v) and the fluticasone is present in the formulation at a concentration of 0.005% (w/v). In another particular embodiment, the cetirizine is present in the formulation at a concentration of 0.08% to 0.12% (w/v) and the fluticasone is present in the formulation at a concentration of 0.004% to 0.006% (w/v).

In certain embodiments, the viscosity of the cetirizine formulations of the invention (i.e. cetirizine alone or in combination with an additional active agent) ranges from 1-50 centipoise (cpi), or any specific value within said range. In a particular embodiment, the viscosity of the cetirizine formulations of the invention range from 5-30 cpi, preferably 10-20 cpi.

Excipients

In some embodiments, the cetirizine formulations of the invention comprise one or more pharmaceutically acceptable excipients. The term excipient as used herein broadly refers to a biologically inactive substance used in combination with the active agents of the formulation. An excipient can be used, for example, as a solubilizing agent, a stabilizing agent, a surfactant, a demulcent, a viscosity agent, a diluent, an inert carrier, a preservative, a binder, a disintegrant, a coating agent, a flavoring agent, or a coloring agent. Preferably, at least one excipient is chosen to provide one or more beneficial physical properties to the formulation, such as increased stability and/or solubility of the active agent(s). A "pharmaceutically acceptable" excipient is one that has been approved by a state or federal regulatory agency for use in animals, and preferably for use in humans, or is listed in the U.S. Pharmacopia, the European Pharmacopia or another generally recognized pharmacopia for use in animals, and preferably for use in humans.

Further examples of excipients include certain inert proteins such as albumins; hydrophilic polymers such as polyvinylpyrrolidone; amino acids such as aspartic acid (which may alternatively be referred to as aspartate), glutamic acid (which may alternatively be referred to as glutamate), lysine, arginine, glycine, and histidine; fatty acids and phospholipids such as alkyl sulfonates and caprylate; surfactants such as sodium dodecyl sulphate and polysorbate; nonionic surfactants such as such as TWEEN®, PLURONICS®, or a polyethylene glycol (PEG) designated 200, 300, 400, or 600; a Carbowax designated 1000, 1500, 4000, 6000, and 10000; carbohydrates such as glucose, sucrose, mannose, maltose, trehalose, and dextrins, including cyclodextrins; polyols such as mannitol and sorbitol; chelating agents such as EDTA; and salt-forming counter-ions such as sodium.

Examples of carriers that may be used in the formulations of the present invention include water, mixtures of water and water-miscible solvents, such as $C_1$- to $C_7$-alkanols, vegetable oils or mineral oils comprising from 0.5 to 5% non-toxic water-soluble polymers, natural products, such as gelatin, alginates, pectins, tragacanth, karaya gum, xanthan gum, carrageenin, agar and acacia, starch derivatives, such as starch acetate and hydroxypropyl starch, and also other synthetic products, such as polyvinyl alcohol, polyvinylpyrrolidone, polyvinyl methyl ether, polyethylene oxide, preferably cross-linked polyacrylic acid, such as neutral Carbopol, or mixtures of those polymers. The concentration of the carrier is, typically, from 1 to 100000 times the concentration of the active ingredient.

In a particular embodiment, the carrier is a polymeric, mucoadhesive vehicle. Examples of mucoadhesive vehicles suitable for use in the methods or formulations of the invention include but are not limited to aqueous polymeric suspensions comprising one or more polymeric suspending agents including without limitation dextrans, polyethylene glycol, polyvinylpyrolidone, polysaccharide gels, Gelrite®, cellulosic polymers, and carboxy-containing polymer systems. In a particular embodiment, the polymeric suspending agent comprises a crosslinked carboxy-containing polymer (e.g., polycarbophil). In another particular embodiment, the polymeric suspending agent comprises polyethylene glycol (PEG). Examples of cross-linked carboxy-containing polymer systems suitable for use in the topical stable ophthalmic cetirizine formulations of the invention include but are not limited to Noveon AA-1, Carbopol®, and/or DuraSite® (InSite Vision).

In particular embodiments, the cetirizine formulations of the invention comprise one or more excipients selected from among the following: a tear substitute, a tonicity enhancer, a preservative, a solubilizer, a viscosity enhancing agent, a demulcent, an emulsifier, a wetting agent, a sequestering agent, and a filler. The amount and type of excipient added is in accordance with the particular requirements of the formulation and is generally in the range of from about 0.0001% to 90% by weight.

Tear Substitutes

The term "tear substitute" refers to molecules or compositions which lubricate, "wet," approximate the consistency of endogenous tears, aid in natural tear build-up, or otherwise provide temporary relief of dry eye signs or symptoms and conditions upon ocular administration. A variety of tear substitutes are known in the art and include, but are not limited to: monomeric polyols, such as, glycerol, propylene glycol, and ethylene glycol; polymeric polyols such as polyethylene glycol; cellulose esters such hydroxypropylmethyl cellulose, carboxymethyl cellulose sodium and hydroxy propylcellulose; dextrans such as dextran 70; water soluble proteins such as gelatin; vinyl polymers, such as polyvinyl alcohol, polyvinylpyrrolidone, and povidone; and carbomers, such as carbomer 934P, carbomer 941, carbomer 940 and carbomer 974P. Many such tear substitutes are commercially available, which include, but are not limited to cellulose esters such as Bion Tears®, Celluvisc®, Genteal®, OccuCoat®, Refresh®, Systane®, Systane Ultra®, Endura®, Liquigel®, Teargen II®, Tears Naturale®, Tears Natural II®, Tears Naturale Free®, and TheraTears®; and polyvinyl alcohols such as Akwa Tears®, HypoTears®, Moisture Eyes®, Murine Lubricating®, and Visine Tears®, Soothe®. Tear substitutes may also be comprised of paraffins, such as the commercially available Lacri-Lube@ ointments. Other commercially available ointments that are used as tear substitutes include Lubrifresh PM®, Moisture Eyes PM® and Refresh PM®.

In one preferred embodiment of the invention, the tear substitute comprises hydroxypropylmethyl cellulose (Hypromellose or HPMC). According to some embodiments, the concentration of HPMC ranges from about 0.1% to about 2% w/v, or any specific value within said range. According to some embodiments, the concentration of HPMC ranges from about 0.5% to about 1.5% w/v, or any specific value within said range. According to some embodiments, the concentration of HPMC ranges from about 0.1% to about 1% w/v, or any specific value within said range. According to some embodiments, the concentration of HPMC ranges from about 0.6% to about 1% w/v, or any specific value within said range. In a preferred embodiments, the concentration of HPMC ranges from about 0.1% to about 1.0% w/v, or any specific value within said range (i.e., 0.1-0.2%, 0.2-0.3%, 0.3-0.4%, 0.4-0.5%, 0.5-0.6%, 0.6-0.7%, 0.7-0.8%, 0.8-0.9%, 0.9-1.0%; about 0.2%, about 0.21%, about 0.22%, about 0.23%, about 0.24%, about 0.25%, about 0.26%, about 0.27%, about 0.28%, about 0.29%, about 0.30%, about 0.70%, about 0.71%, about 0.72%, about 0.73%, about 0.74%, about 0.75%, about 0.76%, about 0.77%, about 0.78%, about 0.79%, about 0.80%, about 0.81%, about 0.82%, about 0.83%, about 0.84%, about 0.85%, about 0.86%, about 0.87%, about 0.88%, about 0.89%, or about 0.90%).

For example, without limitation, a tear substitute which comprises hydroxypropyl methyl cellulose is GenTeal® lubricating eye drops. GenTeal® (CibaVision-Novartis) is a sterile lubricant eye drop containing hydroxypropylmethyl cellulose 3 mg/g and preserved with sodium perborate. Other examples of an HPMC-based tear are provided.

In another preferred embodiment, the tear substitute comprises carboxymethyl cellulose sodium. For example, without limitation, the tear substitute which comprises carboxymethyl cellulose sodium is Refresh® Tears. Refresh® Tears is a lubricating formulation similar to normal tears, containing a, mild non-sensitizing preservative, stabilised oxychloro complex (Purite®), that ultimately changes into components of natural tears when used.

In another preferred embodiment, the tear substitute comprises PEG and/or propylene glycol. For example, without limitation, the tear substitute which comprises PEG and/or propylene glycol is Systane®.

In a preferred embodiment, the tear substitute, or one or more components thereof, is an aqueous solution having a viscosity in a range which optimizes efficacy of supporting the tear film while minimizing blurring, lid caking, etc. Preferably, the viscosity of the tear substitute, or one or more components thereof, ranges from 1-150 centipoise (cpi), e.g., 5-150 cpi, 5-130 cpi, 30-130 cpi, 50-120 cpi, 60-115 cpi (or any specific value within said ranges). In a particular embodiment, the viscosity of the tear substitute, or one or more components thereof, is about 70-90 cpi, or any specific value within said range (for example without limitation, 85 cpi).

Viscosity may be measured at a temperature of 20° C.+/−1° C. using a Brookfield Cone and Plate Viscometer Model VDV-III Ultra$^+$ with a CP40 or equivalent Spindle with a shear rate of approximately 22.50+/−approximately 10 (1/sec), or a Brookfield Viscometer Model LVDV-E with a SC4-18 or equivalent Spindle with a shear rate of approximately 26+/−approximately 10 (1/sec). Alternatively, viscosity may be measured at 25° C.+/−1° C. using a Brookfield Cone and Plate Viscometer Model VDV-III Ultra$^+$ with a CP40 or equivalent Spindle with a shear rate of approximately 22.50+/−approximately 10 (1/sec), or a Brookfield Viscometer Model LVDV-E with a SC4-18 or equivalent Spindle with a shear rate of approximately 26+/−approximately 10 (1/sec).

In some embodiments, the tear substitute, or one or more components thereof is buffered to a pH 5.0 to 9.0, preferably pH 5.5 to 7.5, more preferably pH 6.0 to 7.0 (or any specific value within said ranges), with a suitable salt (e.g., phosphate salts). In some embodiments, the tear substitute further comprises one or more ingredients, including without limitation, glycerol, propyleneglycerol, glycine, sodium borate, magnesium chloride, and zinc chloride.

Salts, Buffers, and Preservatives

The formulations of the present invention may also contain pharmaceutically acceptable salts, buffering agents, or preservatives. Examples of such salts include those prepared from the following acids: hydrochloric, hydrobromic, sulfuric, nitric, phosphoric, maleic, acetic, salicylic, citric, boric, formic, malonic, succinic, and the like. Such salts can also be prepared as alkaline metal or alkaline earth salts, such as sodium, potassium or calcium salts. Examples of buffering agents include phosphate, citrate, acetate, and 2-(N-morpholino)ethanesulfonic acid (MES).

For the adjustment of the pH, preferably to a physiological pH, buffers may especially be useful. The pH of the present solutions should be maintained within the range of 4.0 to 8.0, more preferably about 5.5 to 7.5, more preferably about 6.0 to 7.0. Suitable buffers may be added, such as boric acid, sodium borate, potassium citrate, citric acid, sodium bicarbonate, TRIS, and various mixed phosphate buffers (including combinations of $Na_2HPO_4$, $NaH_2PO_4$ and $KH_2PO_4$) and mixtures thereof. Borate buffers are preferred. Generally, buffers will be used in amounts ranging from about 0.05 to 2.5 percent by weight, and preferably, from 0.1 to 1.5 percent.

In certain embodiments, the topical formulations additionally comprise a preservative. A preservative may typically be selected from a quaternary ammonium compound such as benzalkonium chloride, benzoxonium chloride or the like. Benzalkonium chloride is better described as: N-benzyl-N—($C_8$-$C_{18}$ alkyl)-N,N-dimethylammonium chloride. Further examples of preservatives include antioxidants such as vitamin A, vitamin E, vitamin C, retinyl palmitate, and selenium; the amino acids cysteine and methionine; citric acid and sodium citrate; and synthetic preservatives such as thimerosal, and alkyl parabens, including for example, methyl paraben and propyl paraben. Other preservatives include octadecyldimethylbenzyl ammonium chloride, hexamethonium chloride, benzethonium chloride, phenol, catechol, resorcinol, cyclohexanol, 3-pentanol, m-cresol, phenylmercuric nitrate, phenylmercuric acetate or phenylmercuric borate, sodium perborate, sodium chlorite, alcohols, such as chlorobutanol, butyl or benzyl alcohol or phenyl ethanol, guanidine derivatives, such as chlorohexidine or polyhexamethylene biguanide, sodium perborate, Polyquad®, Germal®II, sorbic acid and stabilized oxychloro complexes (e.g., Purite®). Preferred preservatives are quaternary ammonium compounds, in particular benzalkonium chloride or its derivative such as Polyquad (see U.S. Pat. No. 4,407,791), alkyl-mercury salts, parabens and stabilized oxychloro complexes (e.g., Purite®). Where appropriate, a sufficient amount of preservative is added to the ophthalmic composition to ensure protection against secondary contaminations during use caused by bacteria and fungi.

In particular embodiments, the cetirizine formulations of the invention comprise a preservative selected from among the following: benzalkonium chloride, 0.001% to 0.05%; benzethonium chloride, up to 0.02%; sorbic acid, 0.01% to 0.5%; polyhexamethylene biguanide, 0.1 ppm to 300 ppm; polyquaternium-1 (Omamer M)-0.1 ppm to 200 ppm; hypochlorite, perchlorite or chlorite compounds, 500 ppm or less, preferably between 10 and 200 ppm); stabilized hydrogen peroxide solutions, a hydrogen peroxide source resulting in a weight % hydrogen peroxide of 0.0001 to 0.1% along with a suitable stabilizer; alkyl esters of p-hydroxybenzoic acid and mixtures thereof, preferably methyl paraben and propyl paraben, at 0.01% to 0.5%; chlorhexidine, 0.005% to 0.01%; chlorobutanol, up to 0.5%; and stabilized oxychloro complex (Purite®) 0.001% to 0.5%, or sepazonium 0.0001% to 0.1%.

In another embodiment, the topical formulations of this invention do not include a preservative. Such formulations would be useful for patients who wear contact lenses, or those who use several topical ophthalmic drops and/or those with an already compromised ocular surface (e.g. dry eye) wherein limiting exposure to a preservative may be more desirable.

Viscosity Enhancing Agents and Demulcents

In certain embodiments, viscosity enhancing agents may be added to the cetirizine formulations of the invention. Examples of such agents include polysaccharides, such as hyaluronic acid and its salts, chondroitin sulfate and its salts, dextrans, various polymers of the cellulose family, vinyl polymers, and acrylic acid polymers.

In certain embodiments, the cetirizine formulations of the invention comprise ophthalmic demulcents and/or viscosity enhancing polymers selected from one or more of the following: cellulose derivatives such as carboxymethylcellulose (0.01 to 5%) hydroxyethylcellulose (0.01% to 5%), hydroxypropyl methylcellulose or hypromellose (0.01% to 5%), and methylcelluose (0.02% to 5%); dextran 40/70 (0.01% to 1%); gelatin (0.01% to 0.1%); polyols such as glycerin (0.01% to 5%), polyethylene glycol 300 (0.02% to 5%), polyethylene glycol 400 (0.02% to 5%), polysorbate 80 (0.02% to 3%), propylene glycol (0.02% to 3%), polyvinyl alcohol (0.02% to 5%), and povidone (0.02% to 3%); hyaluronic acid (0.01% to 2%); and chondroitin sulfate (0.01% to 2%).

Viscosity of the stable ophthalmic cetirizine formulations of the invention may be measured according to standard methods known in the art, such as use of a viscometer or rheometer. One of ordinary skill in the art will recognize that factors such as temperature and shear rate may effect viscosity measurement. In a particular embodiment, viscosity of the is measured at 20° C.+/−1° C. using a Brookfield Cone and Plate Viscometer Model VDV-III Ultra+ with a CP40 or equivalent Spindle with a shear rate of approximately 22.50+/−approximately 10 (1/sec), or a Brookfield Viscometer Model LVDV-E with a SC4-18 or equivalent Spindle with a shear rate of approximately 26+/−approximately 10 (1/sec). In another embodiment, viscosity of the ophthalmic formulations of the invention is measured at 25° C.+/−1° C. using a Brookfield Cone and Plate Viscometer Model VDV-III Ultra+ with a CP40 or equivalent Spindle with a shear rate of approximately 22.50+/−approximately 10 (1/sec), or a Brookfield Viscometer Model LVDV-E with a SC4-18 or equivalent Spindle with a shear rate of approximately 26+/− approximately 10 (1/sec).

Tonicity Enhancers

Tonicity is adjusted if needed typically by tonicity enhancing agents. Such agents may, for example be of ionic and/or non-ionic type. Examples of ionic tonicity enhancers are alkali metal or earth metal halides, such as, for example, $CaCl_2$, KBr, KCl, LiCl, NaI, NaBr or NaCl, $Na_2SO_4$ or boric acid. Non-ionic tonicity enhancing agents are, for example, urea, glycerol, sorbitol, mannitol, propylene glycol, or dextrose. The aqueous solutions of the present invention are typically adjusted with tonicity agents to approximate the osmotic pressure of normal lachrymal fluids which is equivalent to a 0.9% solution of sodium chloride or a 2.5% solution of glycerol. An osmolality of about 225 to 400 mOsm/kg is preferred, more preferably 280 to 320 mOsm.

Solubilizing Agents

The topical formulation may additionally require the presence of a solubilizer, in particular if one or more of the ingredients tends to form a suspension or an emulsion. Suitable solubilizers include, for example, tyloxapol, fatty acid glycerol polyethylene glycol esters, fatty acid polyethylene glycol esters, polyethylene glycols, glycerol ethers, polysorbate 20, polysorbate 80 or mixtures of those compounds. In a preferred embodiment, the solubilizer is a reaction product of castor oil and ethylene oxide, for example the commercial products Cremophor EL® or Cremophor RH40®. Reaction products of castor oil and ethylene oxide have proved to be particularly good solubilizers that are tolerated extremely well by the eye. In another embodiment, the solubilizer is tyloxapol or a cyclodextrin. The concentration used depends especially on the concentration of the active ingredient. The amount added is typically sufficient to solubilize the active ingredient. For example, the concentration of the solubilizer is from 0.1 to 5000 times the concentration of the active ingredient. Preferably, the solubilizer is not a cyclodextrin compound (for example alpha-, beta- or gamma-cyclodextrin, e.g. alkylated, hydroxyalkylated, carboxyalkylated or alkyloxycarbonyl-alkylated derivatives, or mono- or diglycosyl-alpha-, beta- or gamma-cyclodextrin, mono- or dimaltosyl-alpha-, beta- or gamma-cyclodextrin or panosyl-cyclodextrin).

Examples of Formulations

In a preferred embodiment, the cetirizine formulation comprises cetirizine at 0.05% to 0.25% (w/v), glycerin at 0.1% to 5% (v/v) (e.g., 0.1% to 3% (v/v) or any specific value within said range), and water. In particular embodiments the cetirizine formulation of the invention does not contain a cyclodextrin or other solubilizing compound. Optionally, the formulation also comprises a preservative such as benzalkonium chloride at 0.005% to 0.02% (w/v) or its derivative (e.g., Polyquad®), or a stabilized oxychloro complex such as Purite®. In a particular embodiment, the cetirizine formulation comprises cetirizine at 0.1% (w/v), glycerin at 1.2% to 3% (v/v), and water. In another particular embodiment, the cetirizine 0.1% (w/v), glycerin 1.2% to 3% (v/v), and water formulation also comprises benzalkonium chloride at 0.01% (w/v) or a stabilized, oxychloro complex (e.g., Purite®). The pH of the formulation is between 5.0 and 7.5 for example, the pH of the formulation is 5, 5.5, 6.0, 6.5, 7.0, 7.2, 7.4 or 7.5.

In a preferred embodiment, the cetirizine formulation comprises cetirizine at 0.08% to 0.12% (w/v), glycerin at 0.1% to 5% (v/v) (e.g., 0.1% to 3% (v/v) or any specific value within said range), and water. In particular embodiments the cetirizine formulation of the invention does not contain a cyclodextrin or other solubilizing compound. Optionally, the formulation also comprises a preservative such as benzalkonium chloride at 0.005% to 0.02% (w/v) or its derivative (e.g., Polyquad®), or a stabilized oxychloro complex such as Purite®. In a particular embodiment, the cetirizine formulation comprises cetirizine at 0.1% (w/v), glycerin at 1.2% to 3% (v/v), and water. In another particular embodiment, the cetirizine 0.1% (w/v), glycerin 1.2% to 3% (v/v), and water formulation also comprises benzalkonium chloride at 0.01% (w/v) or a stabilized, oxychloro complex (e.g., Purite®). The pH of the formulation is between 5.0 and 7.5 for example, the pH of the formulation is 5, 5.5, 6.0, 6.5, 7.0, 7.2, 7.4 or 7.5.

In a specific embodiment, the cetirizine formulation comprises cetirizine at 0.1% (w/v), glycerin at 2.125% (v/v), benzalkonium chloride at 0.01% (w/v), q.s. with water. In one embodiment, the cetirizine formulation comprises cetirizine as the only active ingredient at 0.05% to 0.25% (w/v) and optionally one or more tear substitutes or a mucoadhesive, polymeric compound (e.g., Durasite®). Preferably, the cetirizine formulations do not contain a cyclodextrin or other solubilizing compound.

Where the formulation comprises one or more tear substitutes, the tear substitute preferably contains hydroxypropylmethyl cellulose or carboxymethyl cellulose or both. In some embodiments, the hydroxypropylmethyl cellulose or carboxymethyl cellulose is present at a concentration of 0.5% to 1% (w/v) (or any specific value within said range) and the resulting viscosity of the solution is 60-80 cpi. In a particular embodiment, the hydroxypropylmethyl cellulose or carboxymethyl cellulose is present at a concentration of 0.7% to 0.9%. In another particular embodiment, the hydroxypropylmethyl cellulose or carboxymethyl cellulose is present at a concentration of 0.1% to 0.7% and the resulting viscosity of the solution is 10-30 cpi. Optionally, the formulation also comprises a preservative, preferably benzalkonium chloride at a concentration of from 0.005% to 0.02% (w/v) (or any specific value within said range) or its derivative (e.g., Polyquad®), or a stabilized oxychloro complex (e.g., Purite®), or sodium perborate, or sorbate or sepazonium. The pH of the formulation is between 5.0 and 7.5. For example, the pH of the formulation is 5, 5.5, 6.0, 6.5, 7.0, 7.2, 7.4 or 7.5.

In another preferred embodiment, the cetirizine formulation comprises cetirizine at 0.05% to 0.25% (w/v), naphazoline at 0.01% to 0.2% (w/v), glycerin at 0.1% to 5% (v/v) (e.g., 0.1% to 3% (v/v) or any specific value within said range), and water. Preferably, the cetirizine/naphazoline formulation does not contain a cyclodextrin or other solubilizing compound. Optionally, the formulation also comprises benzalkonium chloride at 0.005% to 0.02% (w/v) or its derivative (e.g., Polyquad®), or a stabilized oxychloro complex such as Purite®. In a particular embodiment, the cetirizine formulation comprises cetirizine at 0.1% (w/v), naphazoline at 0.09% (w/v), glycerin at 1.2% to 3% (v/v), and water. In another particular embodiment, the cetirizine 0.1% (w/v), naphazoline 0.09% (w/v), glycerin at 1.2% to 3% (v/v), and water formulation also comprises benzalkonium chloride at 0.01% (w/v) or a stabilized oxychloro complex such as Purite®. The pH of the formulation is between 5.0 and 7.5. For example, the pH of the formulation is 5, 5.5, 6.0, 6.5, 7.0, 7.2, 7.4 or 7.5.

In yet another preferred embodiment, the cetirizine formulation comprises cetirizine at 0.05% to 0.25% (w/v), naphazoline at 0.01% to 0.2% (w/v), and one or more tear substitutes or a mucoadhesive polymeric compound (e.g., Durasite®). In particular embodiments the cetirizine formulation does not contain a cyclodextrin or other solubilizing compound. Where the formulation comprises one or more tear substitutes, the tear substitute preferably contains hydroxypropylmethyl cellulose or carboxymethyl cellulose, or both. In some embodiments, the hydroxypropylmethyl cellulose or carboxymethyl cellulose is present at a concentration of 0.5% to 1% (w/v) (or any specific value within said range) and the resulting viscosity of the solution is 60-80 cpi. In a particular embodiment, the hydroxypropylmethyl cellulose or carboxymethyl cellulose is present at a concentration of 0.7% to 0.9%. Optionally, the formulation also comprises a preservative, preferably benzalkonium chloride at a concentration of from 0.005% to 0.02% (w/v) (or any specific value within said range) or stabilised oxychloro complex (Purite®). The pH of the formulation is between 5.0 and 7.5. For example, the pH of the formulation is 5, 5.5, 6.0, 6.5, 7.0, 7.2, 7.4 or 7.5.

In yet another preferred embodiment, the cetirizine formulation comprises cetirizine at 0.05% to 0.25% (w/v), oxymetazoline at 0.01% to 0.1% (w/v), glycerin at 0.1% to 5% (v/v) (e.g., 0.1% to 3% (v/v) or any specific value within said range), and water. Preferably, the cetirizine/oxymetazoline formulation does not contain a cyclodextrin or other solubilizing compound. Optionally, the formulation also comprises benzalkonium chloride at 0.005% to 0.02% (w/v) or its derivative (e.g., Polyquad®), or a stabilized, oxychloro complex (e.g., Purite®). In a particular embodiment, the cetirizine formulation comprises cetirizine at 0.1% (w/v), oxymetazoline at 0.05% (w/v), glycerin at 1.2% to 3% (v/v), and water. In another particular embodiment, the cetirizine 0.1% (w/v), oxymetazoline 0.05% (w/v), glycerin 1.2% to 3% (v/v), and water formulation also comprises benzalkonium chloride at 0.01% (w/v) or a stabilized, oxychloro complex (e.g., Purite®). In certain embodiments, the pH of the formulation is between 5.0 and 7.5. For example, the pH of the formulation is 5, 5.5, 6.0, 6.5, 7.0, 7.2, 7.4 or 7.5.

In still another preferred embodiment, the cetirizine formulation comprises cetirizine at 0.05% to 0.25% (w/v), oxymetazoline at 0.01% to 0.1% (w/v), and one or more tear substitutes or a mucoadhesive, polymeric compound (e.g., Durasite®). Preferably, the cetirizine/oxymetazoline formulation does not contain a cyclodextrin or other solubilizing compound. Where the formulation comprises one or more tear substitutes, the tear substitute preferably contains hydroxypropylmethyl cellulose or carboxymethyl cellulose or both. In some embodiments, the hydroxypropylmethyl cellulose or carboxymethyl cellulose is present at a concentration of 0.5% to 1% (w/v) (or any specific value within said range) and the resulting viscosity of the solution is 60-80 cpi. In a particular embodiment, the hydroxypropylmethyl cellulose or carboxymethyl cellulose is present at a concentration of 0.7% to 0.9%. Optionally, the formulation also comprises a preservative, preferably benzalkonium chloride at a concentration of from 0.005% to 0.02% (w/v) (or any specific value within said range) or a stabilized oxychloro complex (Purite®). The pH of the formulation is between 5.0 and 7.5. For example, the pH of the formulation is 5, 5.5, 6.0, 6.5, 7.0, 7.2, 7.4 or 7.5.

In still another preferred embodiment, the cetirizine formulation comprises cetirizine at 0.05% to 0.5% (w/v), fluticasone at 0.001% to 1.0% (w/v), glycerin at 0.1% to 5% (v/v) (e.g., 0.1% to 3% (v/v) or any specific value within said range), and water. Preferably, the cetirizine/fluticasone formulation does not contain a cyclodextrin or other solubilizing compound. Optionally, the formulation also comprises benzalkonium chloride at 0.005% to 0.02% (w/v) or its derivative (e.g., Polyquad®), or a stabilized, oxychloro complex (e.g., Purite®). In a particular embodiment, the cetirizine formulation comprises cetirizine at 0.1% (w/v), fluticasone at 0.005%, glycerin at 1.2% to 3% (v/v), and water. In another particular embodiment, the cetirizine formulation comprises cetirizine at 0.25% (w/v), fluticasone at 0.01% (w/v), glycerin at 1.2% to 3% (v/v), and water. Optionally, the cetirizine/fluticasone formulations also comprises benzalkonium chloride at 0.01% (w/v) or a stabilized, oxychloro complex (e.g., Purite®). The pH of the formulation is between 5.0 and 7.5. For example, the pH of the formulation is 5, 5.5, 6.0, 6.5, 7.0, 7.2, 7.4 or 7.5.

In yet another preferred embodiment, the cetirizine formulation comprises cetirizine at 0.05% to 0.5% (w/v), fluticasone at 0.001% to 1.0% (w/v), preferably fluticasone 0.005%, and one or more tear substitutes or a mucoadhesive, polymeric compound (e.g., Durasite®). Preferably, the cetirizine/fluticasone formulation does not contain a cyclodextrin or other solubilizing compound. Where the formulation comprises one or more tear substitutes, the tear substitute preferably contains hydroxypropylmethyl cellulose or carboxymethyl cellulose or both. In some embodiments, the hydroxypropylmethyl cellulose or carboxymethyl cellulose is present at a concentration of 0.5% to 1% (w/v) (or any specific value within said range) and the resulting viscosity of the solution is 60-80 cpi. In a particular embodiment, the hydroxypropylmethyl cellulose or carboxymethyl cellulose is present at a concentration of 0.7% to 0.9%. Optionally, the formulation also comprises a preservative, preferably benzalkonium chloride at a concentration of from 0.005% to 0.02% (w/v) (or any specific value within said range) or stabilized oxychloro complex (Purite®). The pH of the formulation is between 5.0 and 7.5. For example, the pH of the formulation is 5, 5.5, 6.0, 6.5, 7.0, 7.2, 7.4 or 7.5.

In still another preferred embodiment, the cetirizine formulation comprises 0.1% cetirizine, 0.005% fluticasone, 1% Polyethylene Glycol 400, NF, 0.2% Dibasic Sodium Phosphate, Anhydrous, USP, 0.25% Hypromellose, USP, 0.1% Polysorbate 80, NF, 1.8% Glycerin, USP, 0.025% Edetate Disodium, USP, and 0.01% Benzalkonium Chloride, NF (pH 7.0).

In yet another preferred embodiment, the cetirizine formulation comprises 0.25% cetirizine, 0.01% fluticasone, 1% Polyethylene Glycol 400, NF, 0.2% Dibasic Sodium Phosphate, Anhydrous, USP, 0.25% Hypromellose, USP; 0.1% Polysorbate 80, NF, 1.2% Glycerin, USP, 0.025% Edetate Disodium, USP, and 0.01% Benzalkonium Chloride, NF (pH 7.0).

The formulations of the present invention provide for the chemical stability of the formulated cetirizine and other optional active agents (e.g., naphazoline, oxymetazoline, fluticasone, or combinations thereof) of the formulation, without the use of a cyclodextrin or other solubilizing compound. "Stability" and "stable" in this context refers to the resistance of the cetirizine and other optional active agents to chemical degradation under given manufacturing, preparation, transportation and storage conditions. The "stable" formulations of the invention also preferably retain at least 90%, 95%, 98%, 99%, or 99.5% of a starting or reference amount under given manufacturing, preparation, transportation, and/or storage conditions. The amount of cetirizine and other optional active agents can be determined using any art-recognized method, for example, as UV-Vis spectrophotometry and high pressure liquid chromatography (HPLC).

In certain embodiments, the cetirizine formulations are stable at temperatures ranging from about 20 to 30° C. for at least 1 week, at least 2 weeks, at least 3 weeks, at least 4 weeks, at least 5 weeks, at least 6 weeks, or at least 7 weeks. In other embodiments, the cetirizine formulations are stable at temperatures ranging from about 20 to 30° C. for at least 1 month, at least 2 months, at least 3 months, at least 4 months, at least 5 months, at least 6 months, at least 7 months, at least 8 months, at least 9 months, at least 10 months, at least 11 months, or at least 12 months. In one embodiment, the formulation is stable for at least 3 months at 20-25° C.

In other embodiments, the cetirizine formulations are stable at temperatures ranging from about 2 to 8° C. for at least 1 month, at least 2 months, at least 4 months, at least 6 months, at least 8 months, at least 10 months, at least 12 months, at least 14 months, at least 16 months, at least 18 months, at least 20 months, at least 22 months, or at least 24 months. In one embodiment, the formulation is stable for at least 2 months at 2 to 8° C.

In other embodiments, the cetirizine formulations are stable at temperatures of about −20° C. for at least 1 month, at least 2 months, at least 4 months, at least 6 months, at least 8 months, at least 10 months, at least 12 months, at least 14 months, at least 16 months, at least 18 months, at least 20 months, at least 22 months, or at least 24 months. In one embodiment, the formulation is stable for at least 6-12 months at −20° C.

In a particular embodiment, a cetirizine formulation of the invention is stable at temperatures of about 20-30° C. at concentrations up to 0.10% for at least 3 months. In another embodiment, the formulation is stable at temperatures from about 2-8° C. at concentrations up to 0.10% for at least 6 months.

Methods of Use

The cetirizine formulations of the invention are useful for the treatment and prevention of the signs and symptoms of both the acute phase and late phase inflammatory reactions, i.e. allergic disorders. The allergic disorder is against an airborne allergen. In particular embodiments the allergic disorder is a nasal allergy, an ocular allergy or both. More specifically, the cetirizine formulations of the invention are useful for the treatment and prevention of the signs and symptoms of both the acute phase and late phase inflammatory reactions (i.e., chronic, persistent or refractory) of allergic conjunctivitis, such as ocular itching, redness, chemosis, tearing, and eyelid swelling, as well as associated nasal symptoms with rhinitis and/or rhinoconjunctivitis, including nasal itching, congestion, rhinorrhea, sneezing, itchy palate, itchy ear. The formulations of the invention are also useful for the treatment and prevention of the signs and symptoms of allergic rhinoconjunctivitis, which may have both ocular and/or nasal signs and symptoms The invention provides methods of treating or preventing allergic conjunctivitis, rhinitis and/or allergic rhinoconjunctivitis in a subject in need thereof comprising topically administering to the eye surface of the subject an ophthalmic formulation comprising an effective amount of cetirizine. In certain embodiments, the administration of cetirizine to the eye of a subject in need of treatment or prevention of allergic conjunctivitis and/or rhinitis and/or rhinoconjunctivitis is also effective to mitigate or reduce one or more nasal symptoms. Topical administration of the ophthalmic formulations directly to the eye of a subject will significantly reduce nasal signs and symptoms via drainage from the ocular surface into the nasal cavity through the nasolacrimal duct (See e.g., Abelson et al., Clin. Ther. 25(3), 931-947 (2003); Spangler et al., Clin. Ther. 25(8), 2245-2267 (2003); and Crampton et al., Clin Ther. November; 24(11):1800-8 (2002). Surprisingly, significantly less active agent is required to treat the nasal symptoms when instilled through the eye of a subject as compared to administration through the nose of the subject. For example, each spray of Flonase® (commercially available nasal spray comprising fluticasone) delivers 0.5 milligrams of fluticasone to the nasal cavity to treat allergic rhinitis and allergic rhinoconjunctivitis. In contrast, one drop of a 0.005% fluticasone ophthalmic formulation (i.e., 2.5 micrograms in a 50 microliter drop) has been shown to significantly reduce nasal symptoms associated with ocular allergy when topically administered directly to the eye (see Example 2 herein) when dosed once daily (QD). As such, the methods of the present invention may be more effective than the currently available treatment options for nasal symptoms of allergic conjunctivitis and/or rhinitis and/or allergic rhinoconjunctivitis.

The subject is preferably a human, but may be another mammal, for example a dog, a cat, a horse, a rabbit, a mouse, a rat, or a non-human primate.

The formulations of the present invention contain an amount of cetirizine, and optionally one or more additional active ingredients (for example without limitation a vasoconstrictor such as naphazoline or oxymetazoline, or a steroid such as fluticasone), that is effective for the intended use (i.e., to mitigate the signs and symptoms of allergic conjunctivitis and/or rhinitis and/or rhinoconjunctivitis). In certain embodiments, surprisingly a concentration was identified with once a day administration of the formulations of the present invention to be effective to mitigate the symptoms of allergic conjunctivitis, rhinitis, and/or rhinoconjunctivitis, yet be low enough in concentration not to impact IOP significantly. However, particular dosages are also selected based on a number of factors including the age, sex, species and condition of the subject. Effective amounts can also be extrapolated from dose-response curves derived from in vitro test systems or from animal models. The term "effective amount" means an amount of cetirizine that is sufficient to eliminate or reduce a symptom of allergic conjunctivitis, rhinitis and/or rhinoconjunctivitis. In certain embodiments, the effective amount is the amount sufficient for the treatment or prevention of allergic conjunctivitis, rhinitis and/or rhinoconjunctivitis. "Treatment" in this context refers to reducing or ameliorating at least one symptom of allergic conjunctivitis and/or rhinitis and/or rhinoconjunctivitis. "Prevention" in this context refers to a reduction in the frequency of, or a delay in the onset of, symptoms associated with allergic conjunctivitis, rhinitis and/or rhinoconjunctivitis, relative to a subject who does not receive the composition. The effective amount of cetirizine and other active agents in the formulation will depend on absorption, inactivation, and excretion rates of the drug as well as the delivery rate of the compound from the formulation. Particular dosages may also vary with the severity of the condition to be alleviated. It is to be further understood that for any particular subject, specific dosage regimens should be adjusted over time according to the individual need and the professional judgment of the person administering or supervising the administration of the compositions. Typically, a dosing regiment will be determined using techniques known to one skilled in the art.

Examples of dosing regimens that can be used in the methods of the invention include, but are not limited to, once daily, twice daily, three times, and four times daily, or as-needed (PRN) for intermittent use. In certain embodiments, the method comprises administering a cetirizine formulation of the invention to the eye of the subject once a day. In some embodiments, the administration is 2 to 4 times a day.

In certain embodiments, the cetirizine formulations including the combination of cetirizine/fluticasone is useful when applied to the eye to treat nasal symptoms of patients with blocked nasal passages.

In certain embodiments, once a day administration (q.d.) is effective to mitigate the symptoms of ocular and/or nasal allergy. However, particular dosages may also be selected based on a number of factors including the age, sex, species and condition of the subject. Effective amounts can also be extrapolated from dose-response curves derived from in vitro test systems or from animal models.

The combined use of several active agents formulated into the compositions of the present invention may reduce the required dosage for any individual component because the onset and duration of effect of the different components may be complimentary. In such combined therapy, the different active agents may be delivered together or separately, and simultaneously or at different times within the day.

In a particular embodiment, a formulation comprising cetirizine as the only active agent in the formulation is administered to the eye of a subject in need of treatment or prevention of an allergic conjunctivitis, rhinitis and/or rhinoconjunctivitis once daily (q.d.). In certain embodiments, the combination formulation is administered two to four times a day.

In another particular embodiment, cetirizine is formulated with one or more of naphazoline, oxymetazoline or fluticasone, and administered to the eye of a subject in need of treatment or prevention of allergic conjunctivitis and/or rhinoconjunctivitis once daily (q.d.). In certain embodiments, the combination formulation is administered two to four times a day.

In a preferred embodiment, cetirizine is formulated with fluticasone and administered to the eyed of a subject in need of treatment or prevention of allergic conjunctivitis, rhinitis and/or rhinoconjunctivitis. Surprisingly the combination formulations of cetirizine and fluticasone as described herein were more effective at relieving itching than could be predicted from the efficacy of each component individually. Even more surprising was the finding that lower doses of cetirizine and fluticasone were more effective at relieving ocular itching and associated nasal symptoms of allergic conjunctivitis than higher doses of the individual components alone, or in combination. For example, as described in the Examples, a 0.1% cetirizine/0.005% fluticasone formulation (low dose) was more efficacious than 0.25% cetirizine/0.01% fluticasone formulation (high dose). Similarly, in a clinical study described herein, the efficacy of 0.005% fluticasone was more efficacious than the higher dose 0.01% fluticasone.

Packaging

The formulations of the present invention may be packaged as either a single dose product or a multi-dose product. The single dose product is sterile prior to opening of the package and all of the composition in the package is intended to be consumed in a single application to one or both eyes of a patient. The use of an antimicrobial preservative to maintain the sterility of the composition after the package is opened is generally unnecessary.

Multi-dose products are also sterile prior to opening of the package. However, because the container for the composition may be opened many times before all of the composition in the container is consumed, the multi-dose products must have sufficient antimicrobial activity to ensure that the compositions will not become contaminated by microbes as a result of the repeated opening and handling of the container. The level of antimicrobial activity required for this purpose is well known to those skilled in the art, and is specified in official publications, such as the United States Pharmacopoeia ("USP") and corresponding publications in other countries. Detailed descriptions of the specifications for preservation of ophthalmic pharmaceutical products against microbial contamination and the procedures for evaluating the preservative efficacy of specific formulations are provided in those publications. In the United States, preservative efficacy standards are generally referred to as the "USP PET" requirements. (The acronym "PET" stands for "preservative efficacy testing.")

The use of a single dose packaging arrangement eliminates the need for an antimicrobial preservative in the compositions, which is a significant advantage from a medical perspective in some cases, because conventional antimicrobial agents utilized to preserve ophthalmic compositions (e.g., benzalkonium chloride) may cause ocular irritation, particularly in patients suffering from dry eye conditions, having a compromised ocular surface, using multiple preserved drops per day, or have pre-existing ocular irritation. However, the single dose packaging arrangements currently available, such as small volume plastic vials prepared by means of a process known as "form, fill and seal", have several disadvantages for manufacturers and consumers. The principal disadvantages of the single dose packaging systems are the much larger quantities of packaging materials required, which is both wasteful and costly, and the inconvenience for the consumer. Also, there is a risk that consumers will not discard the single dose containers following application of one or two drops to the eyes, as they are instructed to do, but instead will save the opened container and any composition remaining therein for later use. This improper use of single dose products creates a risk of microbial contamination of the single dose product and an associated risk of ocular infection if a contaminated composition is applied to the eyes.

While the formulations of this invention are preferably formulated as "ready for use" aqueous solutions, alternative formulations are contemplated within the scope of this invention. Thus, for example, the active ingredients, surfactants, salts, chelating agents, or other components of the ophthalmic solution, or mixtures thereof, can be lyophilized or otherwise provided as a dried powder or tablet ready for dissolution (e.g., in deionized, or distilled) water.

Kits

The present invention provides a pharmaceutical pack or kit comprising one or more containers filled with a liquid or lyophilized cetirizine formulation of the invention (i.e., a formulation comprising cetirizine alone or in combination with an additional active agent as described herein). In one embodiment, the formulation is an aqueous formulation of cetirizine. In one embodiment, the formulation is lyophilized. In preferred embodiments the liquid or lyophilized formulation is sterile. In one embodiment, the kit comprises a liquid or lyophilized formulation of the invention, in one or more containers, and one or more other prophylactic or therapeutic agents (e.g., cetirizine in combination with an additional active agent such as fluticasone, oxymetazoline or naphazoline) useful for the treatment of allergic conjunctivitis and/or allergic rhinoconjunctivitis. The one or more other prophylactic or therapeutic agents may be in the same container as the cetirizine or in one or more other containers. Preferably, the cetirizine is formulated at a concentration of from about 0.05% (w/v) to about 1.0% (w/v) and is suitable for topical ocular administration. In certain embodiments, cetirizine is formulated with an additional active agents such as fluticasone, oxymetazoline or naphazoline, as described herein. In certain embodiments, the kit contains the cetirizine in unit dosage form.

In certain embodiments, the kit further comprises instructions for use in the treatment of allergic conjunctivitis and/or allergic rhinoconjunctivitis (e.g., using the cetirizine formulations of the invention alone or in combination with another prophylactic or therapeutic agent), as well as side effects and dosage information for one or more routes of administration. Optionally associated with such container(s) is a notice in the form prescribed by a governmental agency regulating the manufacture, use or sale of pharmaceuticals or biological products, which notice reflects approval by the agency of manufacture, use or sale for human administration. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g. CD ROM), and the like. Such media may include addresses to internet sites that provide such instructional materials.

In another embodiment, this invention provides kits for the packaging and/or storage and/or use of the formulations described herein, as well as kits for the practice of the methods described herein. The kits can be designed to facilitate one or more aspects of shipping, use, and storage.

All publications and patents mentioned herein are hereby incorporated by reference in their entirety as if each individual publication or patent was specifically and individually indicated to be incorporated by reference.

EXAMPLES

The invention is further defined by reference to the following examples, which are not meant to limit the scope of the present invention. It will be apparent to those skilled in the art that many modifications, both to the materials and methods, may be practiced without departing from the purpose and interest of the invention.

Example 1

Figure 1B:
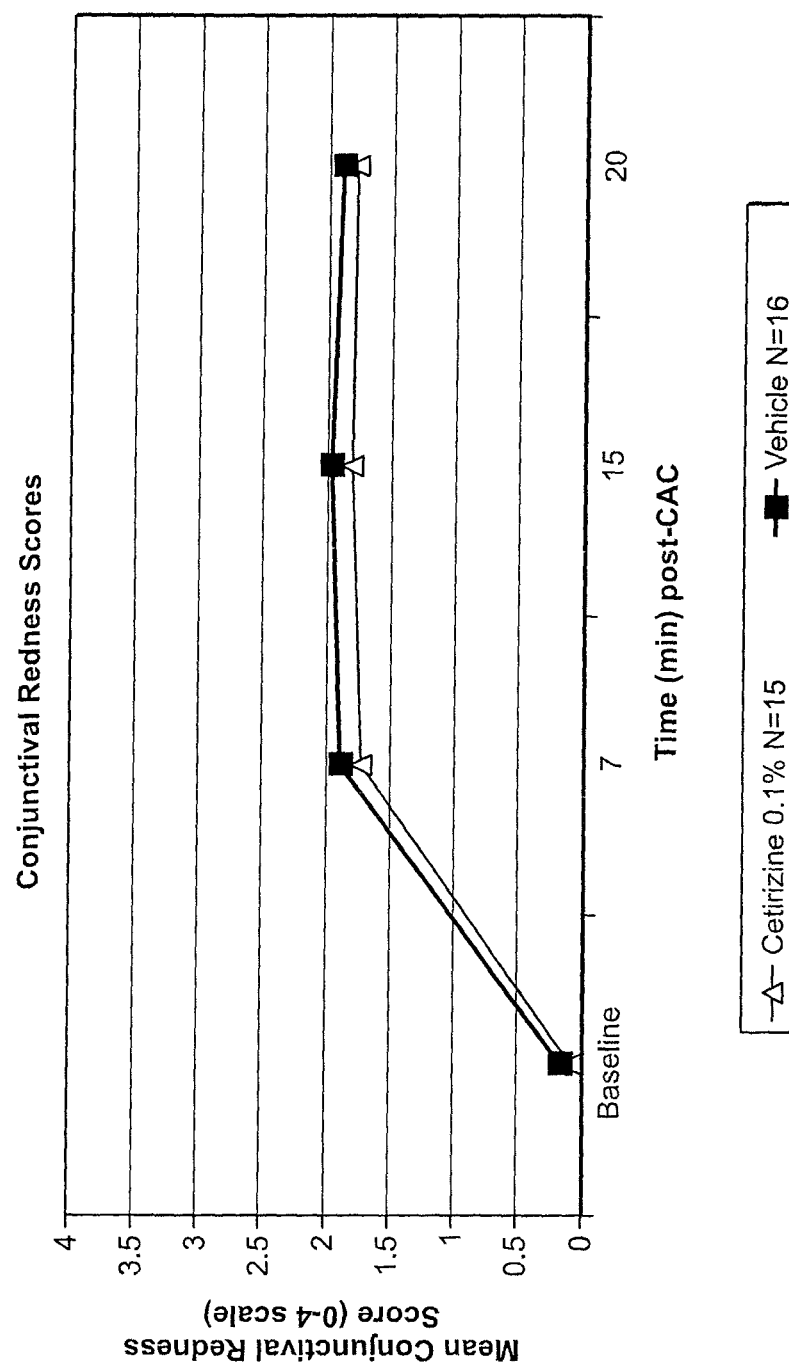
FIG. 1B is a line graph depicting the efficacy of a 0.1% cetirizine formulation reducing conjunctival redness as compared to a vehicle control
Figure 2:
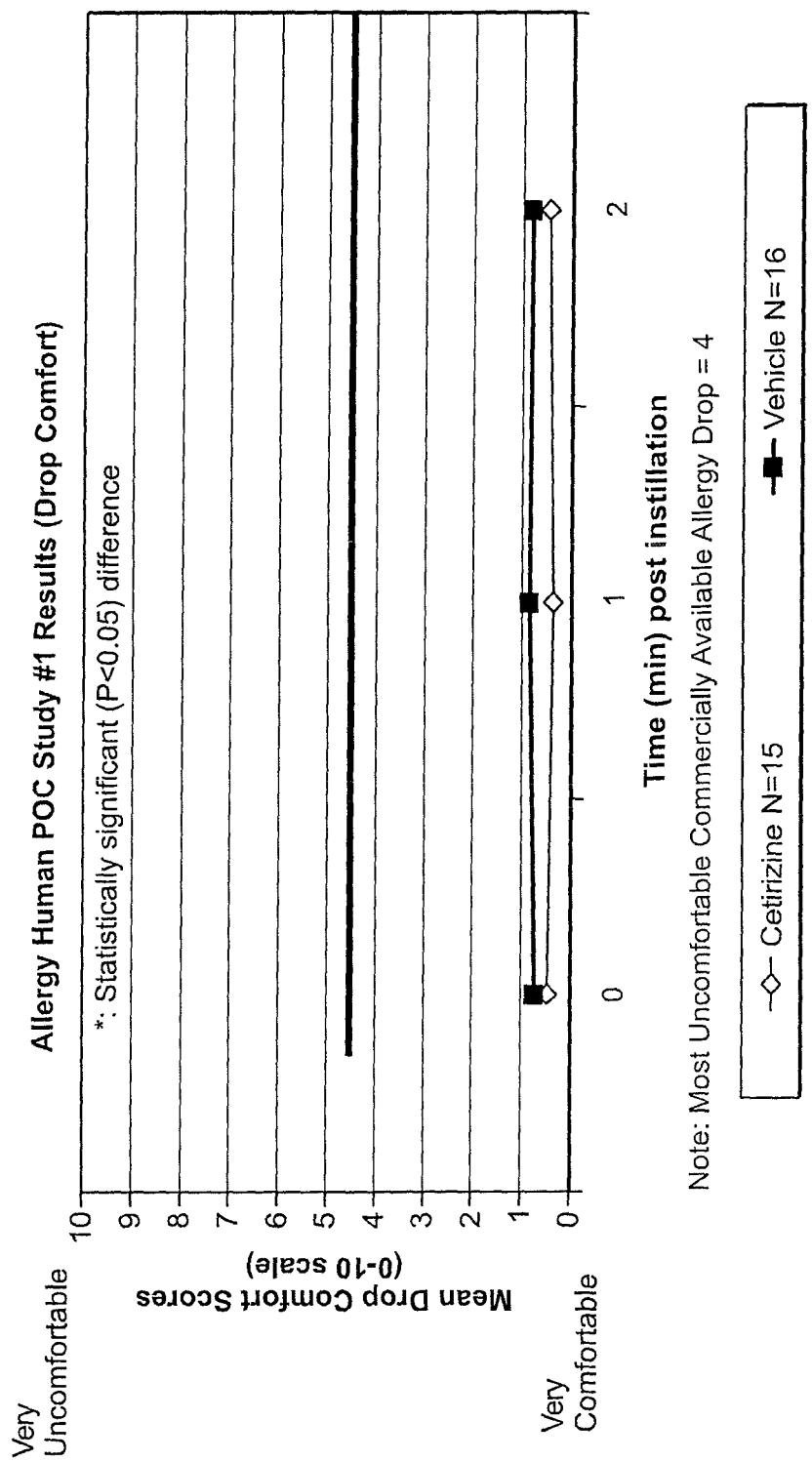
FIG. 2 is a line graph depicting the comfort profile of a 0.1% cetirizine formulation upon instillation in the eye as compared to a vehicle control. The comfort of the formulation is indicated on a subjective scale of 0 to 10 (0=very comfortable; >4=uncomfortable; 10=very uncomfortable). The mean drop comfort score is shown at 0, 1, 2 minutes after addition of a drop of the cetirizine formulation of the invention.

Cetirizine (0.1%) Prevents Ocular Itching Associated with Allergic Conjunctivitis A placebo controlled, double-blind study was conducted to evaluate the efficacy of cetirizine 0.1% (N=15) compared to vehicle (N=16). Subjects underwent 2 screening visits (an allergen titration and confirmation) followed by a drug evaluation visit. At the drug evaluation visit, one drop of masked study medication was instilled in each eye and comfort assessments were taken. Sixteen hours later the subjects were challenged with allergen and allergic assessments were taken. The results are presented in Tables 1 and 2 and in FIGS. 1-2. The ocular itching score ranges from 0, no itching, to 4, severe itching. The comfort score ranges from 0, very comfortable, to 10, very uncomfortable (Note: The most uncomfortable commercially available allergy drop=4). The results demonstrate that a single drop of cetirizine (0.1%) ophthalmic solution (q.d.) was effective to prevent ocular itching associated with allergic conjunctivitis when administered 16 hours prior to conjunctival allergen challenge (CAC), but had little effect on reducing conjunctival redness (FIGS. 1A and 1B). Differences between cetirizine and vehicle groups were both clinically (≥1 unit difference) and statistically significant ($P<0.05$). In addition, as shown in Table 2, and FIG. 2, the cetirizine formulation was comfortable (i.e., well-tolerated) by the subjects.

TABLE 1

Mean Ocular Itching Scores (0-4 scale) following CAC 16 hrs after dosing

| Statistic | Timepoint | Cetirizine 0.1% HCl (N = 15) | Vehicle (N = 16) | Mean Difference (cetirizine − vehicle) | p-value |
|---|---|---|---|---|---|
| Mean (SD) | Pre-CAC | 0.00 (0.00) | 0.00 (0.00) | 0.00 | 1.0000 |
| | 3 min | 1.67 (1.12) | 2.36 (0.58) | −0.69 | 0.0191 |
| | 5 min | 1.52 (1.12) | 2.56 (0.60) | −1.04 | 0.0051 |
| | 7 min | 1.45 (1.02) | 2.47 (0.72) | −1.02 | 0.0031 |

TABLE 2

Mean Drop Comfort Scores (0-10 scale)

| Statistic | Timepoint | Cetirizine 0.1% HCl (N = 15) | Vehicle (N = 16) | Mean Difference (cetirizine − vehicle) | p-value |
|---|---|---|---|---|---|
| Mean (SD) | Upon Instillation | 0.47 (0.68) | 0.72 (1.49) | −0.25 | 0.3908 |
| | 1 min | 0.37 (0.49) | 0.84 (1.80) | −0.47 | 0.1572 |
| | 2 min | 0.47 (0.63) | 0.81 (1.53) | −0.34 | 0.2467 |
| | 5 min | 0.20 (0.41) | 0.13 (0.34) | 0.07 | 0.5981 |
| | 10 min | 0.27 (0.46) | 0.31 (0.70) | −0.04 | 0.7864 |

Example 2

Figure 3A:
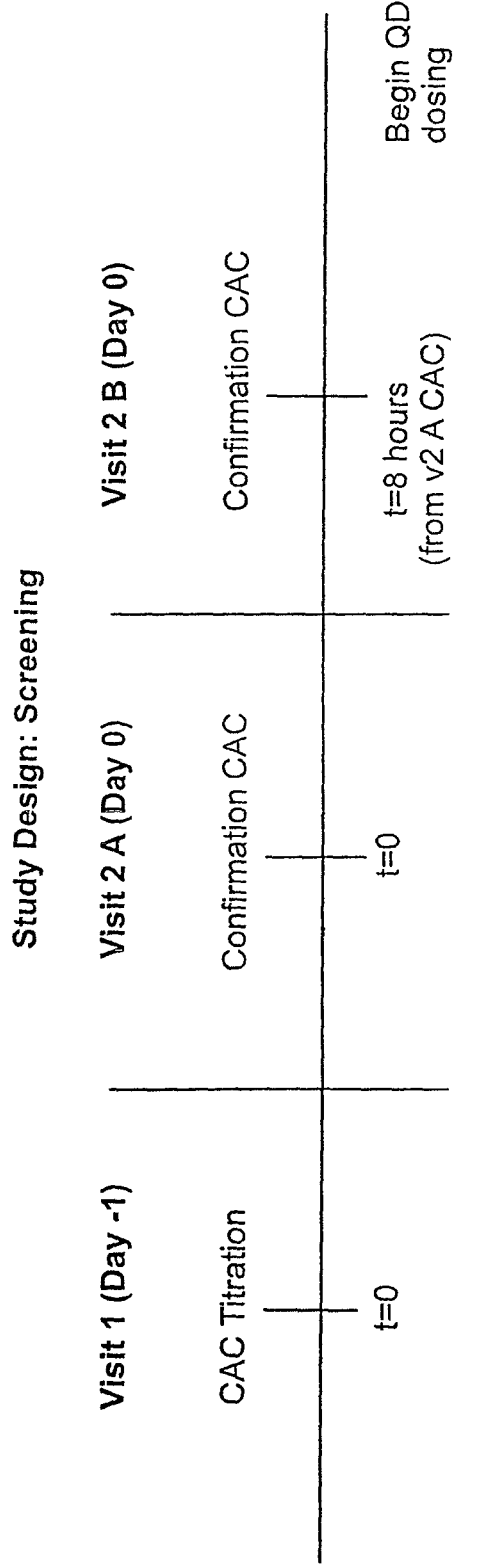
FIGS. 3A and 3B depict a study design (screening and evaluation) for testing the efficacy of Fluticasone 0.001%, 0.005% and 0.01% as compared to vehicle in reducing ocular and nasal symptoms of ocular allergy in an allergic conjunctivitis model.
Figure 3B:
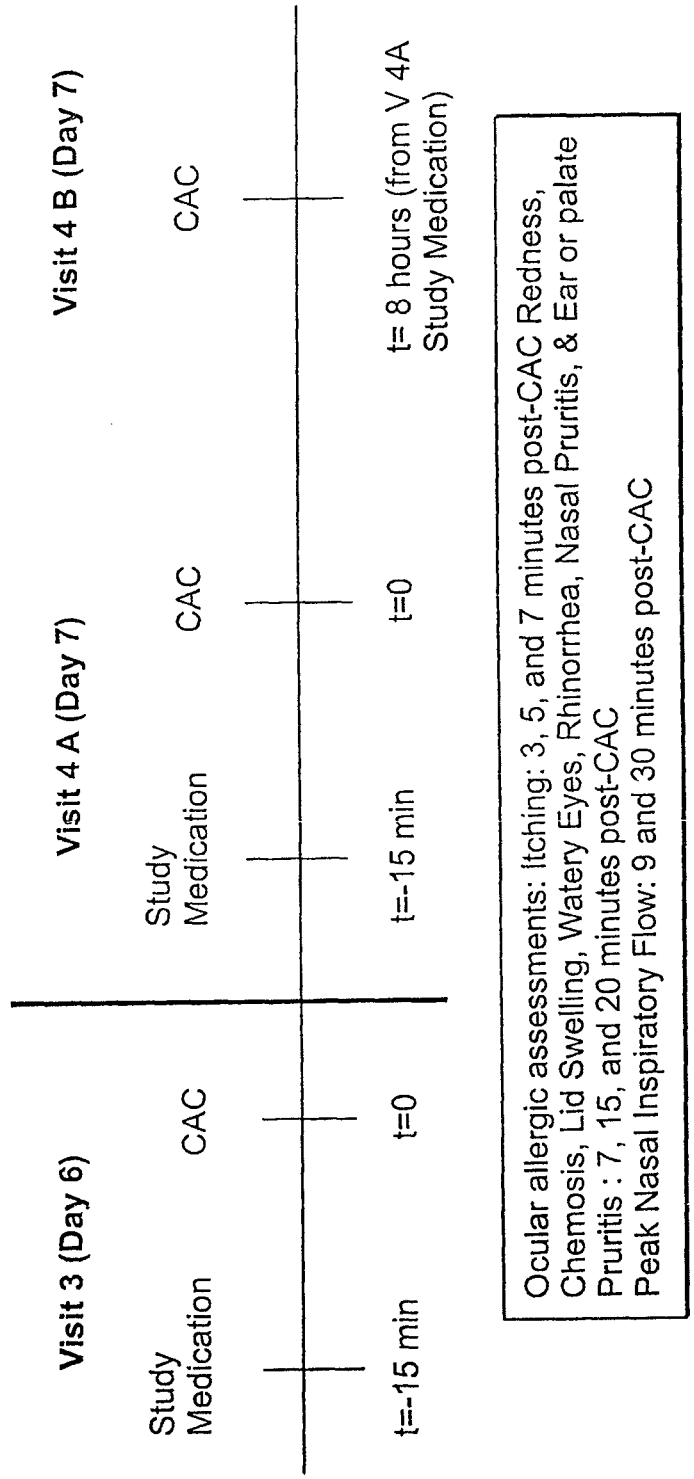

Fluticasone Prevents Ocular and Nasal Symptoms Associated with Allergic Conjunctivitis, Rhinitis and Rhinoconjunctivitis A placebo controlled, double-blind study was conducted to evaluate the efficacy of Fluticasone 0.001% (N=16), Fluticasone 0.005% (N=16), Fluticasone 0.01% (N=15) compared to vehicle alone (N=15). Subjects underwent 2 screening visits (allergen titration and confirmation) followed by 2 drug evaluation visits, as indicated in the study design shown in FIGS. 3A and 3B. At the drug evaluation visits, one drop of masked study medication was instilled in each eye and ocular allergic assessments were taken. Eight hours later the subjects were challenged with allergen and primary and secondary ocular and nasal endpoints were assessed, as well as safety of the formulations. The results are presented in FIGS. 4-23.

Primary Ocular Endpoints

Ocular itching, conjunctival redness, lid swelling, and nasal congestion were assessed in each subject during visit 4B.

Ocular itching was subjectively assessed on a scale of 0 (no itching) to 4 (severe itching). As shown in FIG. 4, Fluticasone 0.001%, 0.005% and 0.01% were about equally effective in reducing ocular itching over a 7 minute time period as compared to vehicle alone.

Figure 5:
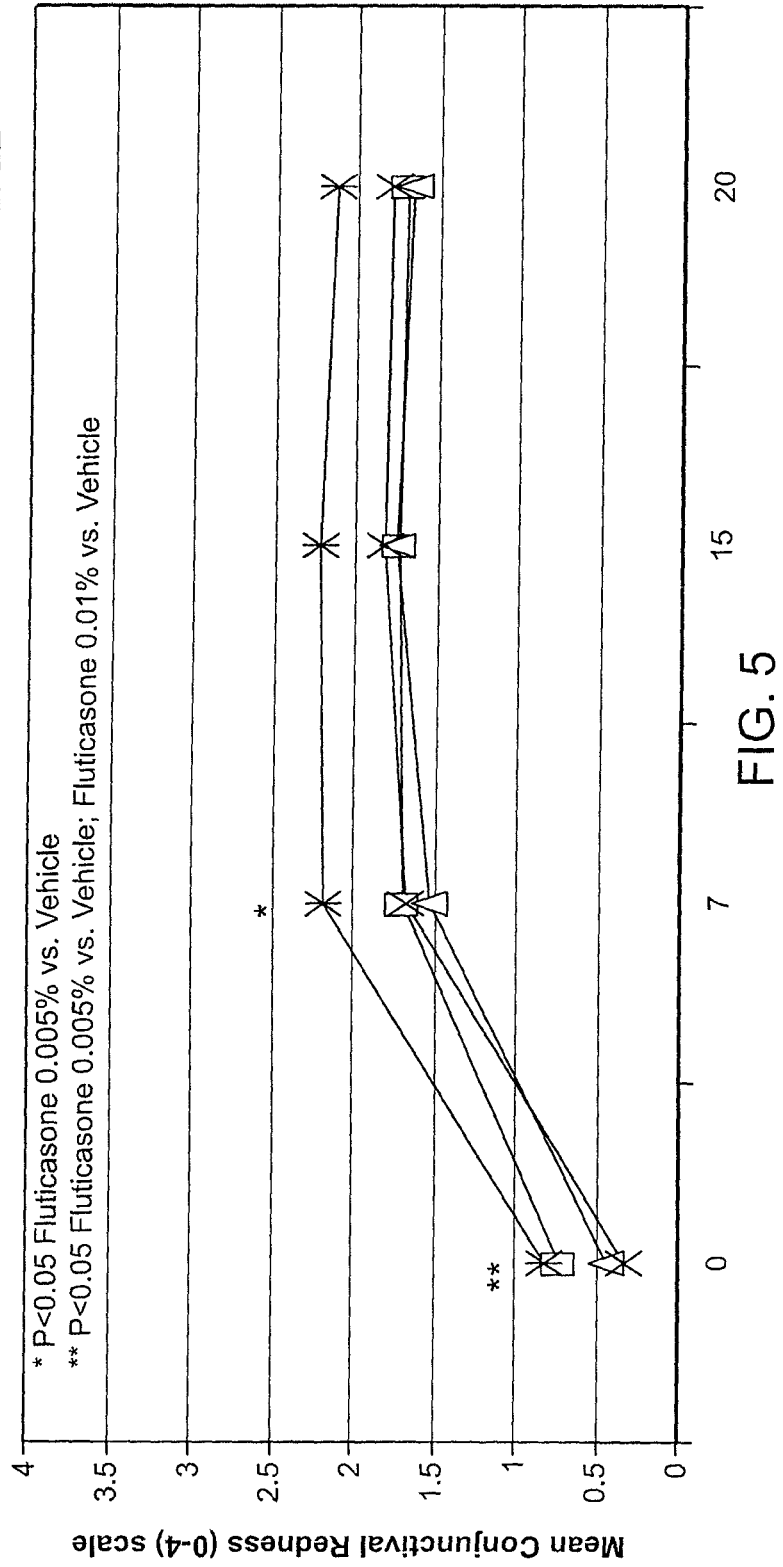
FIG. 5 is a line graph comparing the efficacy of Fluticasone 0.001%, 0.005% and 0.01% as compared to vehicle in reducing conjunctival redness, assessed on a scale of 0 (no redness) to 4 (severe redness) over time.

Conjunctival redness was also subjectively assessed on a scale of 0 (no redness) to 4 (severe redness). As shown in FIG. 5, Fluticasone 0.001%, 0.005% and 0.01% were about equally effective in reducing conjunctival redness over a 20 minute period as compared to vehicle alone.

Figure 6:
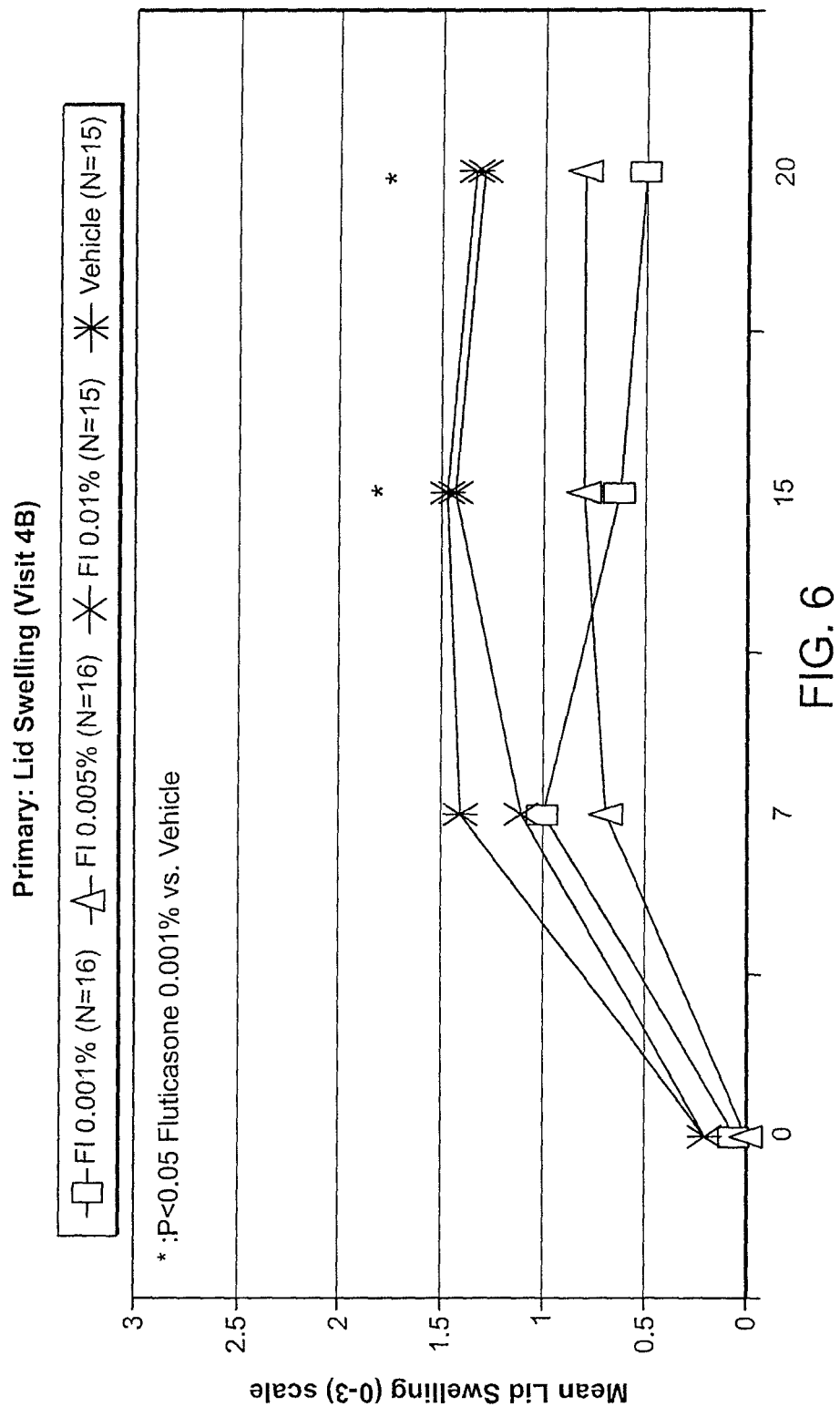
FIG. 6 is line graph comparing the efficacy of Fluticasone 0.001%, 0.005% and 0.01% as compared to vehicle in reducing lidswelling, assessed on a scale of 0 (no swelling) to 3 (severe swelling) over time.

Lid swelling was subjectively assessed on a scale of 0 (no lid swelling) to 3 (severe lid swelling). As shown in FIG. 6, Fluticasone 0.001% and 0.005% were each more effective than Fluticasone 0.01% at reducing lid swelling over a 20 minute period as compared to vehicle alone.

Figure 7:
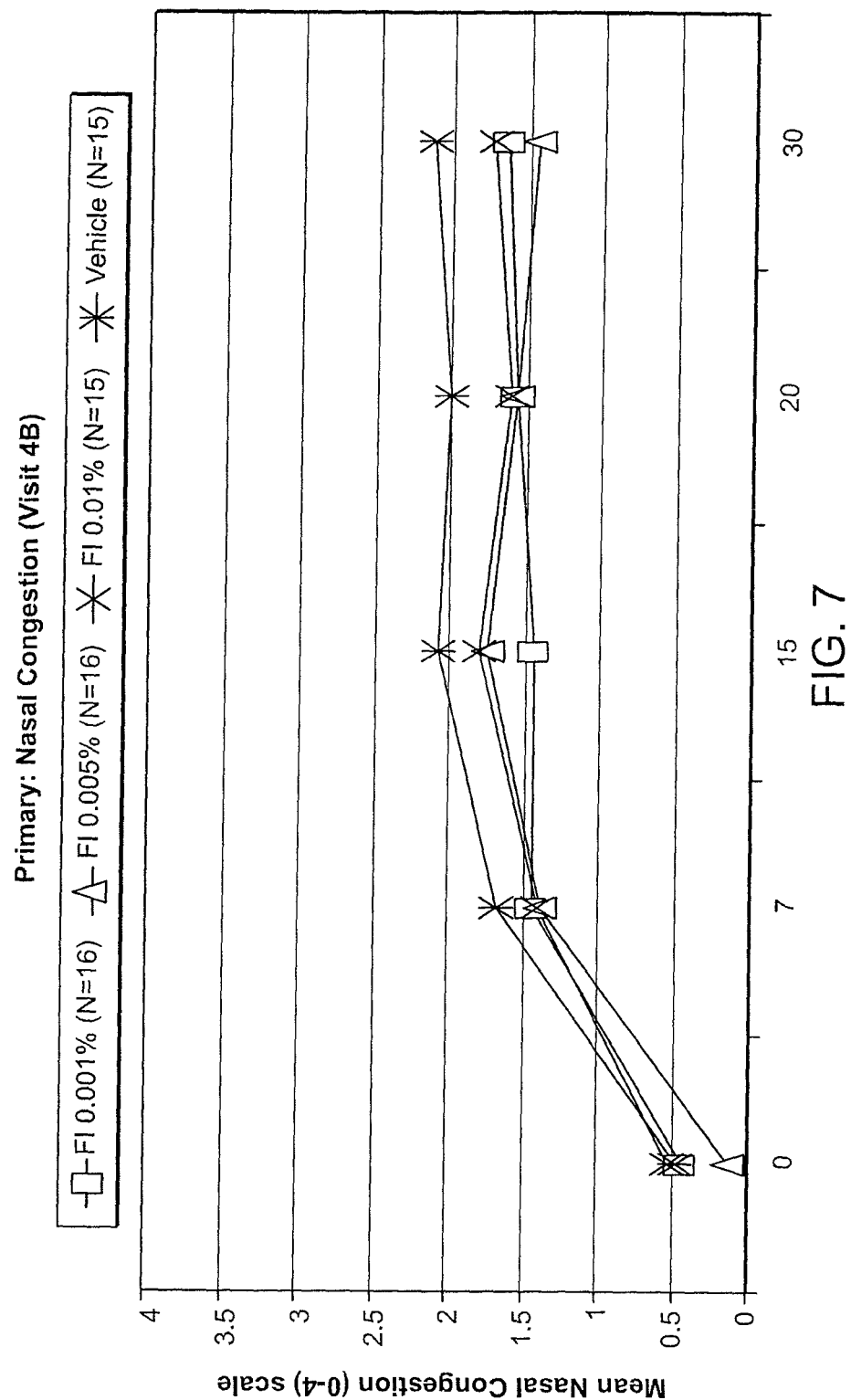
FIG. 7 is a line graph comparing the efficacy of Fluticasone 0.001%, 0.005% and 0.01% as compared to vehicle in reducing nasal congestion, assessed on a scale of 0 (no congestion) to 4 (severe congestion) over time.

Nasal Congestion was subjectively assessed on a scale of 0 (no congestion) to 4 (severe congestion). As shown in FIG. 7, Fluticasone 0.001%, 0.005% and 0.01% were about equally effective in reducing nasal congestion over a 30 minute period as compared to vehicle alone.

Figure 8:
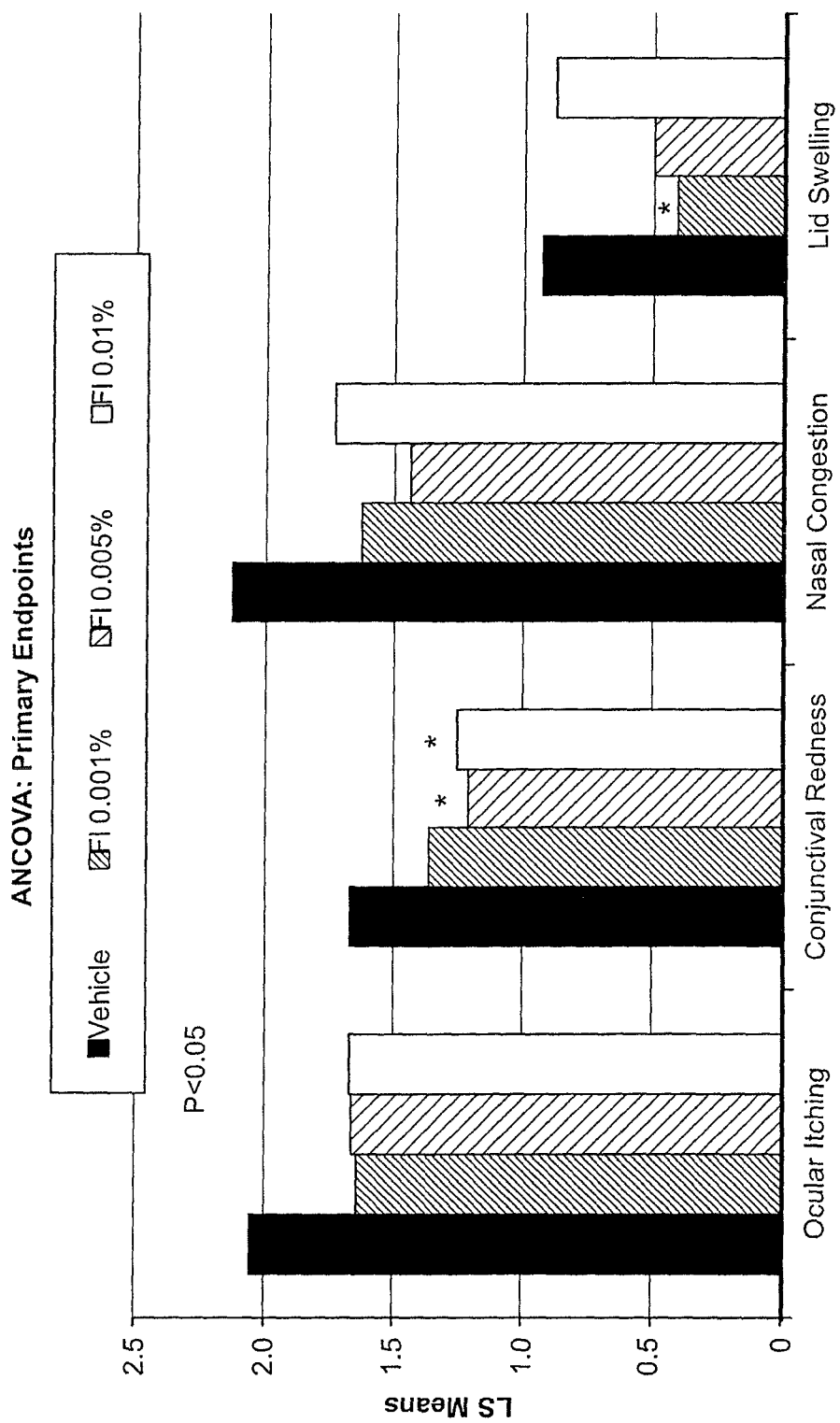
FIG. 8 is a bar graph summarizing the results shown in FIGS. 3-7.

A summary of the results of the primary ocular endpoint assessments is shown in FIG. 8. As shown in FIG. 8, the reduction in conjunctival redness by Fluticasone 0.005% and 0.01% and the reduction in lid swelling by Fluticasone 0.001% were each statistically significant ($p<0.05$).

Secondary Ocular Endpoints

Ciliary Redness, episcleral redness, chemosis and watery eyes were assessed in each subject at visit 4B.

Figure 9:
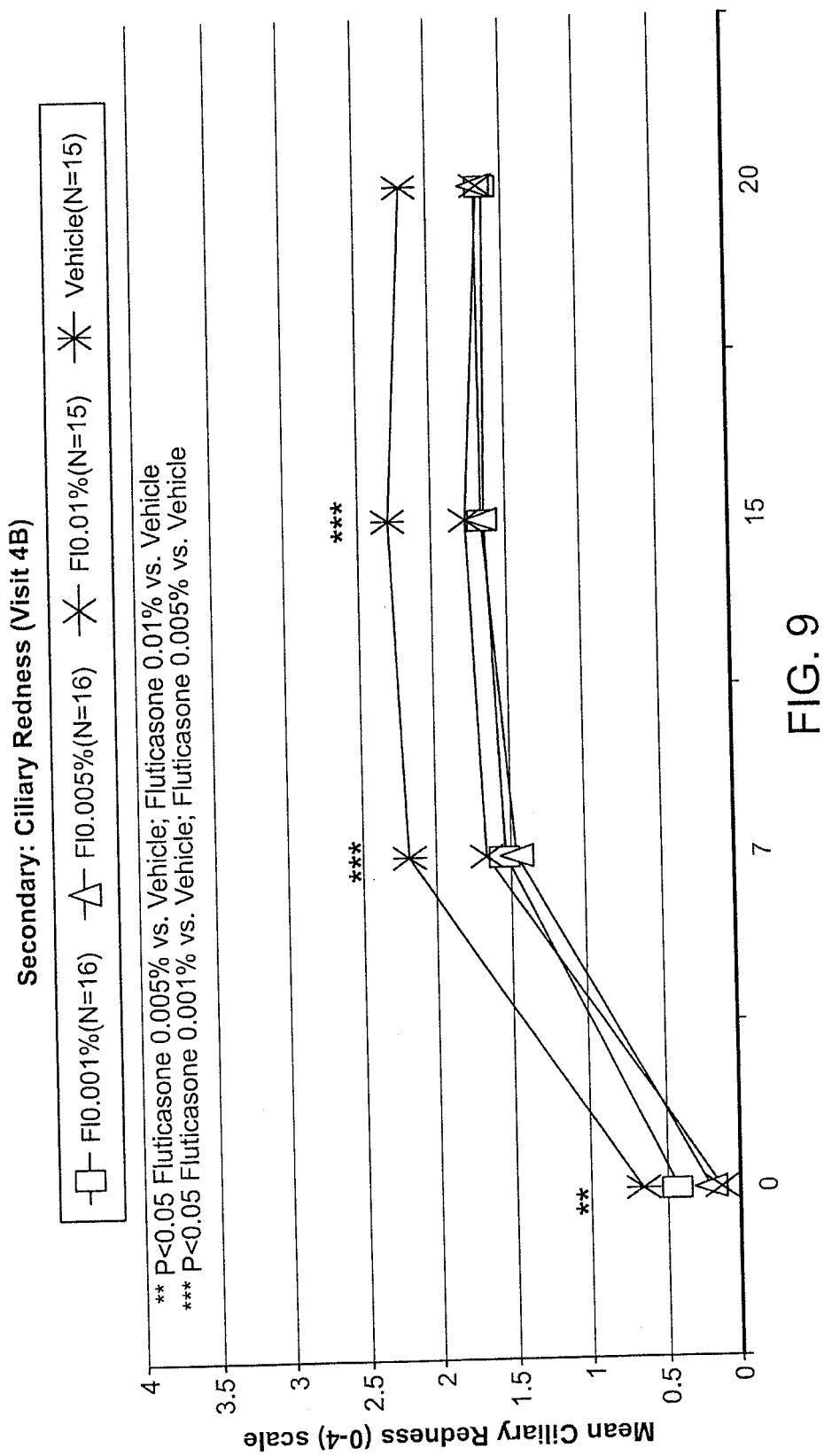
FIG. 9 is a line graph comparing the efficacy of Fluticasone 0.001%, 0.005% and 0.01% as compared to vehicle in reducing ciliary redness, assessed on a scale of 0 (no redness) to 4 (severe redness) over time.

Ciliary redness was assessed on a scale of 0 (no redness) to 4 (severe redness). As shown in FIG. 9, Fluticasone 0.001%, 0.005% and 0.01% were each significantly effective in reducing ciliary redness over a 20 minute period as compared to vehicle alone ($p<0.05$ for each Fluticasone concentration).

Figure 10:
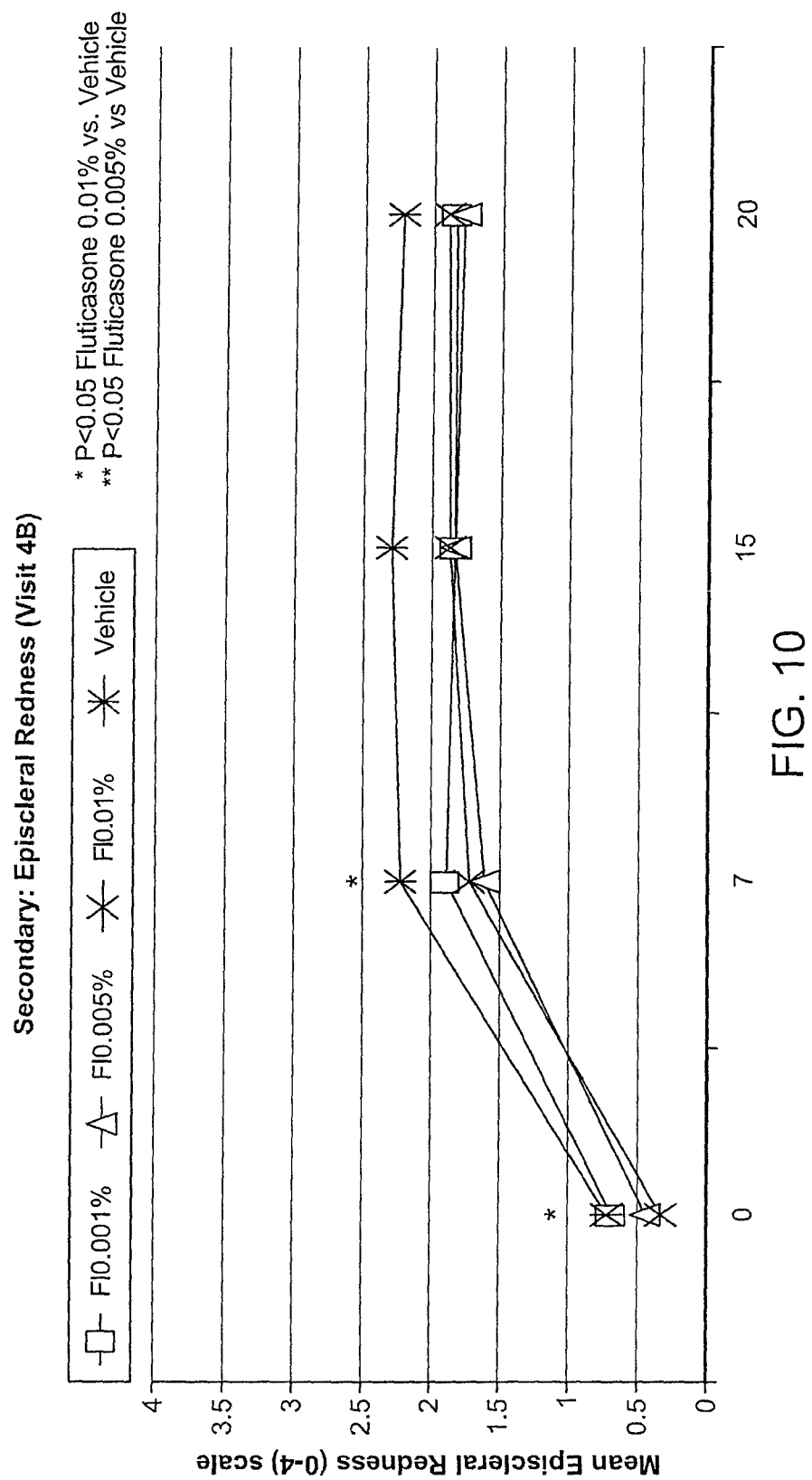
FIG. 10 is a line graph comparing the efficacy of Fluticasone 0.001%, 0.005% and 0.01% as compared to vehicle in reducing episcleral redness, assessed on a scale of 0 (no redness) to 4 (severe redness) over time.

Episcleral redness was assessed on a scale of 0 (no redness) to 4 (severe redness). As shown in FIG. 10, Fluticasone 0.001%, 0.005% and 0.01% each reduce episcleral redness over a 20 minute period as compared to vehicle alone.

Figure 11:
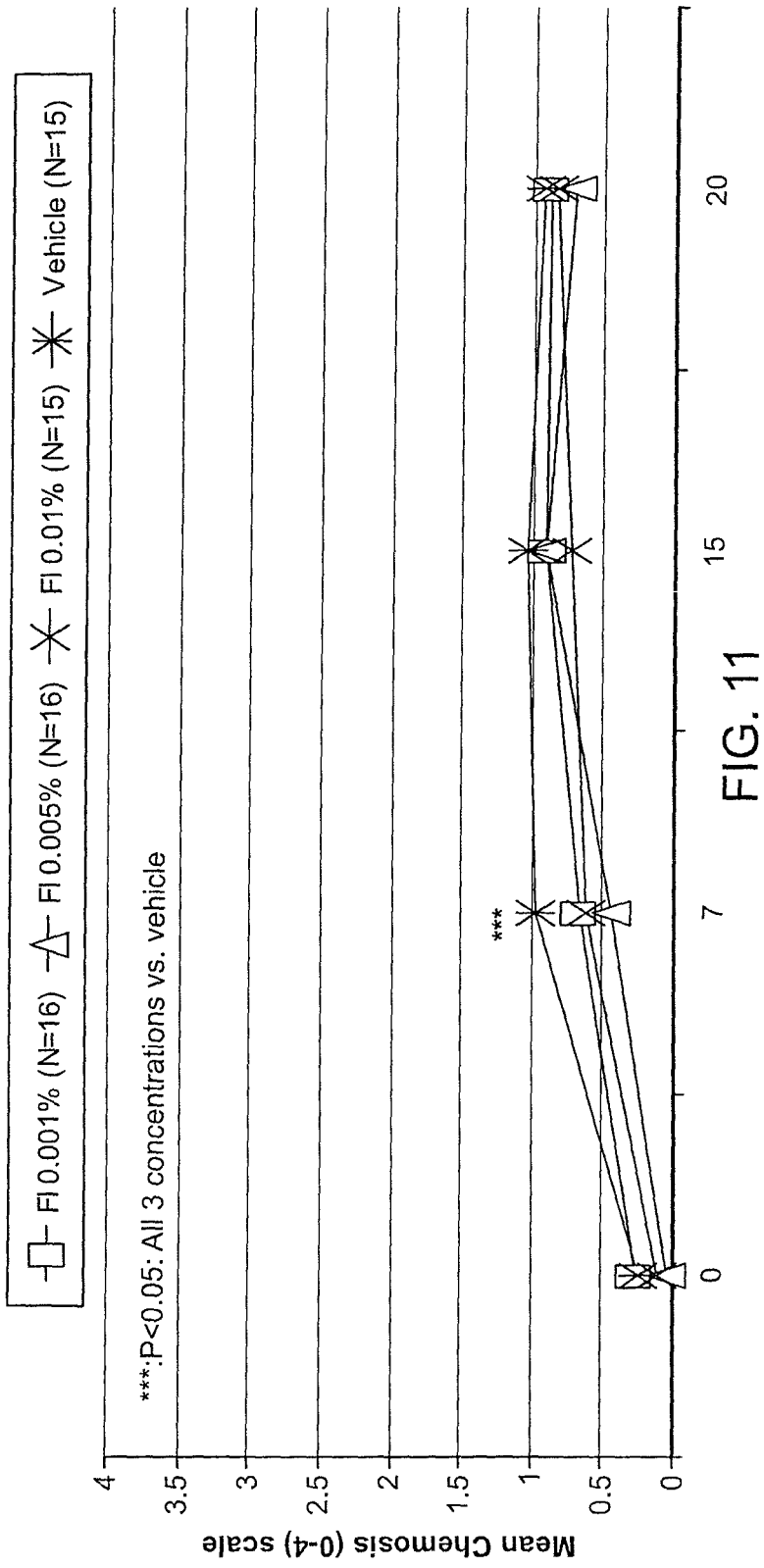
FIG. 11 is a line graph comparing the efficacy of Fluticasone 0.001%, 0.005% and 0.01% as compared to vehicle in reducing chemosis, assessed on a scale of 0 (none) to 4 (severe) over time.

Chemosis was assessed on a scale of 0 (none) to 4 (extreme). As shown in FIG. 11, Fluticasone 0.001%, 0.005% and 0.01% were each significantly effective in reducing chemosis over a 20 minute period.

Figure 12:
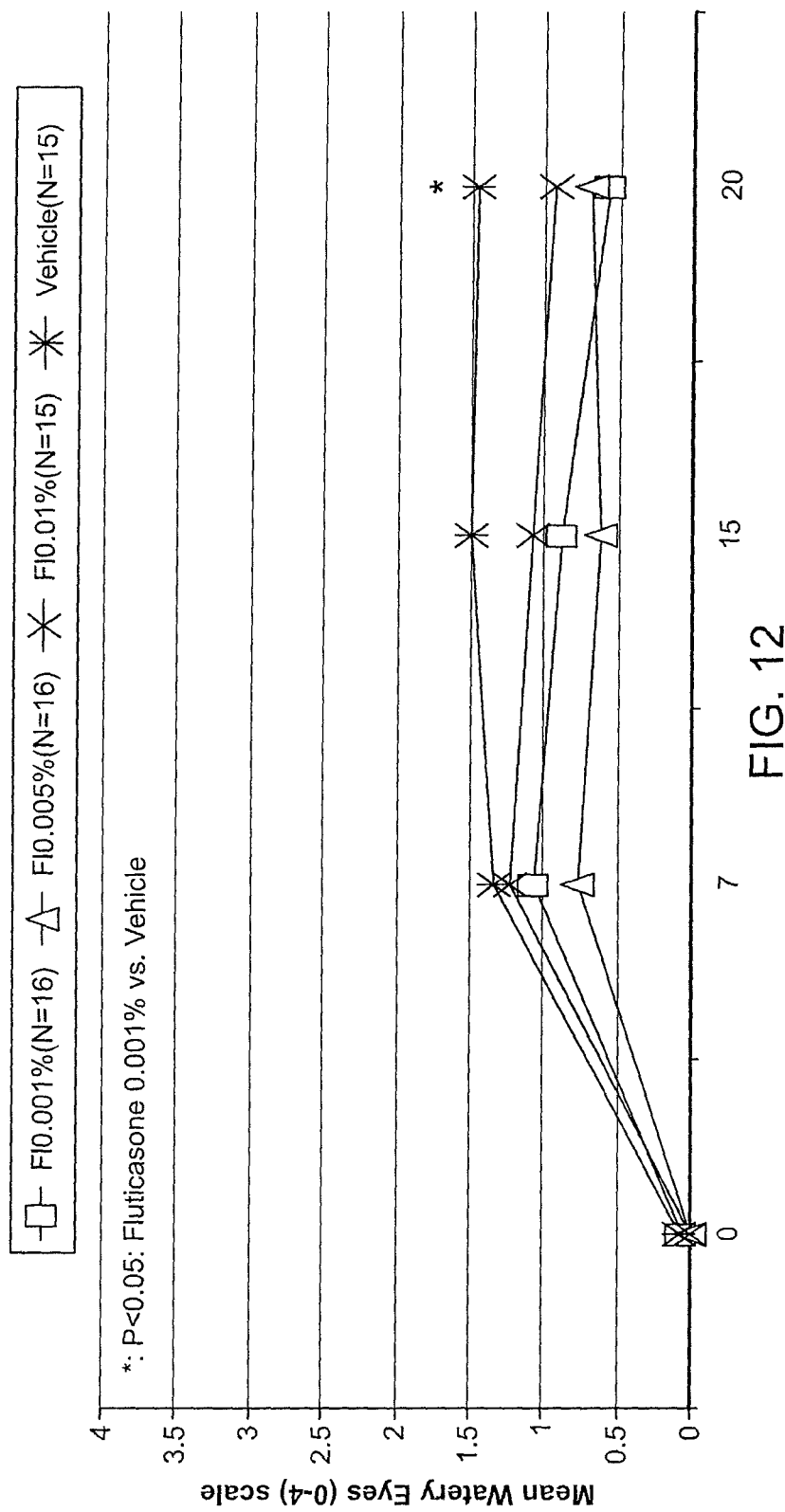
FIG. 12 is a line graph comparing the efficacy of Fluticasone 0.001%, 0.005% and 0.01% as compared to vehicle in reducing watery eyes, assessed on a scale of 0 (none) to 4 (severe) over time.

Watery eyes were also subjectively assessed on a scale of 0 (not watery) to 4 (extremely watery). As shown in FIG. 12, Fluticasone 0.001% and 0.05% were each more effective than Fluticasone 0.01% in reducing watery eyes over a 20 minute period, as compared to vehicle alone.

Figure 13:
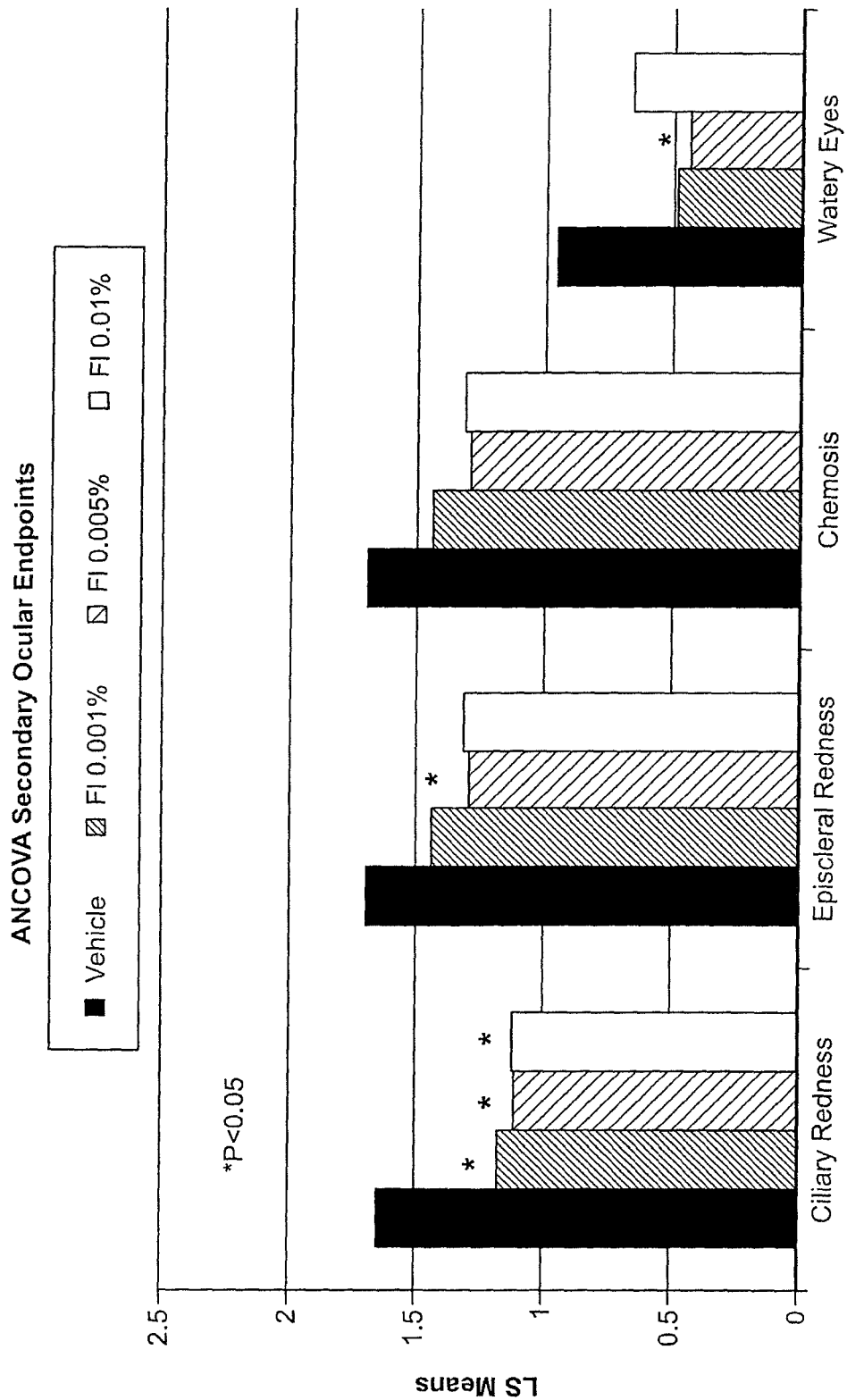
FIG. 13 is a bar graph summarizing the results shown in FIGS. 9-11.

A summary of the secondary ocular endpoints assessed is shown in FIG. 13. As shown in FIG. 13, the reduction in ciliary redness by all three concentrations of Fluticasone, the reduction in episcleral redness by Fluticasone 0.005%, and the reduction of watery eyes by Fluticasone 0.05% were each statistically significant ($p<0.05$).

Secondary Nasal Endpoints

Rhinorrhea, ear or palate pruritis, nasal pruritis were assessed in each subject at visit 4B using a scale of 0 (none) to 4 (extreme) for each endpoint.

Figure 14:
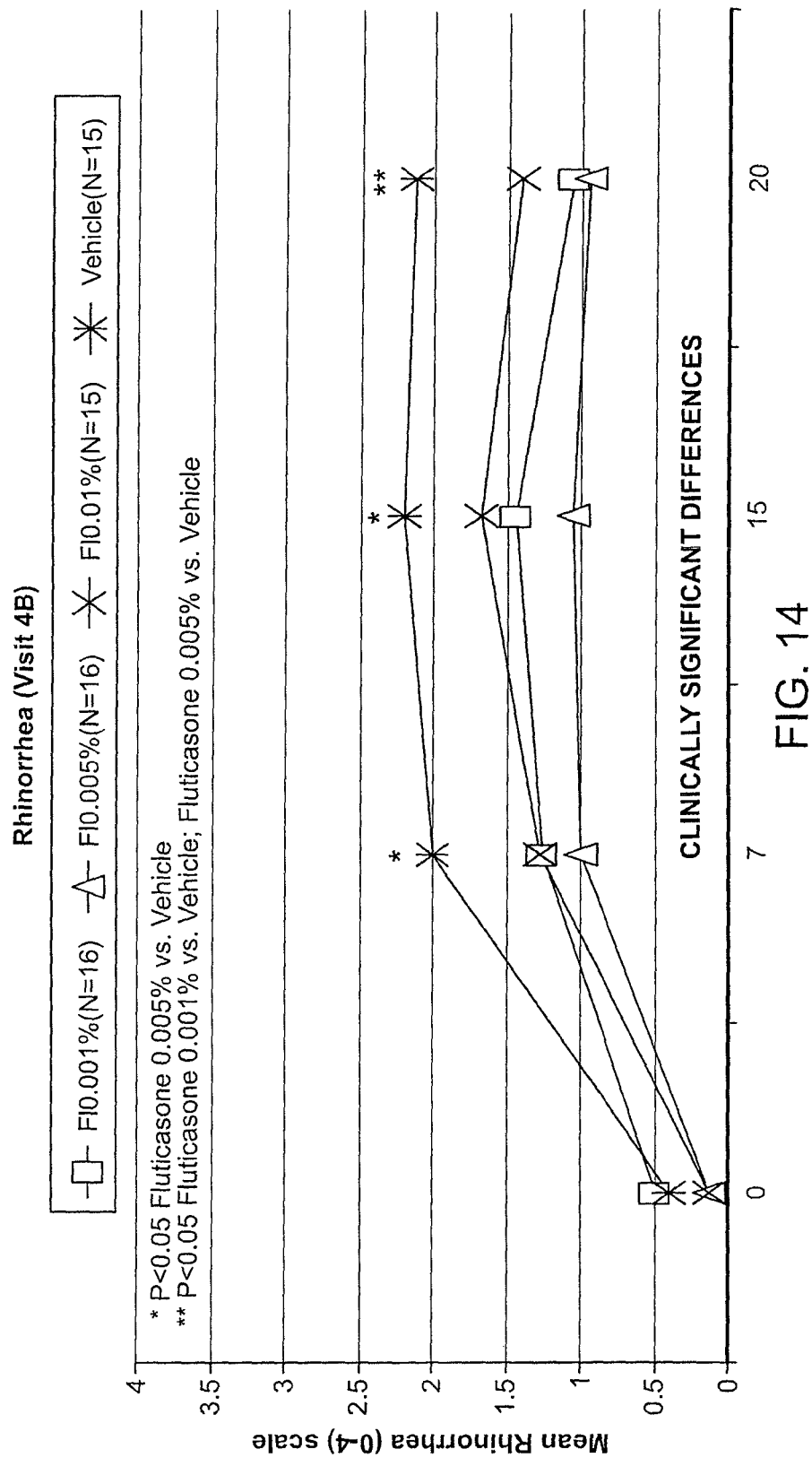
FIG. 14 is a line graph comparing the efficacy of Fluticasone 0.001%, 0.005% and 0.01% as compared to vehicle in reducing rhinorrhea, assessed on a scale of 0 (none) to 4 (severe) over time.
Figure 15:
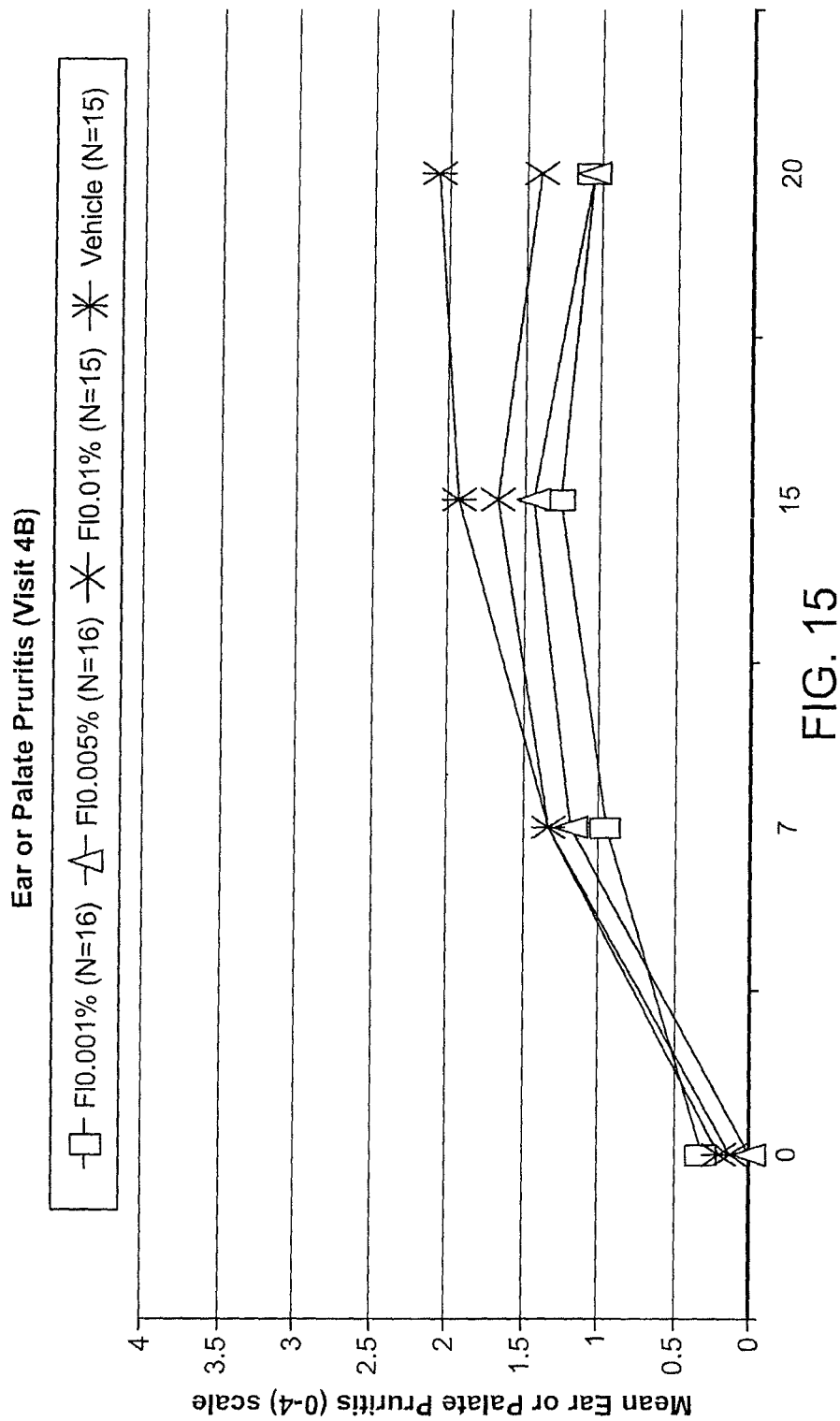
FIG. 15 is a line graph comparing the efficacy of Fluticasone 0.001%, 0.005% and 0.01% as compared to vehicle in reducing ear or palate pruritis, assessed on a scale of 0 (none) to 4 (severe) over time.
Figure 16:
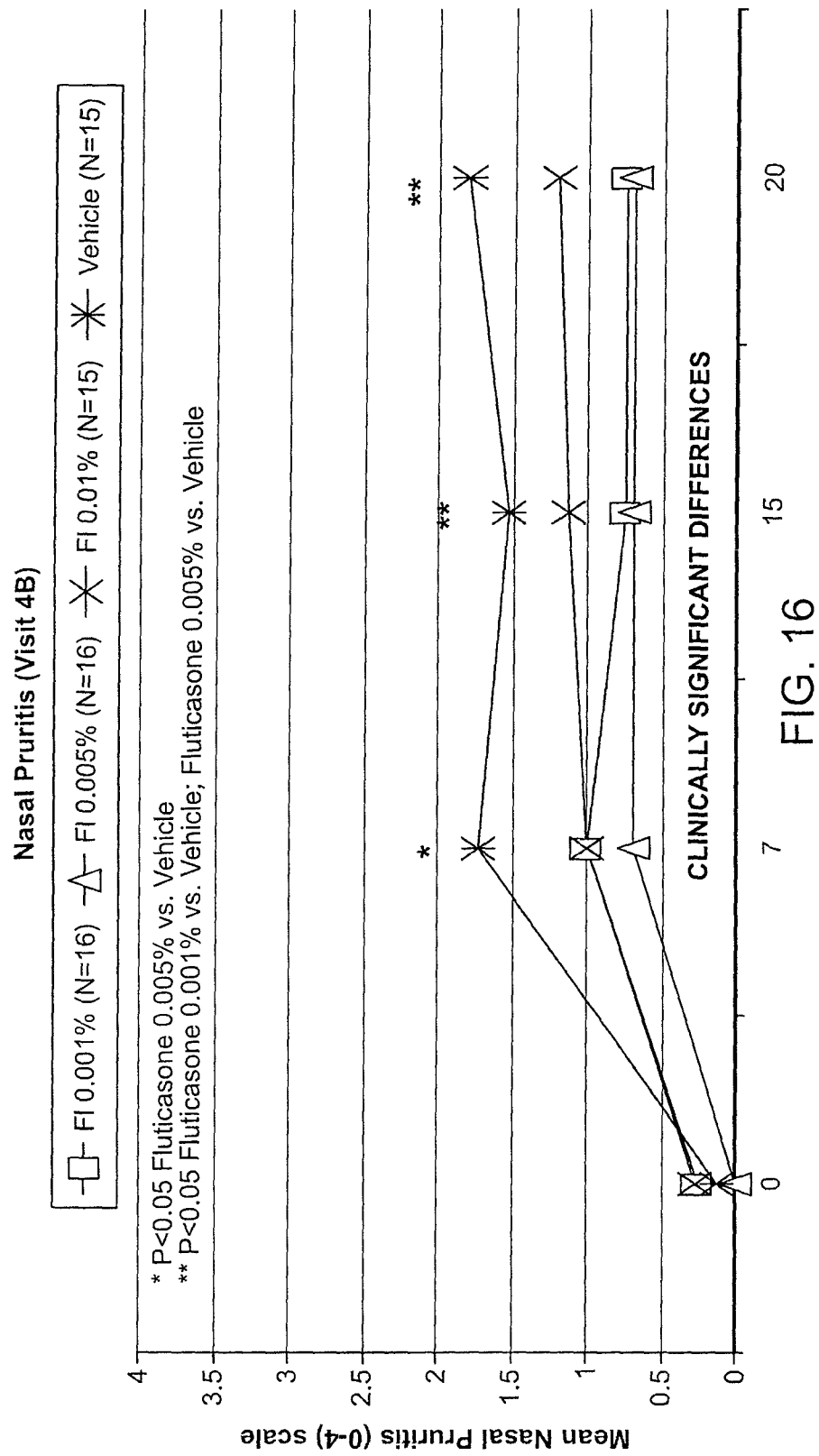
FIG. 16 is a line graph comparing the efficacy of Fluticasone 0.001%, 0.005% and 0.01% as compared to vehicle in reducing nasal pruritis, assessed on a scale of 0 (none) to 4 (severe) over time.

As shown in FIGS. 14 and 16, Fluticasone 0.001%, 0.005% and 0.01% each had a clinically significant effect in reducing rhinorrhea and nasal pruritis, respectively, over a 20 minute period as compared to vehicle alone. Shown in FIG. 15, Fluticasone 0.001%, 0.005% and 0.01% were each had an effect in reducing ear and palate pruritis as compared to vehicle alone.

Figure 17:
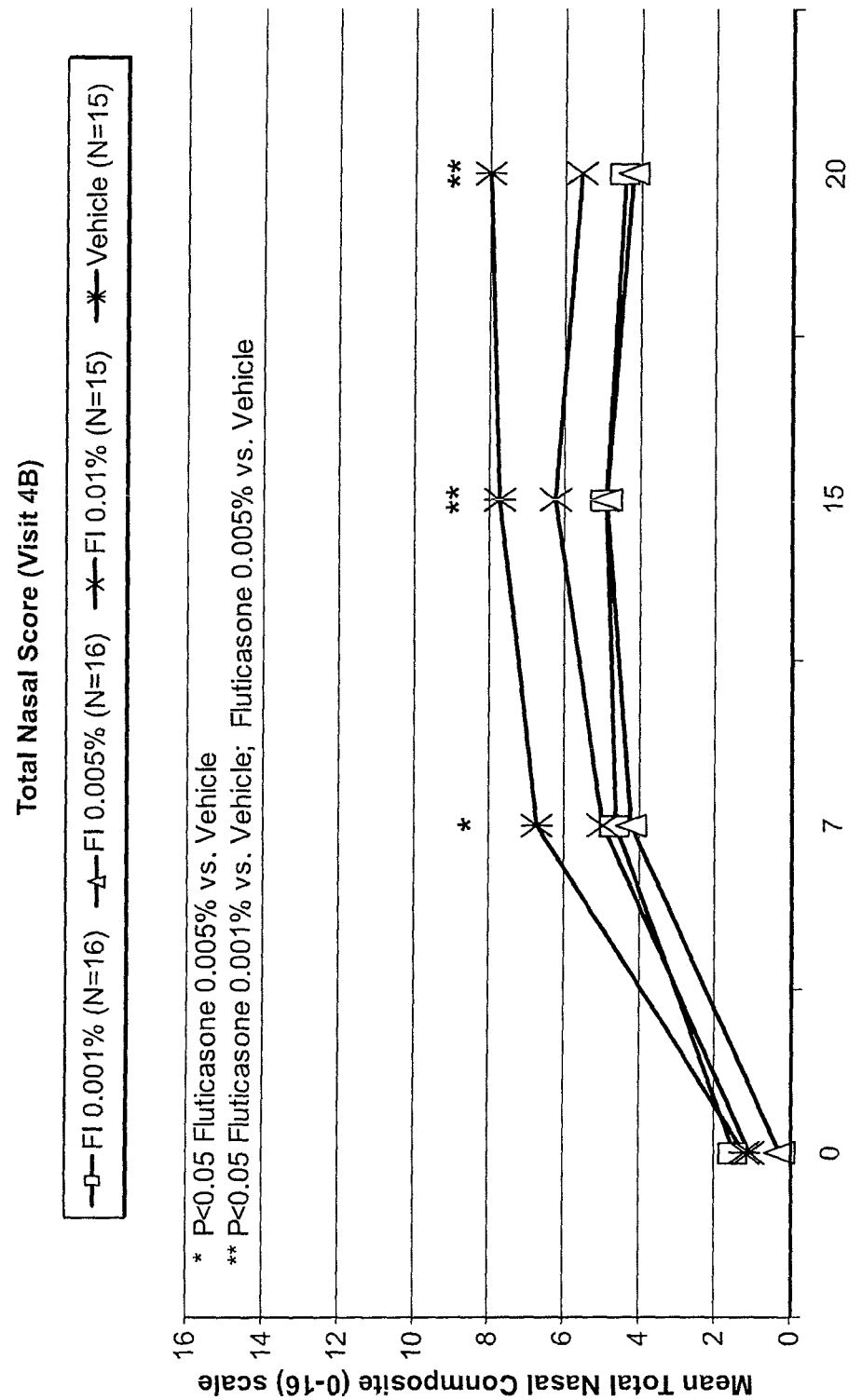
FIG. 17 is a line graph comparing the efficacy of Fluticasone 0.001%, 0.005% and 0.01% as compared to vehicle on total nasal score, assessed on a scale of 0 (no nasal symptoms) to 16 (multiple nasal symptoms) over time.
Figure 18:
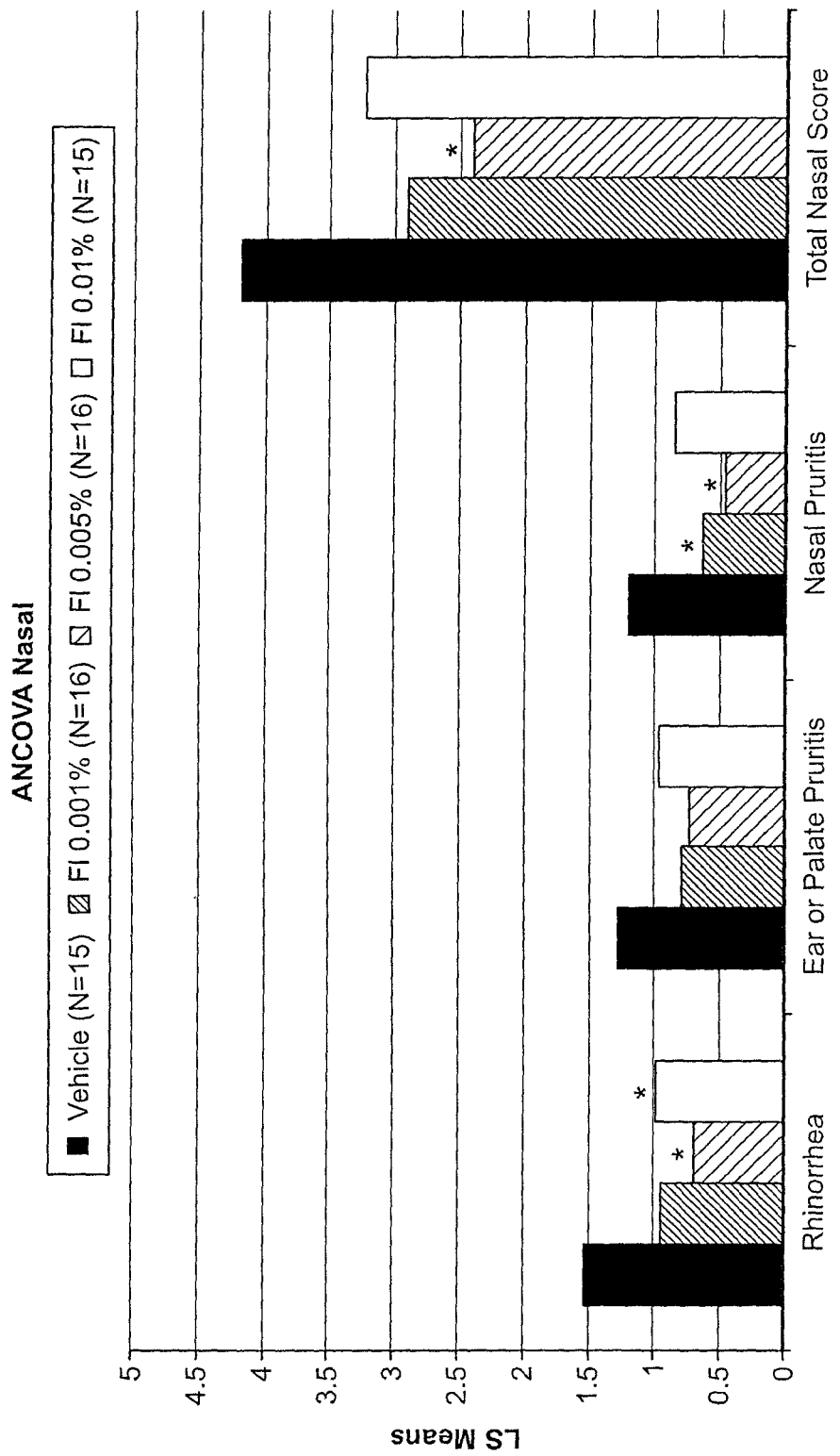
FIG. 18 is a bar graph summarizing the results shown in FIGS. 14-17.
Figure 19:
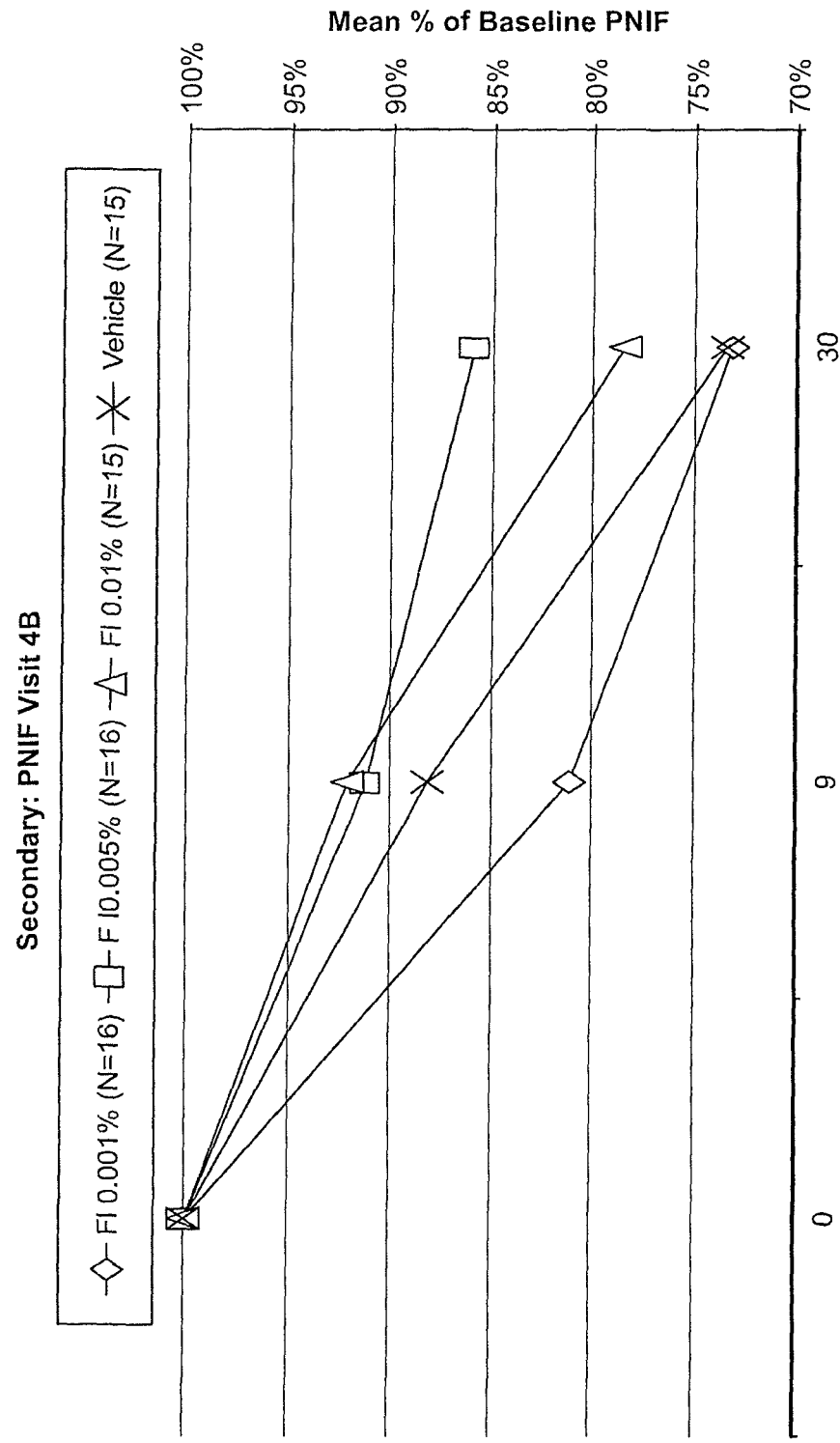
FIG. 19 is a line graph comparing the efficacy of Fluticasone 0.001%, 0.005% and 0.01% as compared to vehicle on peak nasal inspiratory flow (PNIF).

Total nasal scores were assessed on a scale of 0-16. As shown in FIG. 17, Fluticasone 0.001%, 0.005% and 0.01%, each surprisingly had a clinically significant effect on total nasal score when administered directly to the eye of each subject. A summary of the nasal endpoints assessed is shown in FIGS. 18 and 19.

Safety

Intraocular pressure, drop comfort and adverse events such as blurry vision, conjunctival hemorrhage, dry eye, site pain and/or irritation and headache, were assessed for each subject.

Figure 20:
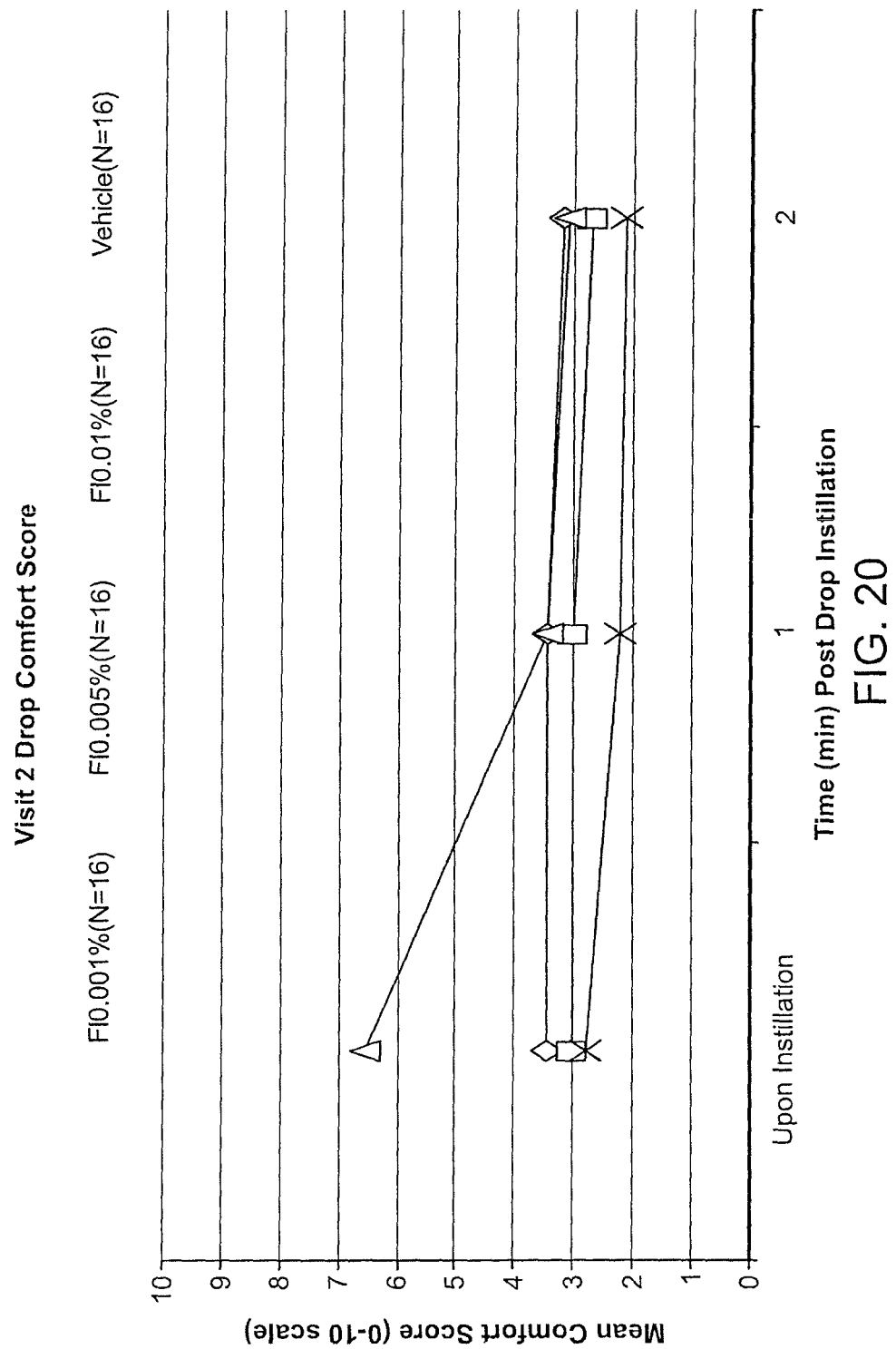
FIG. 20 a line graph comparing the drop comfort of Fluticasone 0.001%, 0.005% and 0.01% as compared to vehicle, assessed on a scale of 0 (extremely comfortable) to 10 (extremely uncomfortable) over time at Visit 2.
Figure 21:
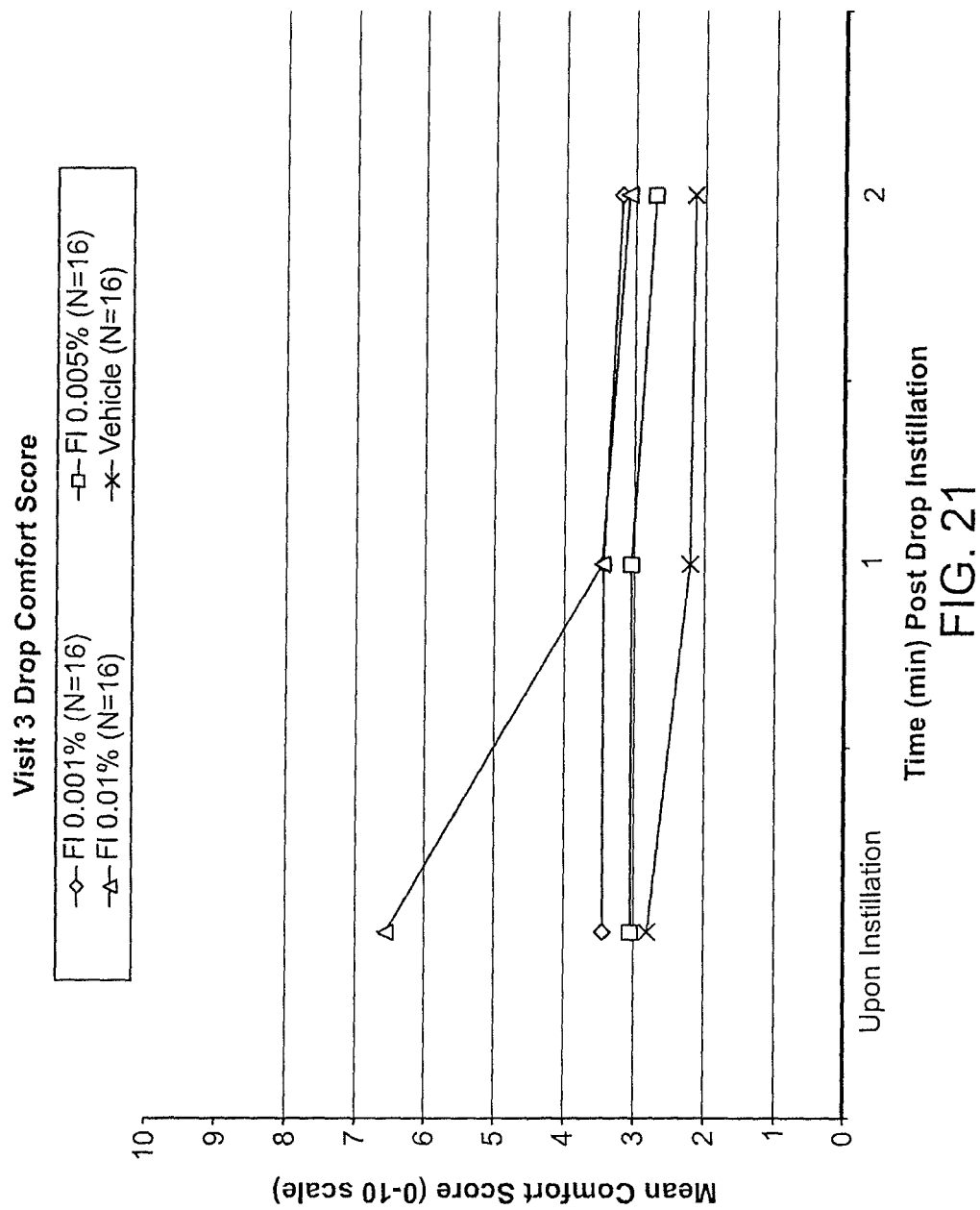
FIG. 21 a line graph comparing the drop comfort of Fluticasone 0.001%, 0.005% and 0.01% as compared to vehicle, assessed on a scale of 0 (extremely comfortable) to 10 (extremely uncomfortable) over time at Visit 3.

Drop comfort was subjectively assessed on a scale of 0 (extremely comfortable) to 10 (extremely uncomfortable) during visit 2 and visit 3. As shown in FIGS. 20 and 21, Fluticasone 0.01 was highly uncomfortable upon instillation as compared to Fluticasone 0.001% and 0.005%, and as compared to vehicle alone. The comfort of Fluticasone 0.001% and 0.005% were comparable to the comfort of the vehicle control.

A summary of the total percentage of subjects who experienced adverse events such as blurry vision, conjunctival hemorrhage, dry eye, site pain and/or irritation, and headache, is shown in FIG. 22.

Figure 23:
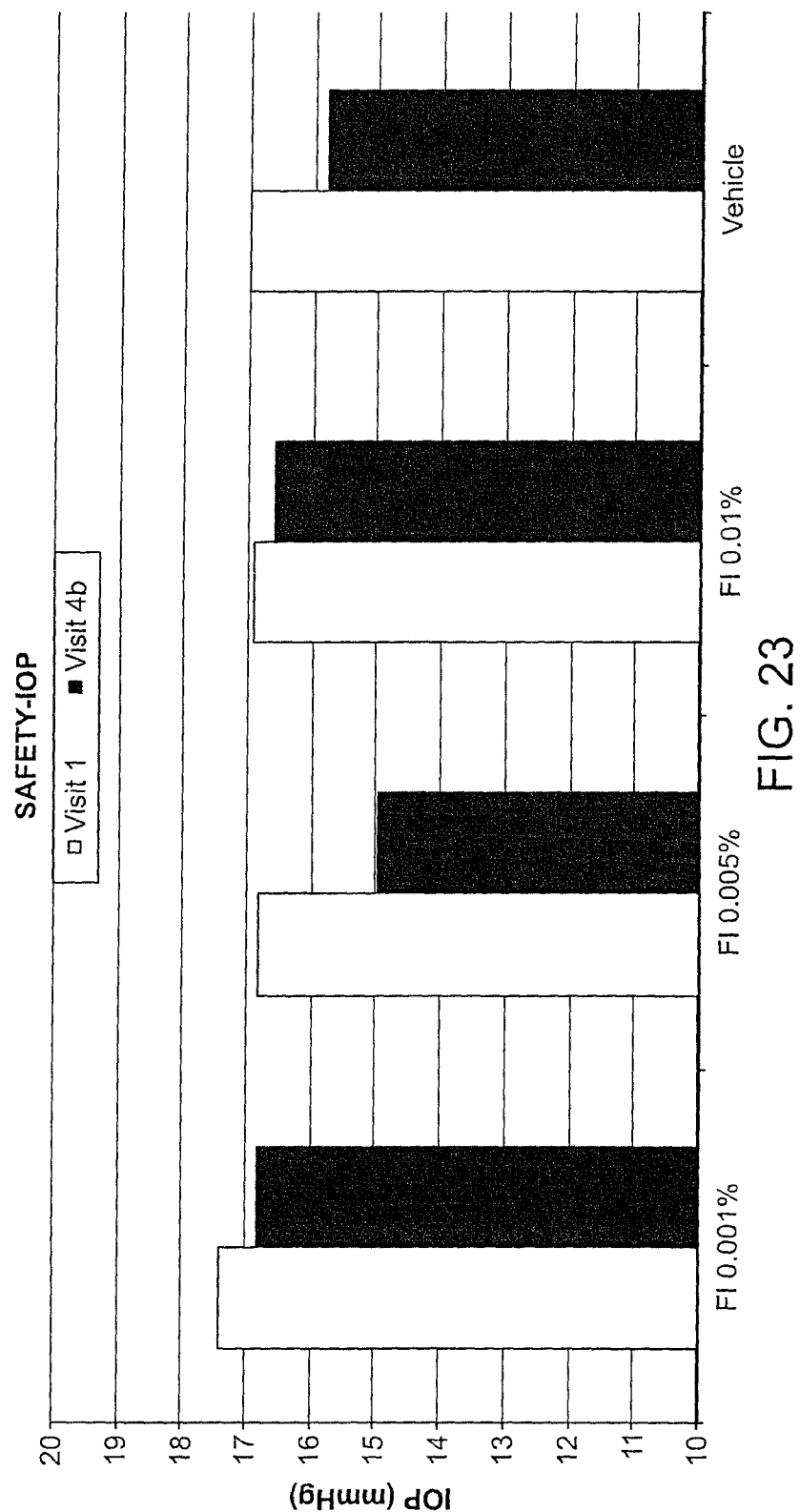
FIG. 23 is a bar graph summarizing the effects of Fluticasone 0.001%, 0.005% and 0.01% as compared to vehicle on intraocular pressure.
Figure 24:
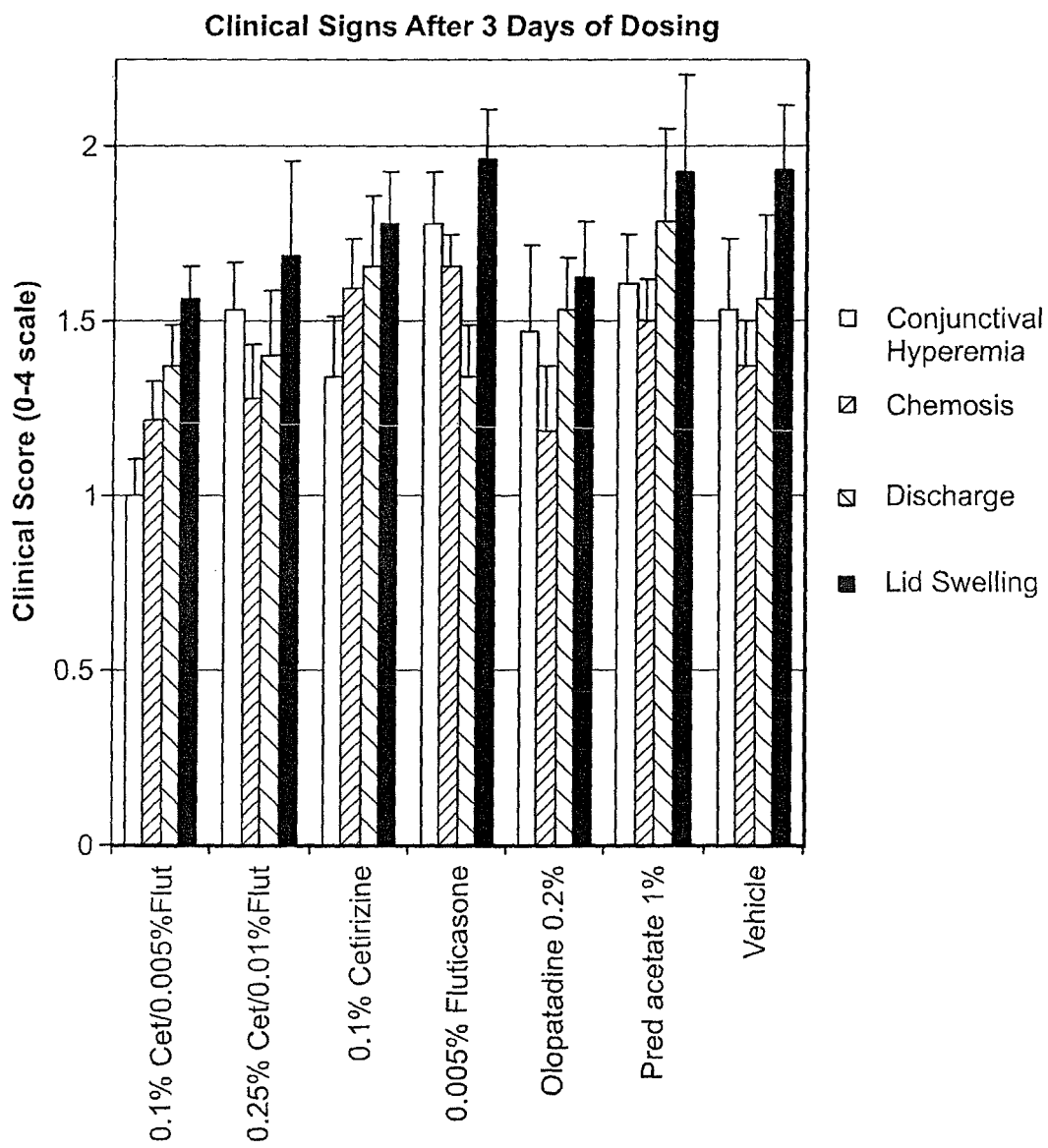
FIG. 24 is a bar graph summarizing the effects of a 0.1% cetirizine/0.005% fluticasone formulation (low dose) and a 0.25% cetirizine/0.01% fluticasone formulation (high dose) on conjunctival hyperemia, chemosis, discharge, and lid swelling after three days of dosing, as compared to 0.1% cetirizine alone, 0.005% fluticasone alone, a leading commercial antihistamine for treating allergic conjunctivitis (Pataday®; olopatadine 0.2%), a commercially available steroid (Pred Forte®; prednisolone acetate 1%) and a vehicle control.
Figure 25:
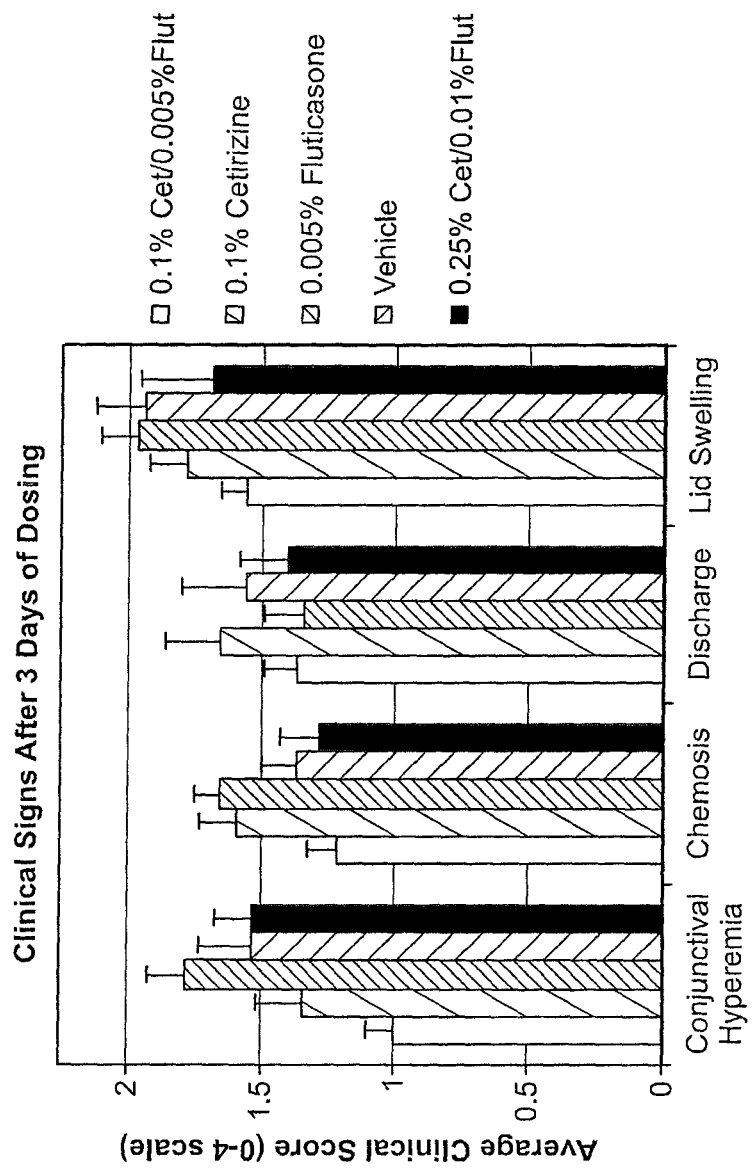
FIG. 25 is a bar graph summarizing the effects of a 0.1% cetirizine/0.005% fluticasone formulation (low dose) and a 0.25% cetirizine/0.01% fluticasone formulation (high dose) on conjunctival hyperemia, chemosis, discharge, and lid swelling after three days of dosing, as compared to 0.1% cetirizine alone, 0.005% fluticasone alone, and vehicle control.
Figure 26:
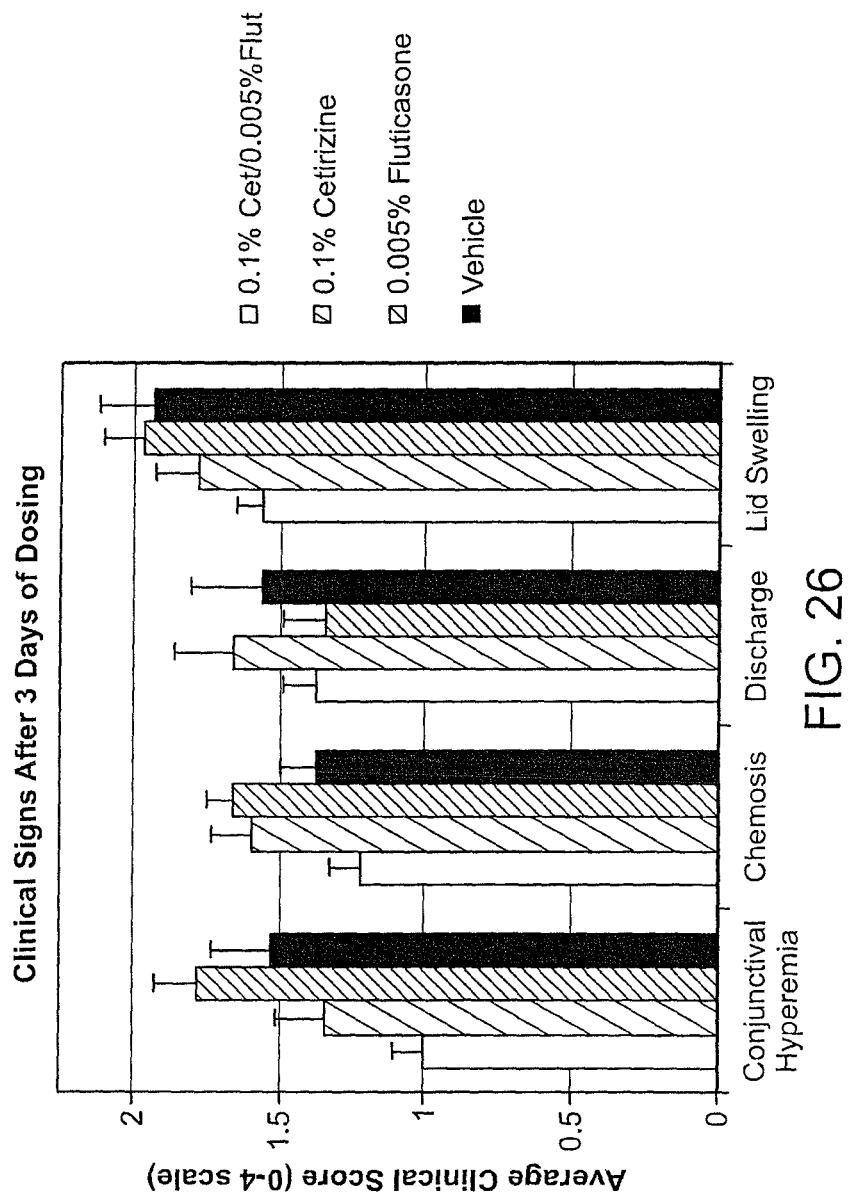
FIG. 26 is a bar graph summarizing the effects of a 0.1% cetirizine/0.005% fluticasone formulation (low dose) on conjunctival hyperemia, chemosis, discharge, and lid swelling after three days of dosing, as compared to 0.1% cetirizine alone, 0.005% fluticasone alone, and vehicle control.
Figure 27:
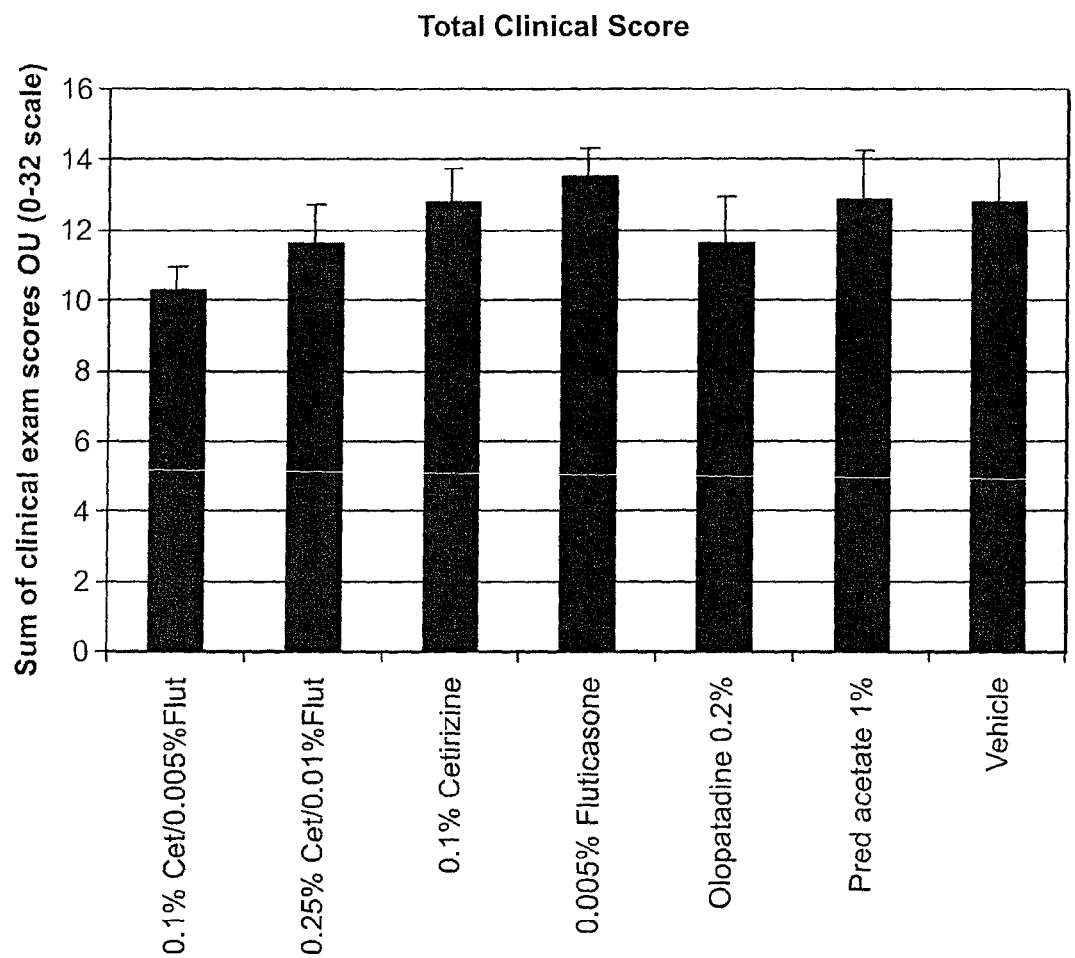
FIG. 27 is a bar graph summarizing the sum of clinical exam scores for a 0.1% cetirizine/0.005% fluticasone formulation (low dose) and a 0.25% cetirizine/0.01% fluticasone formulation (high dose), 0.1% cetirizine alone formulation, 0.005% fluticasone alone formulation, an olopatadine 0.2% formulation, a prednisolone acetate 1% formulation and a vehicle control.
Figure 28:
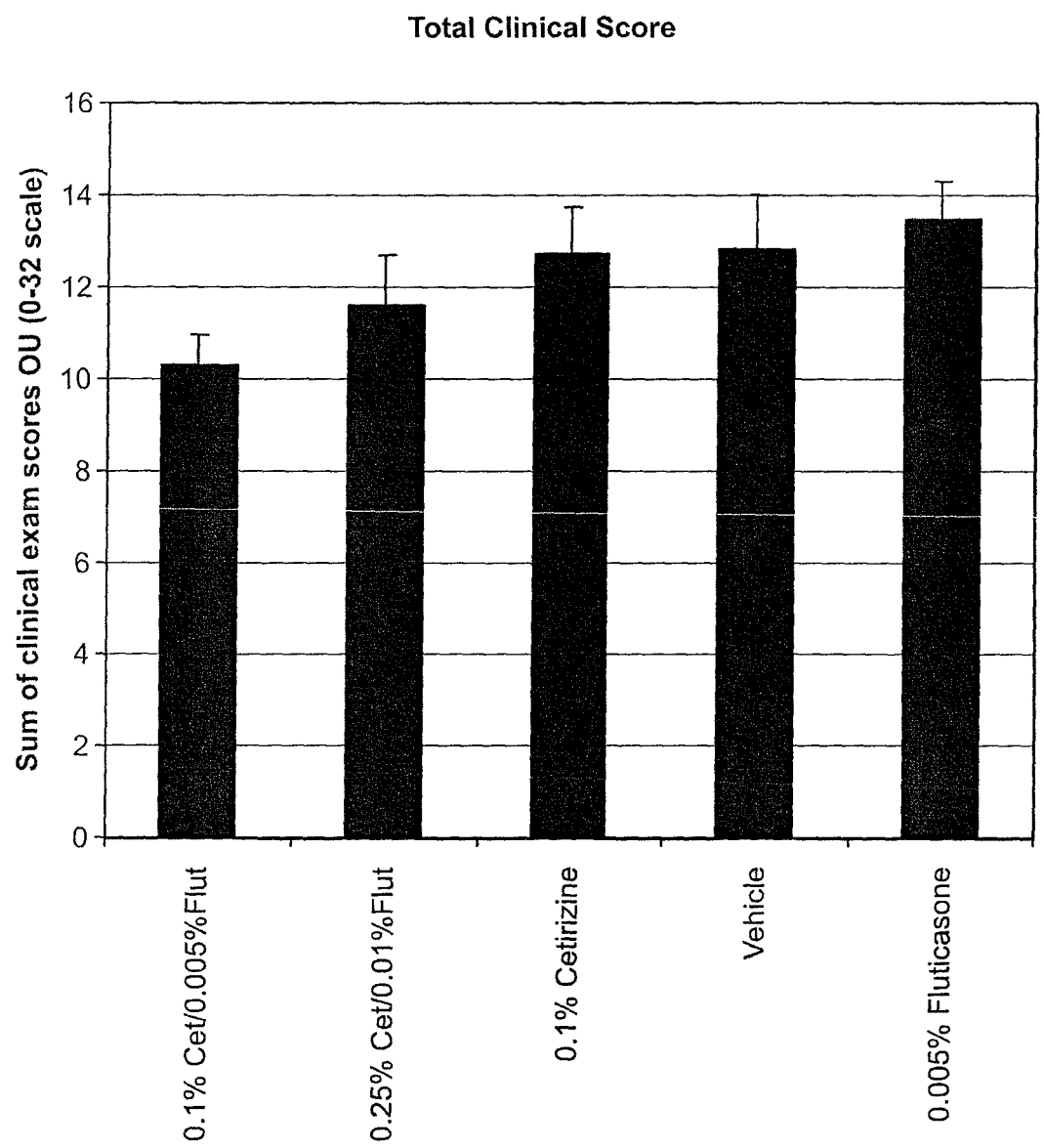
FIG. 28 is a bar graph summarizing the sum of clinical exam scores for a 0.1% cetirizine/0.005% fluticasone formulation (low dose) and a 0.25% cetirizine/0.01% fluticasone formulation (high dose), 0.1% cetirizine alone formulation, 0.005% fluticasone alone formulation, and a vehicle control.

The effect of each concentration of Fluticasone on intraocular pressure (IOP) as compared to vehicle alone is shown in FIG. 23.

The results demonstrate that a single drop of either Fluticasone 0.001%, 0.005% or 0.01% was effective to prevent both ocular and nasal symptoms associated with allergic conjunctivitis, rhinitis and rhinoconjunctivitis.

However, when taking all primary and secondary endpoints into consideration, Fluticasone 0.005% was the most efficacious in relieving both ocular and nasal symptoms, and was shown to be more comfortable than Fluticasone 0.001% and Fluticasone 0.01%, with no adverse effect on intraocular pressure.

Example 3

An Evaluation of the Effects of Topical Cetirizine/Fluticasone Ophthalmic Formulations on the Signs of Allergic Conjunctivitis using the Murine Model of Ragweed-Induced Active Anaphylaxis Seasonal allergic conjunctivitis (hay fever conjunctivitis) develops in a subset of atopic individuals (those with a genetic disposition of hypersensitivity to allergens). The signs and symptoms of the condition are elicited by airborne allergens (e.g. ragweed, tree and grass pollens, animal dander). Seasonal allergic conjunctivitis is the most common form of ocular allergic disease and may account for up to 90% of allergic disorders seen.

The most common and distressing ocular signs and symptoms associated with allergic conjunctivitis are itching and redness. Swelling, mucous discharge and excessive tearing are frequently involved. In allergic conjunctivitis, airborne allergens presumably dissolve in the tear film, traverse the conjunctiva, and then bind with IgE antibodies attached to the surface of the conjunctival mast cell to trigger an allergic response. This attachment results in mast cell degranulation and release of chemical mediators that lead to signs and symptoms of allergic disease. Some of these substances, e.g. histamines and prostaglandins, directly affect blood vessels and nerves, whereas others influence the migration of inflammatory cells such as neutrophils, eosinophils and macrophages, causing inflammation.

The major chemical mediator involved in producing ocular symptoms is histamine. Several types of histamine have been identified in the human conjunctiva. Stimulation of H1 receptors results mainly in itching while stimulation of H2 receptors results largely in vasodilation (redness). However, studies with antihistamines known to be highly specific for H1 receptors have suggested that H1 receptors may also have a secondary effect on redness.

The purpose of this study was to investigate the potential of cetirizine/fluticasone combination formulations in preventing signs of allergic conjunctivitis in a murine active anaphylaxis model. In this model, mice are systemically sensitized to short ragweed allergen (SRW) and then challenged by instilling SRW in the eyes. Therapeutic treatment is given after sensitization but prior to topical challenge. Allergens present in the SRW preparation cross-link IgE antibodies bound to conjunctival mast cells causing degranulation and release of histamine and other allergic mediators, which in turn produce the characteristic signs and symptoms of allergic conjunctivitis.

Four test formulations, containing combination 0.1% Cetirizine/0.005% Fluticasone ("low dose"), combination 0.25% Cetirizine/0.01% Fluticasone ("high dose"), 0.1% Cetirizine or 0.005% Fluticasone, were compared with vehicle alone (1% Polyethylene Glycol 400, NF; 0.2% Dibasic Sodium Phosphate, Anhydrous, USP; 0.25% Hypromellose, USP; 0.1% Polysorbate 80, NF; 1.8% Glycerin, USP; 0.025% Edetate Disodium, USP; 0.01% Benzalkonium Chloride, NF (pH 7.0)) and two commercial positive controls, Pred Forte® (prednisolone acetate 1%) and Pataday® (olopatadine 0.2%).

Systemic sensitization to short ragweed allergen (SRW) was induced by injecting SRW plus alum adjuvant systemically into Balb/c mice (Day 1), and by administration of topical SRW eyedrops on days 19-21. Topical ocular drug treatment was administered daily on days 19-21 after SRW injection. After 3 days of treatment, the animals were assessed for signs of allergic conjunctivits in response to challenge with topical SRW administration. Clinical assessments included conjunctival hyperemia, chemosis, discharge and lid swelling, each graded biomicroscopically on a 0-4 severity scale.

After 3 days of drug treatment, the animals treated with the combination 0.1% Cetirizine/0.005% Fluticasone demonstrated the least severity in three clinical signs (conjunctival hyperemia, chemosis, and lid swelling) as compared Cetirizine or Fluticasone alone or as compared to most other treatment groups. Cetirizine or Fluticasone alone produced no significant treatment effects.

The reduction in clinical signs in response to SRW challenge after 3 days of treatment with the combination 0.1% Cetirizine/0.005% Fluticasone was statistically significantly lower than Fluticasone alone for hyperemia ($p \leq 0.001$), chemosis ($p \leq 0.01$), lid swelling ($p \leq 0.03$) and total clinical score ($p \leq 0.01$); and than Cetirizine alone for chemosis ($p \leq 0.05$). Additionally, statistical significance was almost achieved against Cetirizine alone for total clinical score ($p = 0.06$). Surprisingly, the reduction with the combination was more than could have been expected from the efficacy of the individual components.

Furthermore, the combination of 0.1% Cetirizine/0.005% Fluticasone performed better than either the steroid (Pred Forte®) or antihistamine (Pataday®), leading commercial products used as positive controls in this study. Additionally, the higher concentration of the combination (0.25% Cetirizine/0.01% Fluticasone) was minimally effective in this model under this dosing regimen and conditions.

The results of this study indicate that a substantial clinical benefit may be achieved with the combination of low dose Cetirizine/Fluticasone over its individual components, over the high dose combination and over existing lead commercial products.

Experimental Design:

TABLE 3

Schedule of Procedures

| Procedure | Day 0 | Day 19 | Day 20 | Day 21 | Day 26 |
|---|---|---|---|---|---|
| Ocular Exam | X | | | X | |
| SRW Injection | X | | | | |
| Topical SRW | | X | X | X | |
| Dosing | | X | X | X | |
| Challenge | | | | X | |
| Behavior Observations | | | | X | |

TABLE 3-continued

Schedule of Procedures

| Procedure | Day 0 | Day 19 | Day 20 | Day 21 | Day 26 |
|---|---|---|---|---|---|
| Photographs | | | | X | |
| Euthanasia | | | | | X |
| Eye Enucleations | | | | | X |

Sensitization

On Day 0, animals received injections containing a suspension of 50 µg of short ragweed allergen (SRW, Greer, Lenoir, N.C., USA) in 25 µL alum (aluminum hydroxide gel). Additional sensitization was achieved by topical dosing with 1 mg SRW in 5 µl PBS on Days 19 and 20 after injection.

Dosing

On days 19 through 21, topical treatment was administered once daily. Mice were dosed topically to the central cornea using a calibrated micropipette, with a 5 µL drop of treatment in each eye. The dose groups are outlined in the table below:

Challenge

On day 21, twenty minutes after ocular treatment dosing, animals were challenged with topical doses of 1000 µg SRW suspension in 5 µl PBS in each eye. SRW was prepared fresh and used within 3 hours of mixing, and mixed well before administration to ensure homogeneity.

TABLE 4

Test/Control Articles

| Group Number | Number of Animals | Test Article | Volume per Dose |
|---|---|---|---|
| 1 | 8 | 0.1% Cetirizine/0.005% Fluticasone | 5 µL |
| 2 | 8 | 0.25% Cetirizine/0.01% Fluticasone | 5 µL |
| 3 | 8 | 0.1% Cetirizine | 5 µL |
| 4 | 8 | 0.005% Fluticasone | 5 µL |
| 5 | 8 | Olopatadine HCl 0.2% (Pataday ®) | 5 µL |
| 6 | 8 | Pred. acetate 1% (Pred Forte ®) | 5 µL |
| 7 | 8 | Vehicle Control | 5 µL |

Experimental Procedures:

Ophthalmic exams were performed at baseline (study entry) according to the Ocular Irritation Grading Scale to verify that the eyes did not exhibit any signs of ocular irritation.

Ophthalmic exams were also performed on day 21, 15 minutes after the allergen challenge. Exams were performed under dissecting microscope, and included conjunctival hyperemia, chemoosis, tear/discharge, and lid swelling, each graded on a 0-4 scale (0.5 units were allowed for any ocular score).

There were no abnormal ophthalmic findings in any animals used in the study and no unscheduled deaths during this study.

Tissue Collections/Preservation and Statistical Analysis

Immediately after euthanasia ($CO_2$ inhalation and cervical dislocation), eyes and surrounding lid tissue was collected and placed immediately in 4% paraformaldehyde for 24 hours, after which they were transferred to 70% ethanol for storage prior to paraffin embedding and sectioning for histology.

Both eyes of each animal were averaged and all animals within a group were averaged to obtain an average score for each treatment group for each measurement parameter. Statistically significant differences between groups were determined using the 2-tailed, 2-sample t-test.

Results

Day 0 baseline exams ensured that all mice were free of any redness, swelling, and tearing.

After 3 days of drug treatment, the animals treated with the combination 0.1% Cetirizine/0.005% Fluticasone demonstrated the least severity in three of the four clinical signs (conjunctival hyperemia, chemosis, and lid swelling) as compared to Cetirizine or Fluticasone alone, and as compared to most other treatment groups. Total clinical score (sum of scores of all clinical signs in both eyes) was lowest in the 0.1% Cetirizine/0.005% Fluticasone combination group as compared to all other treatment groups. Cetirizine or Fluticasone alone produced no significant treatment effects.

The reduction in clinical signs in response to SRW challenge after 3 days of treatment with the combination 0.1% Cetirizine/0.005% Fluticasone was statistically significantly lower than Fluticasone alone for hyperemia ($p \leq 0.001$), chemosis ($p \leq 0.01$), lid swelling ($p \leq 0.03$) and total clinical score ($p \leq 0.01$); and than Cetirizine alone for chemosis ($p \leq 0.05$). Borderline significance was achieved against Cetirizine alone for total clinical score ($p = 0.06$).

Surprisingly, the high dose combination of 0.25% Cetirizine/0.01% Fluticasone was less effective than the low dose combination in this model for all clinical signs, with the exception of an effect on chemosis. The only statistically significant decrease in any clinical sign after high dose combination treatment was for chemosis as compared to Fluticasone alone ($p \leq 0.05$).

Under these treatment conditions (3 days of once-daily dosing), neither of the positive control test articles, commercially available Pred Forte (prednisolone acetate 1%), a steroid, or Pataday (olopatadine 0.2%), the leading anti-histamine, produced significant treatment effects, with the exception of a decrease in chemosis produced by olopatadine, comparable to the effect seen with the combination 0.1% Cetirizine/0.005% Fluticasone. This chemosis effect was statistically significantly different from Fluticasone alone ($p \leq 0.05$).

The results are summarized in Table 5 below and in FIGS. 24-28.

same concentrations, produced a substantial treatment effect. The low-dose combination, assessed after 3 days of treatment and 15 minutes after ragweed challenge, reduced conjunctival hyperemia, chemosis, and lid swelling, and resulted in the lowest clinical summary score of any of the treatment arms, including the cetirizine or fluticasone alone, and commercial ophthalmics Pataday® and Pred Forte®.

Surprisingly, the higher concentration of the combination (0.25% Cetirizine/0.01% Fluticasone) was minimally effective in this model under this dosing regimen and conditions. These results indicate that the 0.1% Cetirizine/0.005% Fluticasone formulation has excellent potential for the prevention and treatment of allergic conjunctivitis and that a substantial clinical benefit might be achieved with the combination of Cetirizine/Fluticasone over either medication used alone.

In summary, the results consistently favored 0.1% cetirizine/0.005% fluticasone combination (low dose) over both the individual components alone as well as the high dose combination (0.25% cetirizine/0.01% fluticasone), which is surprising because one skilled in the art might expect the higher dose formulation to work at least equally well if not better than the low dose formulation. The low dose combination also worked better than would be expected from the results of the individual components, thus showed a synergistic effect between the cetirizine and fluticasone Additionally, the low dose combination worked better than well known, leading ocular antihistamines and ocular steroid—these results confirm the effectiveness of the specific combination of cetirizine/fluticasone at the preferred low dose concentrations.

Lastly, the low dose combination was more efficacious than its comparison arms across all endpoints, including total ocular composite score.

Example 4

Comfort Profile of Cetirizine/Fluticasone Formulation

The purpose of this study was to assess the comfort of a 0.1% cetirizine/0.005% fluticasone (low dose) formulation and a 0.25% cetirizine/0.01% fluticasone (high dose) formu-

TABLE 5

Summary of Results

| Treatment Group | Conjunctival Hyperemia | | Chemosis | | Discharge | | Lid Edema | | Total Clinical Score | |
|---|---|---|---|---|---|---|---|---|---|---|
| | Average | SEM | Avg | SEM | Avg | SEM | Avg | SEM | Avg | SEM |
| 0.1% Cetirizine/ 0.005% Fluticasone | 1.00 | 0.11 | 1.22 | 0.11 | 1.38 | 0.12 | 1.56 | 0.09 | 10.31 | 0.66 |
| 0.25% Cetirizine/ 0.01% Fluticasone | 1.53 | 0.14 | 1.28 | 0.15 | 1.41 | 0.18 | 1.69 | 0.27 | 11.63 | 1.09 |
| 0.1% Cetirizine | 1.34 | 0.17 | 1.59 | 0.14 | 1.66 | 0.21 | 1.78 | 0.15 | 12.75 | 1.00 |
| 0.005% Fluticasone | 1.78 | 0.15 | 1.66 | 0.09 | 1.34 | 0.15 | 1.97 | 0.14 | 13.50 | 0.80 |
| Olopatadine HCl 0.2% (Pataday ®) | 1.47 | 0.25 | 1.19 | 0.19 | 1.53 | 0.15 | 1.63 | 0.16 | 11.63 | 1.34 |
| Pred. acetate 1% (Pred Forte ®) | 1.61 | 0.14 | 1.50 | 0.12 | 1.79 | 0.26 | 1.93 | 0.28 | 12.86 | 1.43 |
| Vehicle Control | 1.53 | 0.20 | 1.38 | 0.13 | 1.56 | 0.24 | 1.94 | 0.18 | 12.81 | 1.19 |

Conclusion:

The low dose combination of 0.1% Cetirizine/0.005% Fluticasone was the most effective at preventing signs of allergic conjunctivitis in the murine ragweed sensitization model. Neither component of the combination used alone, at the same lation upon instillation in the human eye (N=5). The low dose and high dose combinations were each formulated in 1% Polyethylene Glycol 400, NF; 0.2% Dibasic Sodium Phosphate, Anhydrous, USP; 0.25% Hypromellose, USP; 0.1% Polysorbate 80, NF; 1.8% Glycerin, USP; 0.025% Edetate Disodium, USP; 0.01% Benzalkonium Chloride, NF, as reflected in Tables 6 and 6 below:

TABLE 6

0.005% Fluticasone Propionate/0.1% Cetirizine Ophthalmic Suspension

| Concentration | Ingredient | Purpose |
|---|---|---|
| 0.005% | Fluticasone Propionate, USP | Active, Steroid |
| 1% | Polyethylene Glycol 400, NF | Carrier |
| 0.2% | Dibasic Sodium Phosphate, Anhydrous, USP | Buffer |
| 0.1188% | Cetirizine Dihydrochloride, Ph. Eur. | Active, Antihistamine |
| 0.25% | Hypromellose, USP | Viscosity agent |
| 0.1% | Polysorbate 80, NF | Surfactant |
| 1.8% | Glycerin, USP | Tonicity Agent |
| 0.025% | Edetate Disodium, USP | Chelating Agent |
| 0.01% | Benzalkonium Chloride, N.F. | Preservative |
| q.s. | Sterile Purified Water | Vehicle |

TABLE 7

0.01% Fluticasone Propionate/0.25% Cetirizine Ophthalmic Suspension

| Concentration | Ingredient | Purpose |
|---|---|---|
| 0.01% | Fluticasone Propionate, USP | Active, Steroid |
| 2% | Polyethylene Glycol 400, NF | Carrier |
| 0.2% | Dibasic Sodium Phosphate, Anhydrous, USP | Buffer |
| 0.297% | Cetirizine Dihydrochloride, Ph. Eur. | Active, Antihistamine |
| 0.25% | Hypromellose, USP | Viscosity agent |
| 0.1% | Polysorbate 80, NF | Surfactant |
| 1.2% | Glycerin, USP | Tonicity Agent |
| 0.025% | Edetate Disodium, USP | Chelating Agent |
| 0.01% | Benzalkonium Chloride, N.F. | Preservative |
| q.s. | Sterile Purified Water | Vehicle |

Each of the formulations in Tables 5 and 6 had a pH 7.0 and an osmolality of 300 mOsm/kg.

Figure 29:
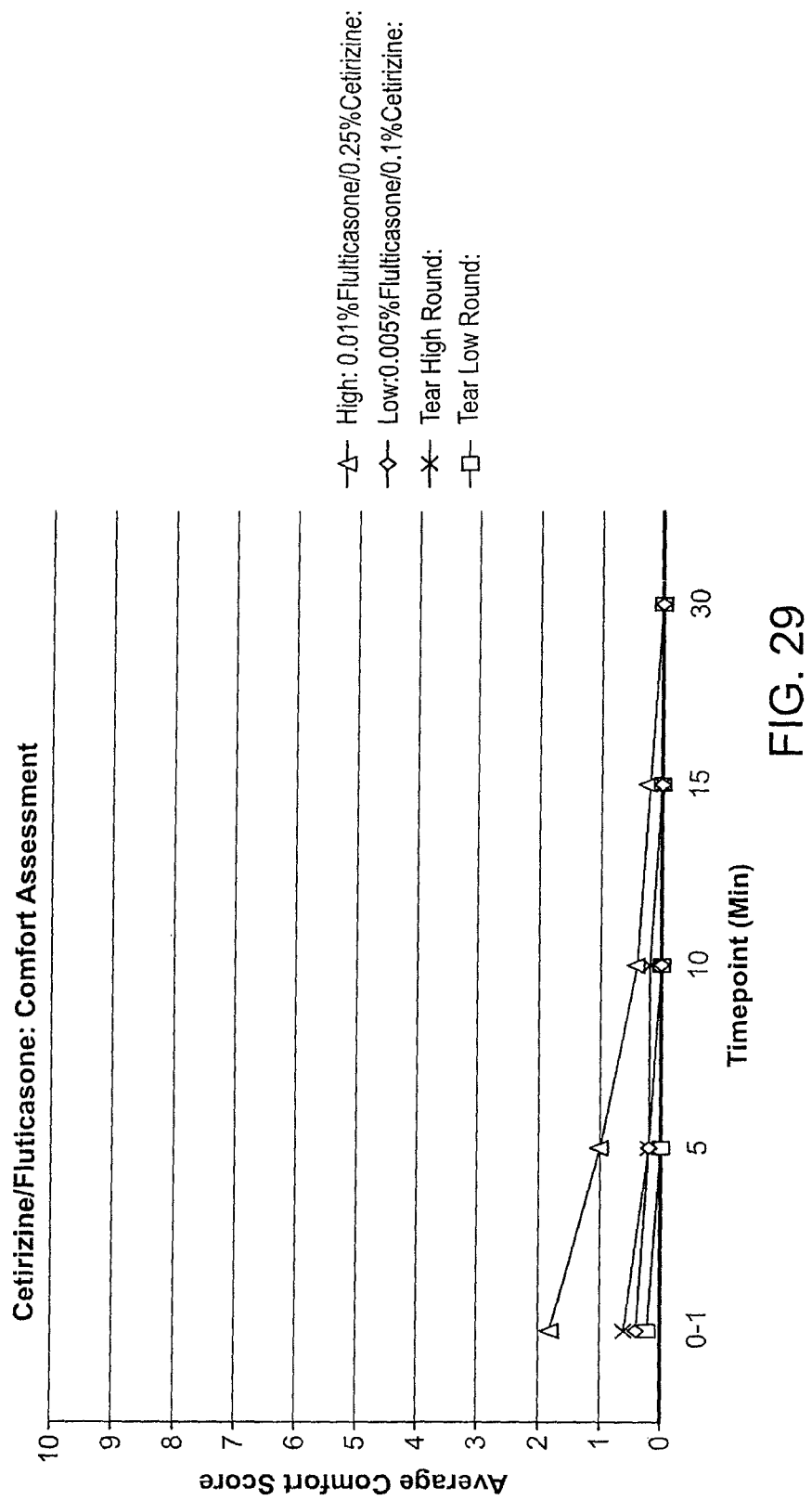
FIG. 29 is a line graph depicting the comfort profile of a 0.1% cetirizine/0.005% fluticasone formulation (low dose) and a 0.25% cetirizine/0.01% fluticasone formulation (high dose) upon instillation in the eye as compared to controls. The comfort of the formulation is indicated on a subjective scale of 0 to 10 (0=very comfortable; 10=very uncomfortable).
Figure 30:
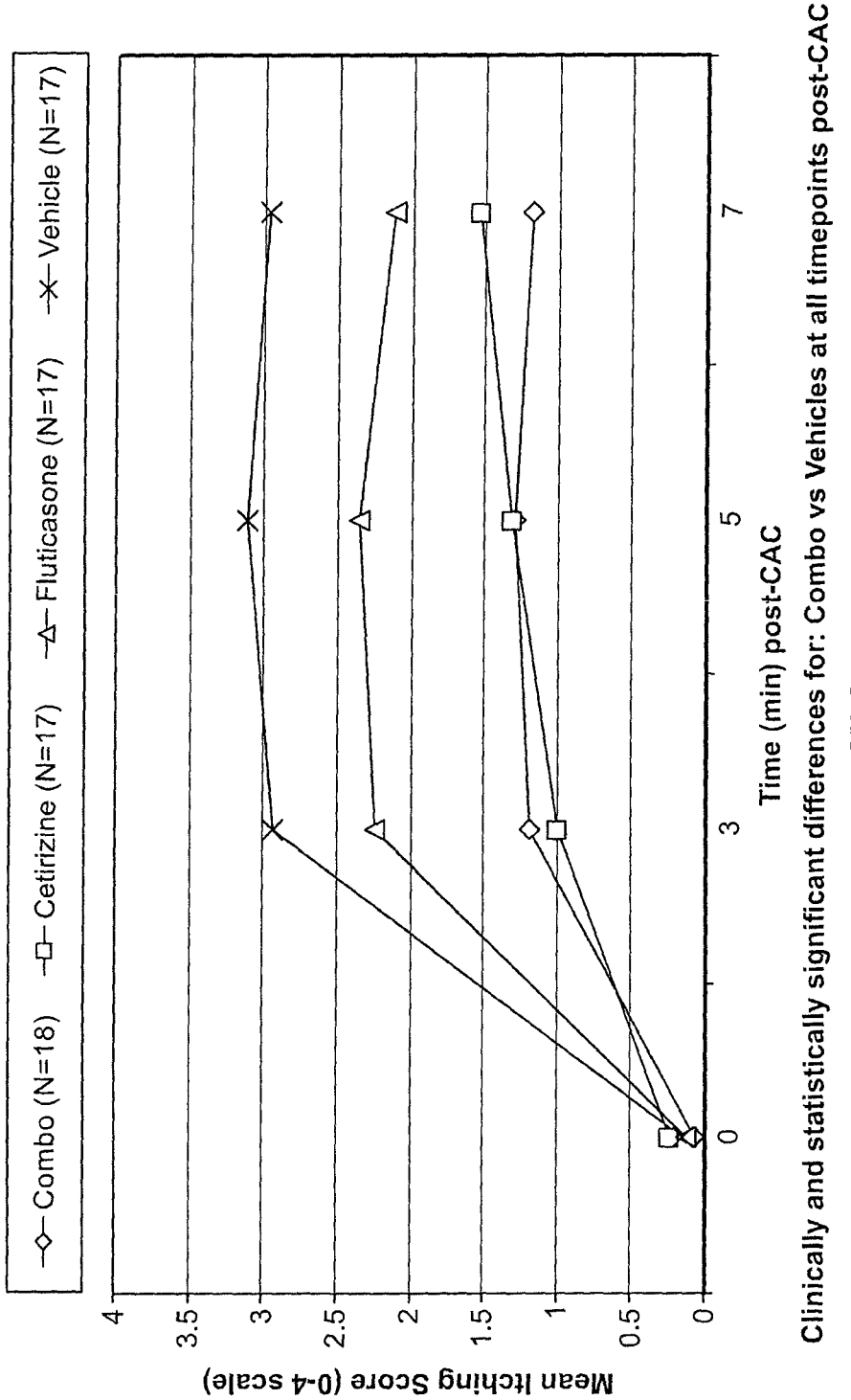
FIG. 30 is a line graph depicting the mean itching score at visit 3post CAC for a 0.1% cetirizine/0.005% fluticasone formulation (low dose), 0.1% cetirizine alone formulation, 0.005% fluticasone alone formulation, and a vehicle control.
Figure 31:
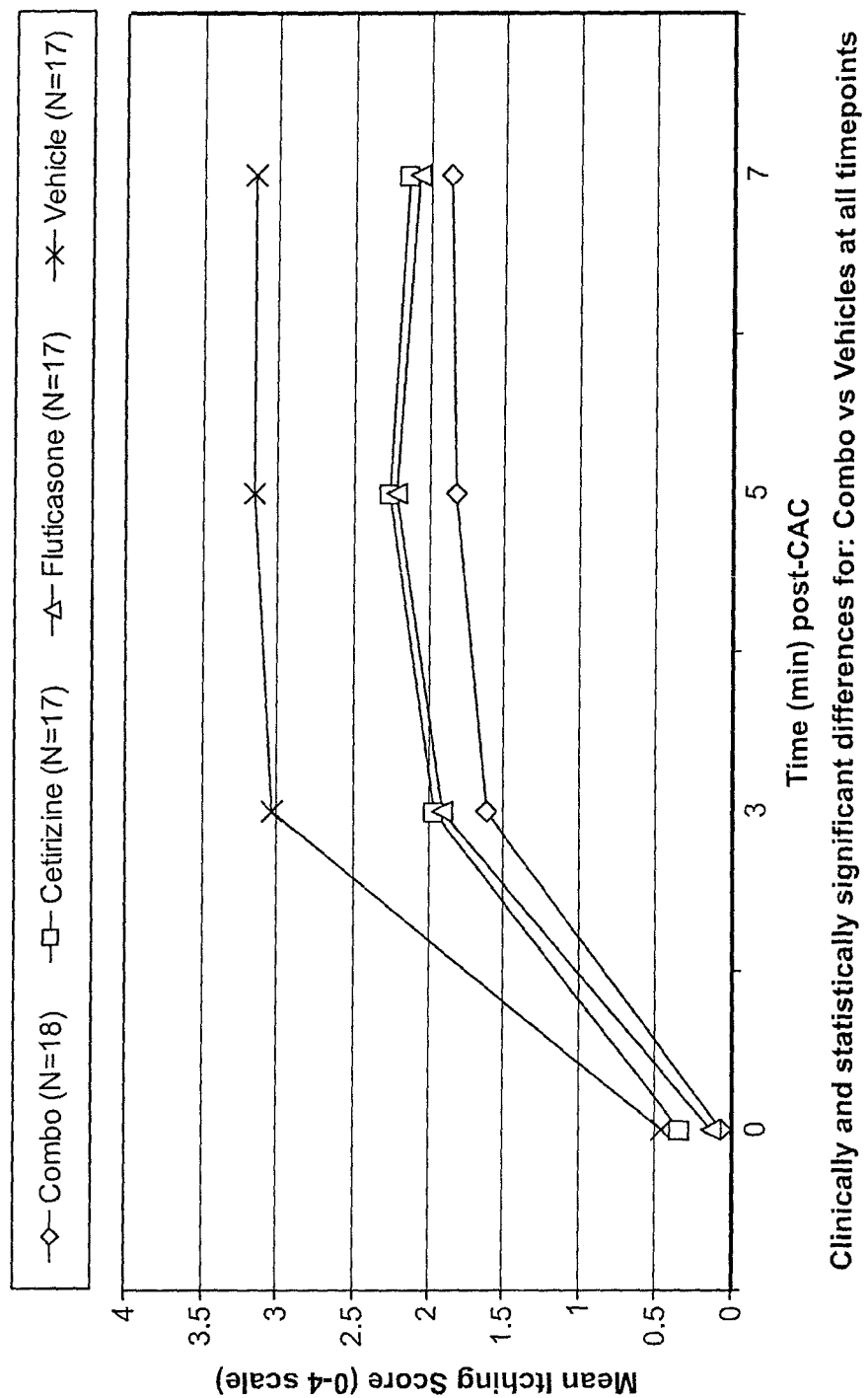
FIG. 31 is a line graph depicting the mean itching score at visit 4A post CAC for a 0.1% cetirizine/0.005% fluticasone formulation (low dose), 0.1% cetirizine alone formulation, 0.005% fluticasone alone formulation, and a vehicle control.
Figure 32:
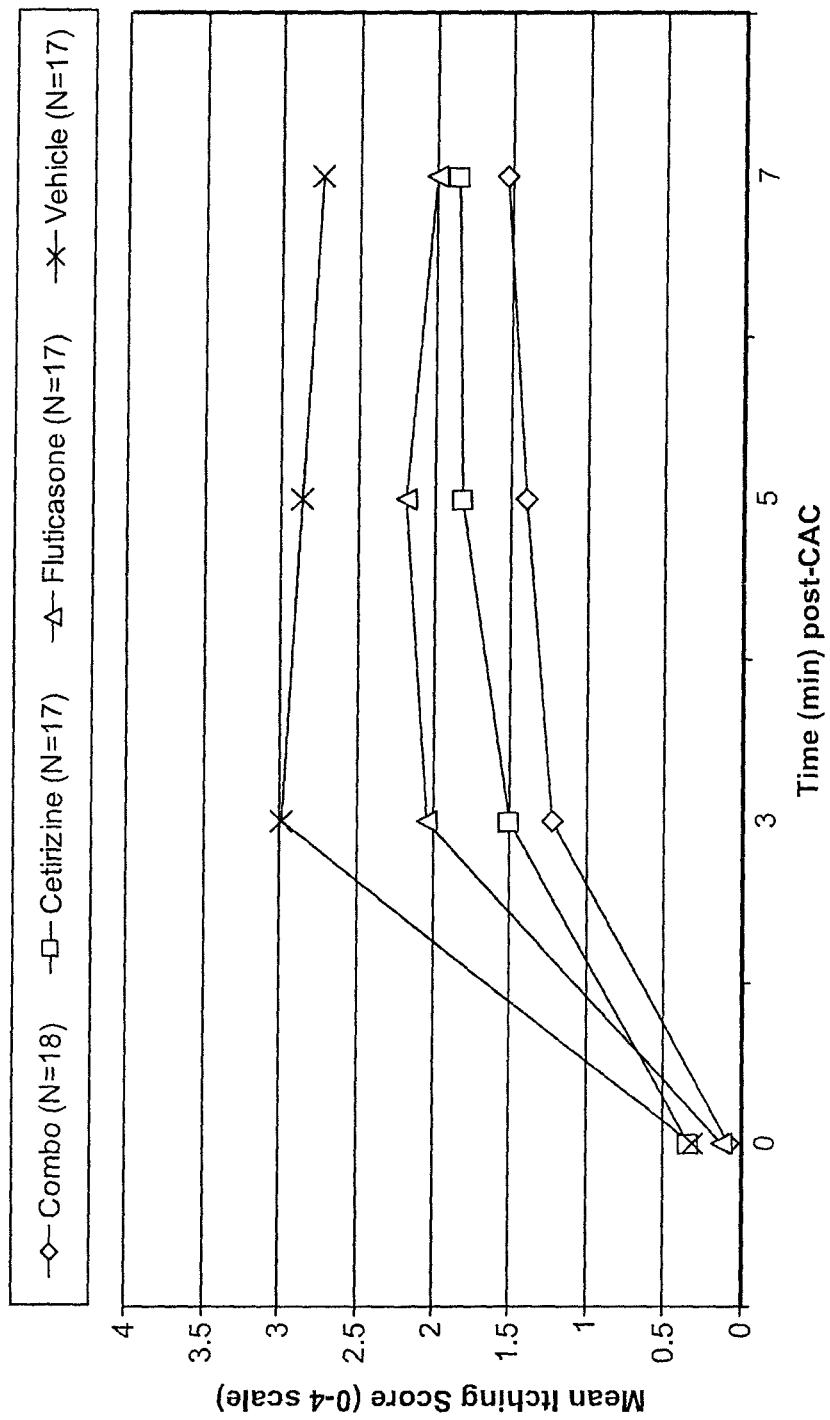
FIG. 32 is a line graph depicting the mean itching score at visit 4B post CAC for a 0.1% cetirizine/0.005% fluticasone formulation (low dose), 0.1% cetirizine alone formulation, 0.005% fluticasone alone formulation, and a vehicle control.
Figure 33:
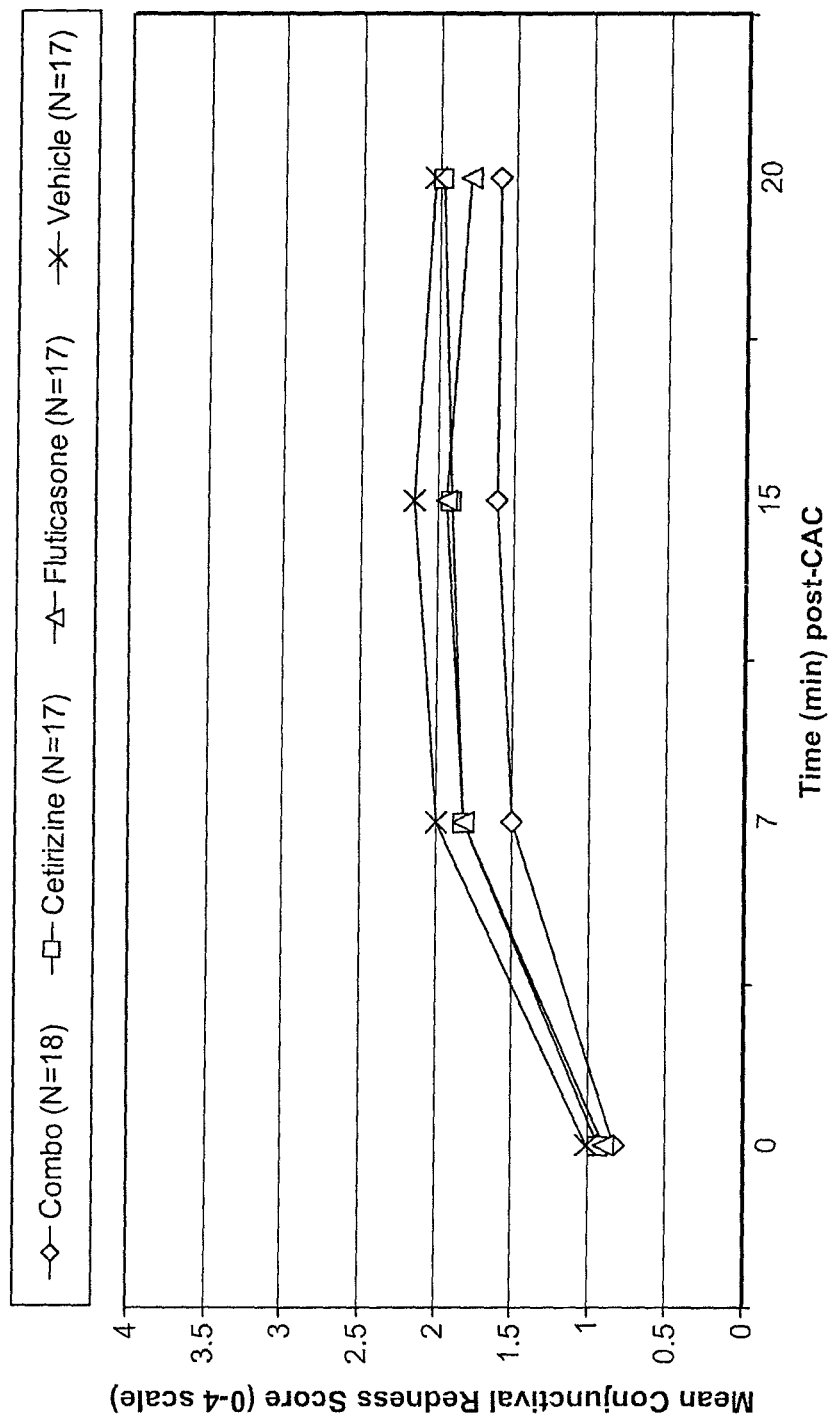
FIG. 33 is a line graph depicting the mean conjunctival redness score at visit 4Apost CAC for a 0.1% cetirizine/ 0.005% fluticasone formulation (low dose), 0.1% cetirizine alone formulation, 0.005% fluticasone alone formulation, and a vehicle control.
Figure 34:
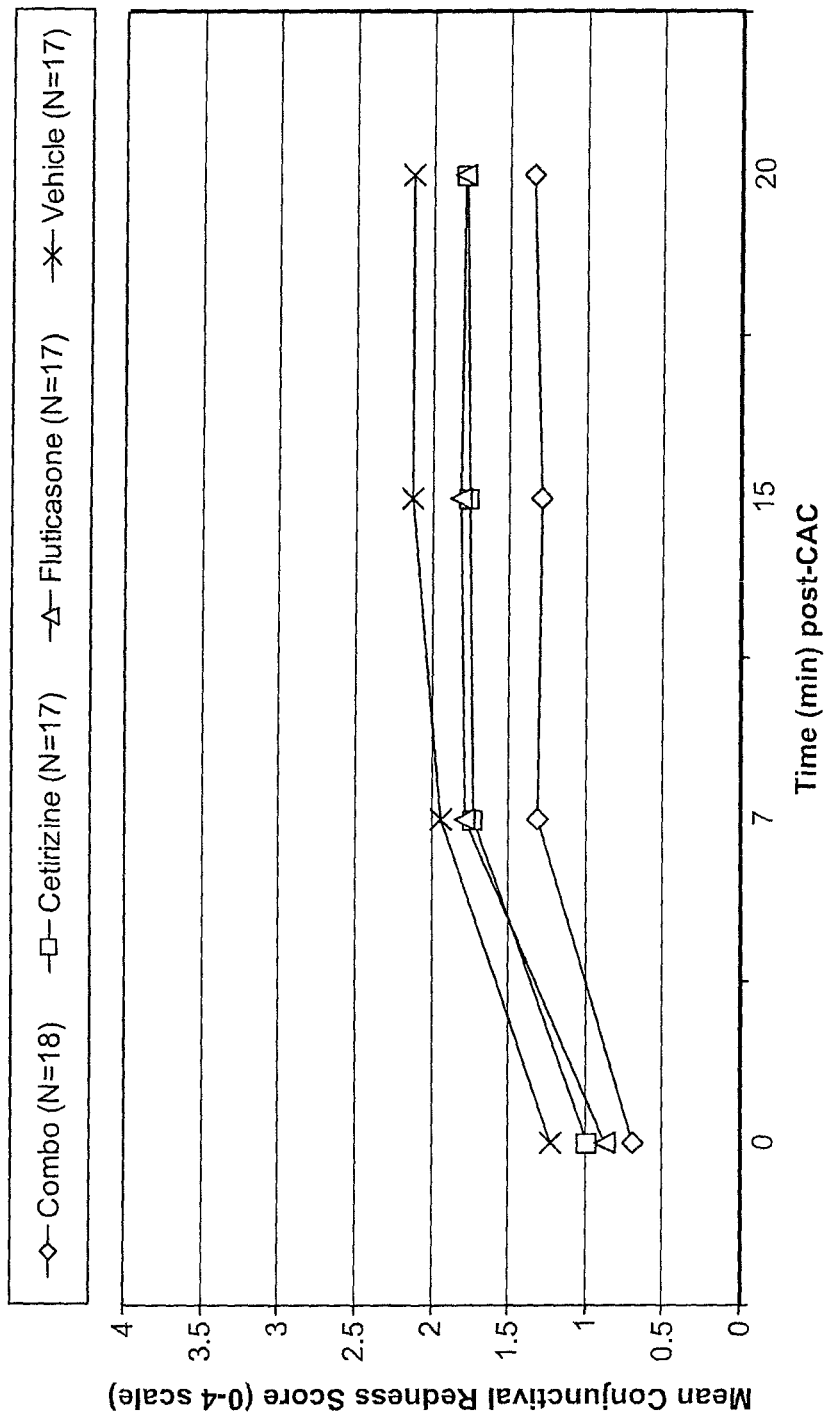
FIG. 34 is a line graph depicting the mean conjunctival redness score at visit 4B post CAC for a 0.1% cetirizine/ 0.005% fluticasone formulation (low dose), 0.1% cetirizine alone formulation, 0.005% fluticasone alone formulation, and a vehicle control.
Figure 36:
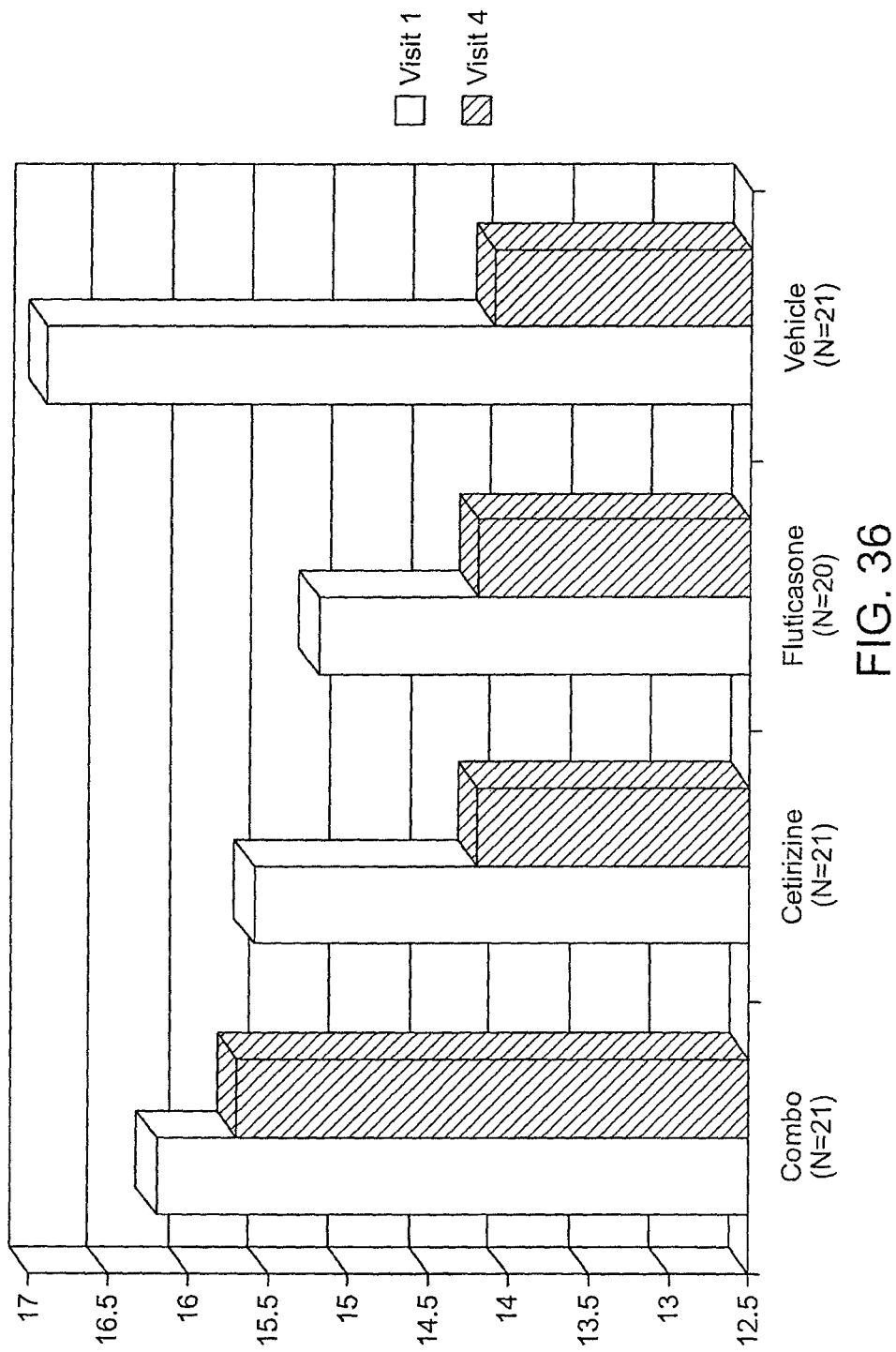
FIG. 36 is a bar chart depicting interocular pressure (IOP) at visit 1 and visit 4 for a 0.1% cetirizine/0.005% fluticasone formulation (low dose) 0.1% cetirizine alone formulation, 0.005% fluticasone alone formulation, and a vehicle control.
Figure 37:
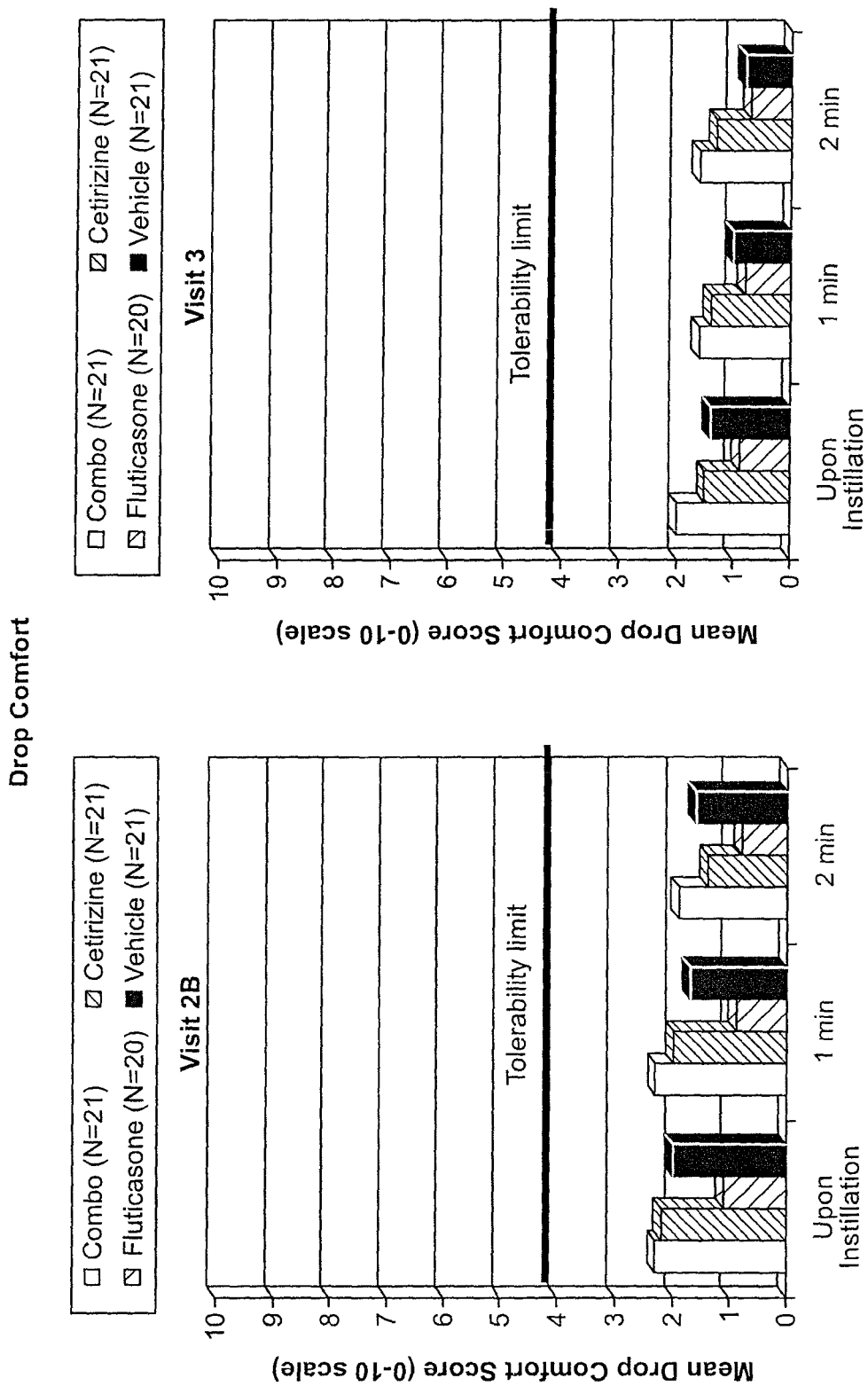
FIG. 37 are bar charts depicting the comfort profile of 0.1% cetirizine/0.005% fluticasone formulation (low dose), 0.1% cetirizine alone formulation, 0.005% fluticasone alone formulation, and a vehicle control. The comfort of the formulation is indicated on a subjective scale of 0 to 10 (0=very comfortable; 10=very uncomfortable).
Figure 38:
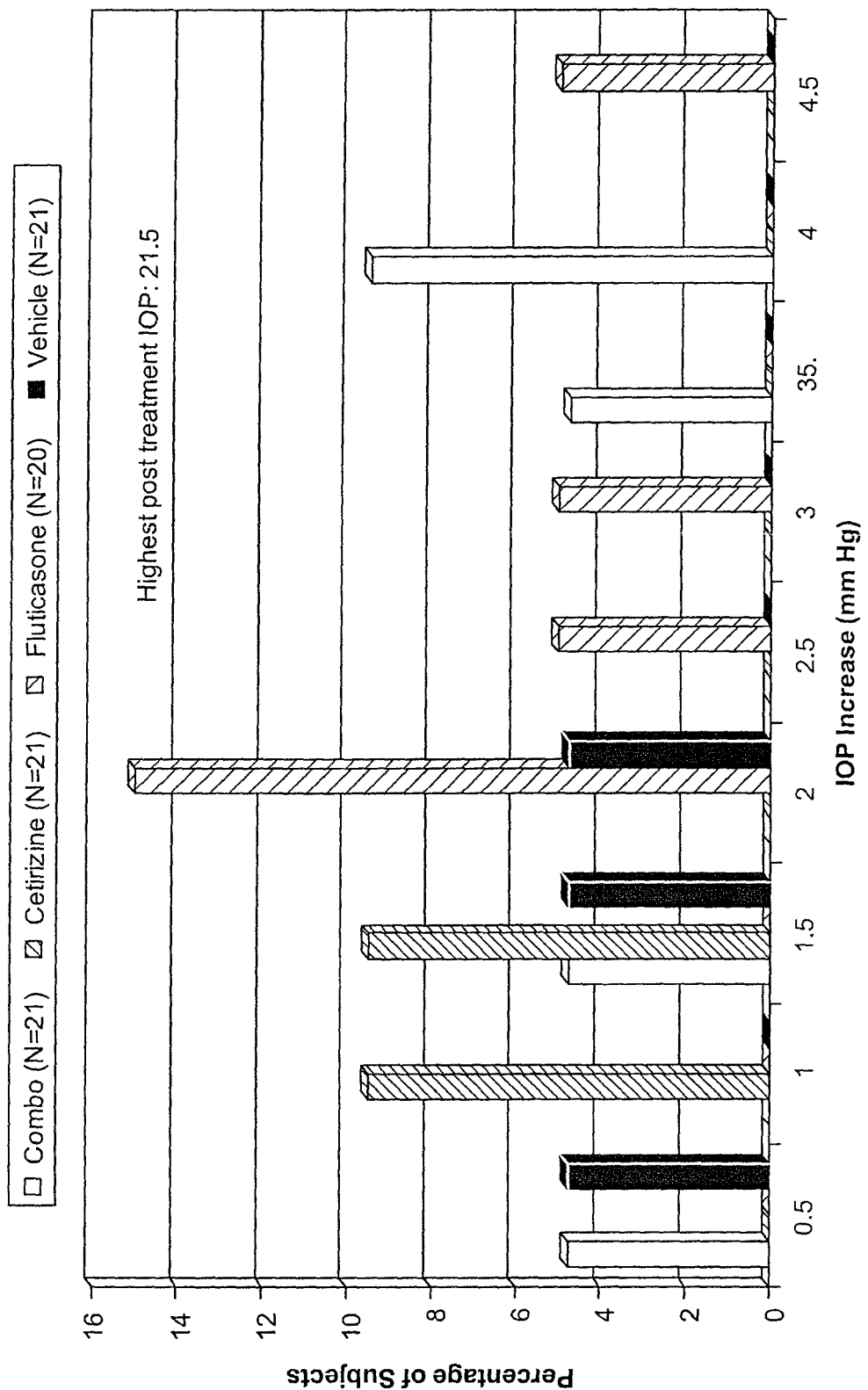
FIG. 38 is a bar chart depicting interocular pressure (IOP) distribution by treatment group. Subjects were treated with 0.1% cetirizine/0.005% fluticasone formulation (low dose), 0.1% cetirizine alone formulation, 0.005% fluticasone alone formulation, and a vehicle control.
Figure 39:
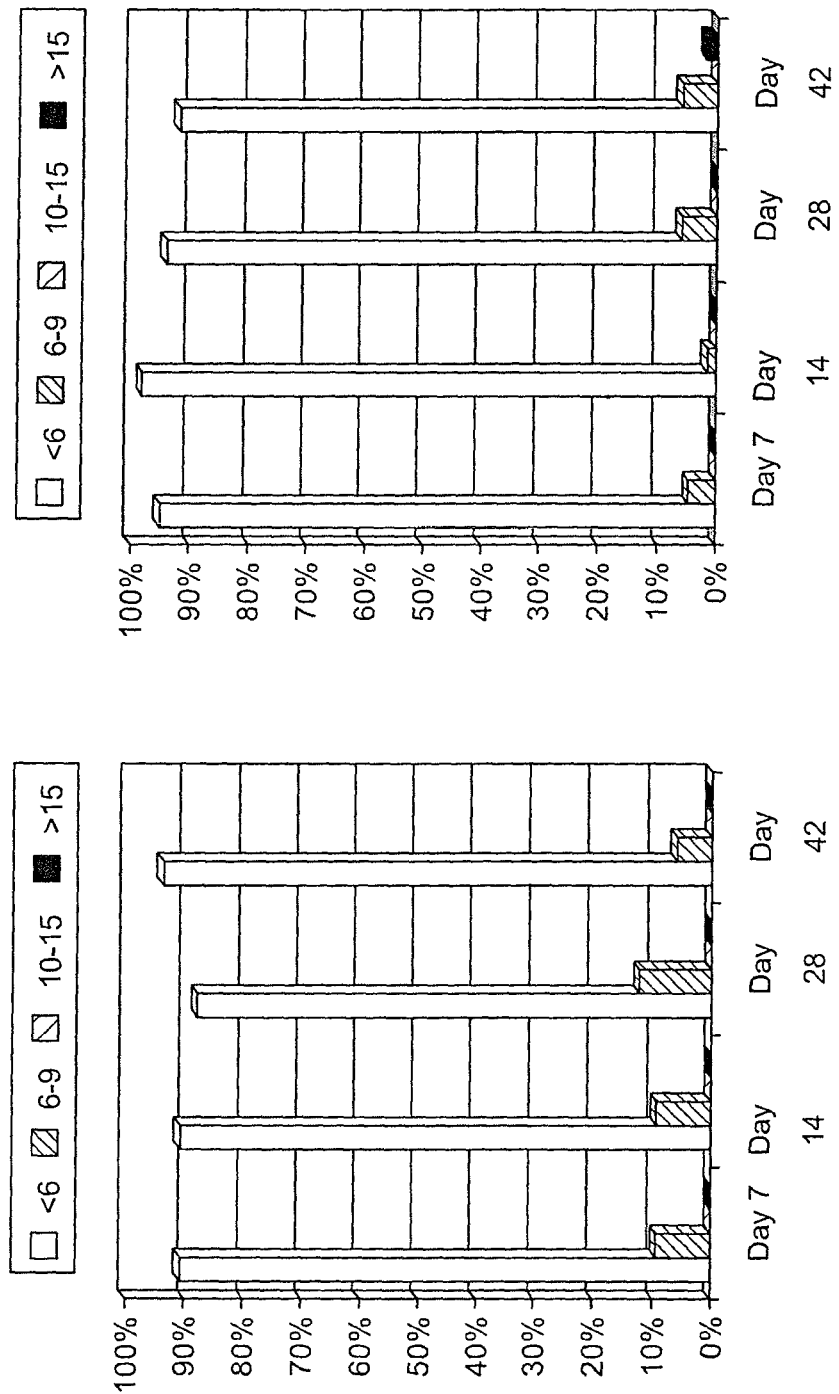
FIG. 39 is a bar chart depicting interocular pressure (IOP) elevation upon treatment with Alrex.

One drop of masked study medication was instilled in each eye and subjects were asked to assess the comfort of the drop on a subjective scale of 0 to 10 (0=comfortable, 10=very uncomfortable (Note: The most uncomfortable commercially available allergy drop=4). The results are shown in FIG. 29. Both the low dose and high dose formulations were well tolerated (average comfort score <3) and were found to be more comfortable than the formulation comprising 0.005% fluticasone alone as the only active agent, which had an osmolality of 900 mOsm/kg (average comfort score ~3; See FIGS. 20-21, Example 2).

Example 5

Stability of 0.10% Cetirizine Formulation and Combined Cetirizine/Fluticasone Formulations Tables 8-9 below show that a 0.1% formulation of cetirizine was stable for at least three months both at room temperature (Table 6) and at higher temperatures (Table 7).

Tables 10-11 below show that a 0.1% cetirizine/0.005% fluticasone formulation (in 1% Polyethylene Glycol 400, NF; 0.2% Dibasic Sodium Phosphate, Anhydrous, USP; 0.25% Hypromellose, USP; 0.1% Polysorbate 80, NF; 1.8% Glycerin, USP; 0.025% Edetate Disodium, USP; 0.01% Benzalkonium Chloride, NF (pH 7.0); i.e., the formulation listed in Table 5) was stable for at least one month at both room temperature (Table 8) and at higher temperature (Table 9) when stored upright.

Tables 12 and 13 show that a 0.25% cetirizine/0.01% fluticasone formulation (in 1% Polyethylene Glycol 400, NF; 0.2% Dibasic Sodium Phosphate, Anhydrous, USP; 0.25% Hypromellose, USP; 0.1% Polysorbate 80, NF; 1.8% Glycerin, USP; 0.025% Edetate Disodium, USP; 0.01% Benzalkonium Chloride, NF (pH 7.0); i.e., the formulation listed in Table 6) was stable for at least one month at room temperature (Table 10) and at a higher temperature (Table 11) when stored upright.

Cetirizine and fluticasone concentrations were quantified by high pressure liquid chromatography (HPLC). Impurities are shown as "relative retention time" or RRT in the table, which relates the unknown peak to the elution time of the parent peak, cetirizine (or fluticasone). At no time did the total impurities exceed 1%. Sterility, particulate matter, and preservative efficacy were determined only at the initial time point because these should remain unchanged provided that the sealed container is not compromised.

The data herein demonstrates cetirizine and cetirizine/fluticasone formulations that are stable without the inclusion of a cyclodextrin or other solubilizing compound. Without intending to be bound by any theory, the stability was achieved by minimizing/excluding the addition of counter ions or metal based buffers that could promote salt formation, precipitation, or metal based degradation.

TABLE 8

Cetirizine 0.10%/Benzalkonium Chloride 0.01% (w/v) Ophthalmic Solution Stability Testing: 25° C./60% RH (QA Oct. 13, 2008)
Lot #: 04262008@18

| Test | Limits/Specification | Initial Jun. 9, 2008 | 1 Month Jul. 9, 2008 | 2 Month Aug. 11, 2008 | 3 Month Sep. 10, 2008 |
|---|---|---|---|---|---|
| Appearance (Contents) | Clear and colorless to slightly yellow solution | Conforms: Clear, Colorless Solution | Conforms: Clear, Colorless Solution | Conforms: Clear, Colorless Solution | Conforms: Clear, Colorless Solution |
| Appearance (Container Integrity) | No leakage observed, container intact | Conforms: No leakage, container intact | Conforms: No leakage, container intact | Conforms: No leakage, container intact | Conforms: No leakage, container intact |
| Assay: Cetirizine Label Claim: 0.10% (w/v) (equivalent to Cetirizine dihydrochloride 0.1188%) | NLT 90.0% and NMT 110.0% of Label Claim (LC) | 99.2% LC | 99.5% LC | 99.7% LC | 99.4% LC |
| Assay of Ketotifen Impurities (Total, | Absence of Active Report individual ≥0.05% | Not Detected RRT @ 0.93: 0.06% | Not Detected RRT @ 0.90: 0.06% | Not Detected RRT @ 0.67: 0.07% | Not Detected RRT @ 0.63: 0.09% |

TABLE 8-continued

Cetirizine 0.10%/Benzalkonium Chloride 0.01% (w/v) Ophthalmic Solution Stability Testing: 25° C./60% RH (QA Oct. 13, 2008)
Lot #: 04262008@18

| Test | Limits/Specification | Initial Jun. 9, 2008 | 1 Month Jul. 9, 2008 | 2 Month Aug. 11, 2008 | 3 Month Sep. 10, 2008 |
|---|---|---|---|---|---|
| Ketotifen impurities, | Report Total | RRT @ 1.1: 0.15% | RRT @ 1.60: 0.06% | RRT @ 0.91: 0.06% | RRT @ 0.92: 0.05% |
| Cetirizine impurities) | | Total: 0.2% | RRT @ 2.11: 0.06% | RRT @ 1.10: 0.05% | RRT @ 1.08: 0.05% |
| | | | Total: 0.2% | RRT @ 1.11: 0.09% | RRT @ 1.10: 0.09% |
| | | | | RRT @ 2.33: 0.06% | RRT @ 1.56: 0.08% |
| | | | | Total: 0.30%% | Total: 0.40%% |
| Assay: Benzalkonium Chloride Label Claim: 0.01% (w/v) | NLT 85.0% and NMT 115% of Label Claim | 99.4% LC | 94.6% LC | 100.0% LC | 94.7% LC |
| pH | 5.5 ± 0.5 | 5.7 | 6.0 | 6.0 | 5.9 |
| Osmolality | Report | 253 mOsm/Kg · H$_2$0 | 253 mOsm/Kg · H$_2$0 | 253 mOsm/Kg · H$_2$0 | 252 mOsm/Kg · H$_2$0 |
| Sterility | Meets USP Criteria | Pass | | | |
| Particulate Matter | Number of particles with diameter of: ≥10 μm: NMT 50/mL ≥25 μm: NMT 5/mL ≥50 μm: NMT 2/mL | Pass | | | |
| Antimicrobial Preservative Efficacy | Report | Pass | | | |

TABLE 9

Cetirizine 0.10%/Benzalkonium Chloride 0.01% (w/v) Ophthalmic Solution Stability Testing: 40° C./75% RH (QA Oct. 13, 2008)
(Lot #: 04262008@18)

| Test | Limits/Specification | Initial Jun. 9, 2008 | 1 Month Jul. 9, 2008 | 2 Month Aug. 11, 2008 | 3 Month Sep. 10, 2008 |
|---|---|---|---|---|---|
| Appearance (Contents) | Clear and colorless to slightly yellow solution | Conforms: Clear, Colorless Solution | Conforms: Clear, Colorless Solution | Conforms: Clear, Colorless Solution | Conforms: Clear, Colorless Solution |
| Appearance (Container Integrity) | No leakage observed, container intact | Conforms: No leakage, container intact | Conforms: No leakage, container intact | Conforms: No leakage, container intact | Conforms: No leakage, container intact |
| Assay: Cetirizine Label Claim: 0.10% (w/v) (equivalent to Cetirizine dihydrochloride 0.1188%) | NLT 90.0% and NMT 110.0% of Label Claim (LC) | 99.2% LC | 99.6% LC | 100.1% LC | 99.4% LC |
| Assay of Ketotifen | Absence of Active | Not Detected | Not Detected | Not Detected | Not Detected |
| Impurities (Total, Ketotifen impurities, | Report individual ≥0.05% Report Total | RRT @ 0.93: 0.06% RRT @ 1.1: 0.15% | RRT @ 0.90: 0.06% RRT @ 2.11: 0.06% | RRT @ 0.67: 0.34% RRT @ 0.78: 0.05% | RRT @ 0.63: 0.44% RRT @ 0.92: 0.05% |
| Cetirizine impurities) | | Total: 0.2% | Total: 0.1% | RRT @ 0.91: 0.06% | RRT @ 1.10: 0.09% |
| | | | | RRT @ 1.10: 0.05% | Total: 0.6% |
| | | | | RRT @ 1.11: 0.09% | |
| | | | | RRT @ 2.33: 0.06% | |
| | | | | Total: 0.70%% | |
| Assay: Benzalkonium Chloride Label Claim: 0.01% (w/v) | NLT 85.0% and NMT 115% of Label Claim | 99.4% LC | 92.9% LC | 99.1% LC | 96.8% LC |
| pH | 5.5 ± 0.5 | 5.7 | 6.0 | 5.9 | 5.7 |
| Osmolality | Report | 253 mOsm/Kg · H$_2$0 | 254 mOsm/Kg · H$_2$0 | 254 mOsm/Kg · H$_2$0 | 255 mOsm/Kg · H$_2$0 |
| Sterility | Meets USP Criteria | Pass | | | |
| Particulate Matter | Number of particles with diameter of: ≥10 μm: NMT 50/mL ≥25 μm: NMT 5/mL ≥50 μm: NMT 2/mL | Pass | | | |
| Antimicrobial Preservative Efficacy | Report | Pass | | | |

TABLE 10

0.005% Fluticasone Propionate/0.1% Cetirizine Ophthalmic Suspension Stability Testing: 25° C./40% RH
(Lot Number: Ora091202.V1)

| Test Date Pulled | Specification | Initial 12/15/09 Inverted Orientation | 1 Week 12/21/09 Inverted Orientation | 2 Week 12/28/09 Inverted Orientation | 2 Week 01/04/10 Upright Orientation | 1 Month 01/13/10 Upright Orientation |
|---|---|---|---|---|---|---|
| Appearance (Solution) | Report Results | Clear, Colorless, no ppt. | Clear, Colorless, no ppt. | Clear, Colorless, no ppt. | NT | Slightly Turbid Solution |
| Appearance (Container) | No leakage observed, container intact | NT | No leakage observed, container intact | No leakage observed, container intact | NT | No leakage observed, container intact |
| Fluticasone Propionate Assay | 90%-110% Label Claim | 95.1% LC | 98.6% LC | 89.4% LC* | 102.4% LC | 99.6% LC |
| Fluticasone Related Substances | Report individual % AUC, Report total, % AUC | RRT 0.19: 0.75% AUC RRT 0.36: 0.35% AUC Total: 1.07% AUC | RRT 0.19: 0.50% AUC RRT 0.36: 0.40% AUC RRT 0.66: 0.24% AUC RRT 0.93: 0.07% AUC Total: 1.21% | RRT 0.09: 0.06% AUC RRT 0.10: 0.14% AUC RRT 0.12: 0.72% AUC RRT 0.27: 0.49% AUC RRT 0.33: 0.18% AUC RRT 0.52: 0.05% AUC RRT 0.61: 0.29% AUC RRT 0.76: 0.23% AUC RRT 0.88: 0.27% AUC Total: 2.43% | RRT 0.07: 0.25% AUC RRT 0.09: 0.06% AUC RRT 0.10: 0.16% AUC RRT 0.12: 0.53% AUC RRT 0.27: 0.46% AUC RRT 0.33: 0.14% AUC Total: 1.6% | RRT 0.12: 0.39% AUC RRT 0.14: 0.63% AUC RRT 0.29: 0.41% AUC RRT 0.34: 0.10% AUC Total: 1.53% AUC |
| Cetirizine Assay | 90%-110% Label Claim | 98.6% LC | 97.2% LC | 98.0% LC | NT | 96.5% LC |
| Cetirizine Related Substances | Report individual % AUC, Report total, % AUC | RRT 0.96: 0.5% AUC RRT 1.13: 0.08% AUC Total: 0.13% | RRT 0.96: 0.05% AUC RRT 1.13: 0.18% AUC Total: 0.23% | RRT 0.96: 0.05% AUC RRT 1.13: 0.19% AUC Total: 0.24% | NT | RRT 1.13: 0.53% AUC Total: 0.53% AUC |
| Benzalkonium chloride Assay | 50%-150% Label Claim | 99.5% LC | NT | NT | NT | 101.0% LC |
| Disodium Edetate | 70%-120% Label Claim | 95.8% LC | NT | NT | NT | 91.2% LC |
| pH | 6.5-7.8 | 7.1 | 7.0 | 7.0 | NT | 7.0 |
| Osmolality | Report results | 291 mOsm/Kg | 290 mOsm/Kg | 291 mOsm/Kg | NT | 290 mOsm/Kg |

RH = relative humidity,
LC = label claim,
AUC = area under curve,
NT = not tested.
*The low assay values were attributed to the inverted orientation in which the stability samples were stored. Samples stored in the upright orientation were tested at the 2-week time point and subsequent time points, as reflected in the data shown.

TABLE 11

0.005% Fluticasone Propionate/0.1% Cetirizine Ophthalmic Suspension Stability Testing: 40° C./NMT 25% RH
(Lot Number: Ora091202.V1)

| Test | Specification | Initial Dec. 15, 2009 Inverted Orientation | 2 Week Dec. 28, 2009 Inverted Orientation | 2 Week Jan. 04, 2010 Upright Orientation | 1 Month Jan. 13, 2010 Upright Orientation |
|---|---|---|---|---|---|
| Appearance (Solution) | Report Results | Clear, Colorless, no ppt. | Clear, Colorless, no ppt. | NT | Slightly turbid solution |
| Appearance (Container) | No leakage observed, container intact | NT | No leakage observed, Container intact | NT | No leakage observed, container intact |
| Fluticasone Propionate Assay | 90%-110% Label Claim | 95.1% LC | 58.4% LC* | 103.2% LC | 101.4% LC |
| Fluticasone Related Substances | Report individual % AUC, | RRT 0.19: 0.75% AUC RRT 0.36: 0.35% AUC | RRT 0.09: 0.66% AUC RRT 0.10: 0.59% AUC | RRT 0.07: 0.26% AUC RRT 0.09: 0.52% AUC | RRT 0.11: 0.69% AUC RRT 0.14: 0.59% AUC |
| | Report total, % AUC | Total: 1.07% AUC | RRT 0.12: 0.72% AUC RRT 0.28: 0.72% AUC | RRT 0.10: 0.13% AUC RRT 0.12: 0.35% AUC | RRT 0.29: 0.35% AUC RRT 0.34: 0.60% AUC |

TABLE 11-continued 0.005% Fluticasone Propionate/0.1% Cetirizine Ophthalmic Suspension Stability Testing: 40° C./NMT 25% RH
(Lot Number: Ora091202.V1)

|  |  | Initial | 2 Week | 2 Week | 1 Month |
|---|---|---|---|---|---|
|  |  |  | Date Pulled |  |  |
| Test | Specification | Dec. 15, 2009 Inverted Orientation | Dec. 28, 2009 Inverted Orientation | Jan. 04, 2010 Upright Orientation | Jan. 13, 2010 Upright Orientation |
|  |  |  | RRT 0.33: 1.12% AUC<br>RRT 0.45: 0.20% AUC<br>RRT 0.49: 0.11% AUC | RRT 0.27: 0.43% AUC<br>RRT 0.33: 0.19% AUC<br>RRT 0.76: 0.06% AUC | Total: 2.23% AUC |
|  |  |  | RRT 0.53: 0.14% AUC<br>RRT 0.60: 0.14% AUC<br>RRT 0.76: 0.31% AUC<br>RRT 0.88: 0.49% AUC | Total: 2.02% |  |
|  |  |  | Total: 5.20% |  |  |
| Cetirizine Assay | 90%-110% Label Claim | 98.6% LC | 97.9% LC | NT | 96.8% LC |
| Cetirizine Related Substances | Report individual % AUC, Report total, % AUC | RRT 0.96: 0.5% AUC<br>RRT 1.13: 0.08% AUC<br>Total: 0.13% | RRT 1.13: 0.48% AUC<br>Total: 0.48% | NT | RRT 1.13: 0.82% AUC<br>Total: 0.82% AUC |
| Benzalkonium chloride Assay | 50%-150% Label Claim | 99.5% LC | NT | NT | 101.3% LC |
| Disodium Edetate | 70%-120% Label Claim | 95.8% LC | NT | NT | 91.0% LC |
| pH | 6.5-7.8 | 7.1 | 7.0 | NT | 7.0 |
| Osmolality | Report results | 291 mOsm/Kg | 293 mOsm/Kg | NT | 291 mOsm/Kg |

RH = relative humidity, LC = label claim, AUC = area under curve, NT = not tested.
*The low assay values were attributed to the inverted orientation in which the stability samples were stored. Samples stored in the upright orientation were tested at the 2-week time point and subsequent time points, as reflected in the data shown.

TABLE 12

0.01% Fluticasone Propionate/0.25% Cetirizine Ophthalmic Suspension Stability Testing: 25° C./40% RH
(Lot Number: Ora091130.V1)

| Test Date Pulled | Specification | Initial 12/15/09 Inverted Orientation | 1 Week 12/21/09 Inverted Orientation | 2 Week 12/28/09 Inverted Orientation | 2 Week 01/04/10 Upright Orientation | 1 Month 01/13/10 Upright Orientation |
|---|---|---|---|---|---|---|
| Appearance (Solution) | Report Results | Clear, Colorless no ppt. | Clear, Colorless no ppt | Clear, Colorless no ppt | NT | Slightly turbid solution |
| Appearance (Container) | No leakage observed, container intact | NT | No leakage observed, container intact | No leakage observed, container intact | NT | No leakage observed, container intact |
| Fluticasone Propionate Assay | 90%-110% Label Claim | 96.9% LC | 98.9% LC | 79.0% LC* | 99.6% LC | 99.2% LC |
| Test Date Pulled | Initial Specification Inverted Orientation | 1 Week 12/15/09 Inverted Orientation | 2 Week 12/21/09 Inverted Orientation | 2 Week 12/28/09 Upright | 1 Month 01/04/10 Upright Orientation | 01/13/10 |
| Fluticasone Related Substances | Report individual % AUC, Report total, % AUC | RRT 0.18: 0.82% AUC<br>RRT 0.35: 0.40% AUC<br>Total: 1.22% | RRT 0.19: 0.61% AUC<br>RRT 0.35: 0.47% AUC<br>RRT 0.67: 0.43% AUC<br>Total: 1.51% | RRT 0.06: 0.36% AUC<br>RRT 0.09: 0.38% AUC<br>RRT 0.12: 0.82% AUC<br>RRT 0.27: 0.67% AUC<br>RRT 0.33: 0.20% AUC<br>RRT 0.44: 0.31% AUC<br>RRT 0.51: 0.42% AUC<br>RRT 0.60: 0.27% AUC<br>RRT 0.76: 1.04% AUC<br>RRT 0.88: 1.48% AUC<br>Total: 6.14% | RRT 0.06: 0.49% AUC<br>RRT 0.09: 0.38% AUC<br>RRT 0.12: 0.66% AUC<br>RRT 0.27: 0.53% AUC<br>RRT 0.36: 0.20% AUC<br>RRT 0.52: 0.09% AUC<br>Total: 2.35% | RRT 0.11: 0.46% AUC<br>RRT 0.13: 0.74% AUC<br>RRT 0.29: 0.50% AUC<br>Total: 1.17% AUC |

TABLE 12-continued 0.01% Fluticasone Propionate/0.25% Cetirizine Ophthalmic Suspension Stability Testing: 25° C./40% RH
(Lot Number: Ora091130.V1)

| Test Date Pulled | Specification | Initial 12/15/09 Inverted Orientation | 1 Week 12/21/09 Inverted Orientation | 2 Week 12/28/09 Inverted Orientation | 2 Week 01/04/10 Upright Orientation | 1 Month 01/13/10 Upright Orientation |
|---|---|---|---|---|---|---|
| Cetirizine Assay | 90%-110% Label Claim | 99.3% LC | 97.3% LC | 98.7% LC | NT | 97.2% LC |
| Cetirizine Related Substances | Report individual % AUC, Report total, % AUC | RRT 0.96: 0.05% AUC RRT 1.13: 0.14% AUC Total: 0.19% | RRT 0.96: 0.05% AUC RRT 1.13: 0.31% AUC Total: 0.36% | RRT 0.96: 0.05% AUC RRT 1.13: 0.32% AUC Total: 0.37% | NT | RRT 1.13: 0.75% AUC Total: 0.75% AUC |
| Benzalkonium chloride Assay | 50%-150% Label Claim | 96.7% LC | NT | NT | NT | 100.6% LC |
| Disodium Edetate | 70%-120% Label Claim | 92.9% LC | NT | NT | NT | 89.7% LC |
| pH | 6.5-7.8 | 7.1 | 7.1 | 7.1 | NT | 7.1 |
| Osmolality | Report results | 272 mOsm/Kg | 273 mOsm/Kg | 274 mosm/Kg | NT | 273 mOsm/Kg |

RH = relative humidity,
LC = label claim,
AUC = area under curve,
NT = not tested.
*The low assay values were attributed to the inverted orientation in which the stability samples were stored. Samples stored in the upright orientation were tested at the 2-week time point and subsequent time points, as reflected in the data shown.

TABLE 13

0.01% Fluticasone Propionate/0.25% Cetirizine Ophthalmic Suspension Stability Testing: 40° C./NMT 25% RH
(Lot Number: Ora091130.V1)

| Test Date Pulled | Specification | Initial 12/15/09 Inverted Orientation | 1 Week 12/21/09 Inverted Orientation | 2 Week 12/28/09 Inverted Orientation | 2 Week 01/04/10 Upright Orientation | 1 Month 01/13/10 Upright Orientation |
|---|---|---|---|---|---|---|
| Appearance (Solution) | Report Results | Clear, Colorless, no ppt. | Clear, colorless, no ppt | Clear, colorless, no ppt | NT | Slightly turbid solution |
| Appearance (Container) | No leakage observed, container intact | NT | No leakage observed, container intact | No leakage observed, container intact | NT | No leakage observed, container intact |
| Fluticasone Propionate Assay | 90%-110% Label Claim | 96.9% LC | 98.5% LC | 51.4% LC* | 100.4% LC | 98.9% LC |
| Fluticasone Related Substances | Report individual % AUC, Report total, % AUC | RRT 0.18: 0.82% AUC RRT 0.35: 0.40% AUC Total: 1.22% | RRT 0.19: 0.47% AUC RRT 0.35: 0.49% AUC RRT 0.66: 0.38% AUC Total: 1.34% | RRT 0.09: 1.09% AUC RRT 0.10: 0.43% AUC RRT 0.12: 0.73% AUC RRT 0.27: 0.97% AUC RRT 0.32: 0.56% AUC RRT 0.44: 0.24% AUC RRT 0.51: 0.67% AUC RRT 0.60: 0.30% AUC RRT 0.76: 0.99% AUC RRT 0.88: 1.32% AUC Total: 7.54% | RRT 0.06: 0.44% AUC RRT 0.09: 0.93% AUC RRT 0.12: 0.53% AUC RRT 0.27: 0.52% AUC RRT 0.31: 0.07% AUC RRT 0.36: 0.17% AUC Total: 2.66% | RRT 0.11: 0.94% AUC RRT 0.13: 0.71% AUC RRT 0.28: 0.08% AUC Total: 1.73% AUC |
| Cetirizine Assay | 90%-110% Label Claim | 99.3% LC | 97.1% LC | 98.6% LC | NT | 96.7% LC |
| Cetirizine Related Substances | Report individual % AUC, Report total, % AUC | RRT 0.96: 0.05% AUC RRT 1.13: 0.14% AUC Total: 0.19% | RRT 0.46: 0.08% AUC RRT 1.13: 0.69% AUC Total: 0.77% | RRT 0.46: 0.08% AUC RRT 1.13: 0.70% AUC Total: 0.78% | NT | RRT 1.13: 0.96% AUC Total: 0.96% AUC |
| Benzalkonium chloride Assay | 50%-150% Label Claim | 96.7% LC | NT | NT | NT | 98.7% LC |
| Disodium Edetate | 70%-120% Label Claim | 92.9% LC | NT | NT | NT | 90.4% LC |

TABLE 13-continued 0.01% Fluticasone Propionate/0.25% Cetirizine Ophthalmic Suspension Stability Testing: 40° C./NMT 25% RH
(Lot Number: Ora091130.V1)

| Test Date Pulled | Specification | Initial 12/15/09 Inverted Orientation | 1 Week 12/21/09 Inverted Orientation | 2 Week 12/28/09 Inverted Orientation | 2 Week 01/04/10 Upright Orientation | 1 Month 01/13/10 Upright Orientation |
|---|---|---|---|---|---|---|
| pH | 6.5-7.8 | 7.1 | 7.1 | 7.1 | NT | 7.0 |
| Osmolality | Report results | 272 mOsm/Kg | 273 mOsm/Kg | 272 mOsm/Kg | NT | 274 mOsm/Kg |

RH = relative humidity,
LC = label claim,
AUC = area under curve,
NT = not tested.
*The low assay values were attributed to the inverted orientation in which the stability samples were stored. Samples stored in the upright orientation were tested at the 2-week time point and subsequent time points, as reflected in the data shown.

Example 6

Clinical Efficacy of Cetirizine/Fluticasone Formulations

The purpose of this example was to evaluate the efficacy of cetirizine 0.1%/fluticasone 0.005% ophthalmic suspension compared to cetirizine 0.1% ophthalmic suspension, fluticasone 0.005% ophthalmic suspension and vehicle in the prevention of the signs and symptoms of allergic conjunctivitis in a modified CAC model.

A multi-center, double-masked, randomized, vehicle-controlled, parallel treatment comparison study was conducted on approximately 80 subjects age 10 and older with a history of allergic conjunctivitis, and with a best corrected visual acuity of 0.7 logMAR or better in each eye. The conjunctival allergen challenge (CAC) model was used for screening purposes and to reproducibly exacerbate subject's signs and symptoms of allergic conjunctivitis.

The study was conducted during allergy season and comprised 4 visits over a period of 3 weeks including a 1-week period of QD dosing with assigned study medication. A modification of the CAC model that incorporates 3 CACs over a 2-day period was used to evaluate the effectiveness of the study medication on both the acute and the chronic components of the allergic reaction. The drug challenge CAC sequence was carried out prior to, and following, 1-week of QD dosing with assigned study medication.

The study comprised 4 visits conducted over a period of approximately 3 weeks.

Summary of Visit Schedule

Visit 1 (Day −1): Allergen titration
Visit 2A (Day 0): Allergen confirmation;
Visit 2B (Day 0): 8 hour re-challenge; Randomization; In-office dose
 Subjects self-administer assigned study medication, QD (days 1-12)
Visit 3 (Day 13): In-office dose 15 mins prior to challenge;
Visit 4A (Day 14): In-office dose 30 mins after challenge;
Visit 4B (Day 14): 8 hour re-challenge; Exit Visit 1 (Day −1), Allergen Titration: subjects meeting all entry criteria were challenged with particular allergens in increasing concentrations. Within 10 minutes of each allergen instillation, conjunctival redness and ocular itching were assessed using a 9-point scale (0 to 4, with 0.5-unit increments allowed). Any subject who failed to demonstrate an adequate CAC reaction at baseline was excluded from the study.

Visit 2 (Day −0), Visit 2 was divided into 2 separate visits 8 hours apart.

Visit 2A, Allergen Confirmation: the CAC was repeated to verify the reproducibility of the ocular itching and conjunctival redness responses. Itching was subject-evaluated at 3, 5, and 7 minutes post-CAC. Redness and chemosis were graded by the investigator at 7, 15 and 20 minutes post-CAC. The subject graded lid swelling, watery eyes, rhinorrhea, nasal pruritis, nasal congestion, and ear or palate pruritis at 7, 15, and 20 minutes post-CAC.

Visit 2B, Rechallenge/Randomization: the CAC was repeated after the initial CAC at Visit 2A. Itching was subject-evaluated at 3, 5, and 7 minutes post-CAC. Redness and chemosis were graded by the investigator at 7, 15 and 20 minutes post-CAC. The subject graded lid swelling, watery eyes, rhinorrhea, nasal pruritis, nasal congestion, and ear or palate pruritis at 7, 15, and 20 minutes post-CAC. Any subject who failed to demonstrate an adequate CAC reaction at baseline was excluded from the study.

Qualified subjects were randomized, in a 1:1:1:1 ratio, into 4 groups: 1) cetirizine 0.1%/fluticasone 0.005% ophthalmic suspension (combo), 2) cetirizine 0.1% ophthalmic suspension, 3) fluticasone 0.005% ophthalmic suspension, 4) Vehicle of combo (placebo). Subjects received the first dose of study medication at approximately 30 minutes post-CAC. Subjects continued QD dosing at home for the 2 weeks between Visit 2 and Visit 3. Subjects recorded ocular and nasal symptoms in daily diaries.

Visit 3 (Day 13), Drug Efficacy CAC: assigned study medication was instilled in-office minutes prior to CAC. Itching was subject-evaluated at 3, 5, and 7 minutes post-CAC. Redness and chemosis were graded by the investigator at 7, 15 and 20 minutes post-CAC. The subject graded lid swelling, watery eyes, rhinorrhea, nasal pruritis, nasal congestion, and ear or palate pruritis at 7, 15, and 20 minutes post-CAC.

Visit 4 (Day 14), Visit 4 was divided into 2 separate visits.

Visit 4A, Drug Efficacy CAC: The CAC was repeated after the Visit 3 dose of assigned study medication. Itching was subject-evaluated at 3, 5, and 7 minutes post-CAC. Redness and chemosis were graded by the investigator at 7, 15 and 20 minutes post-CAC. The subject graded lid swelling, watery eyes, rhinorrhea, nasal pruritis, nasal congestion, and ear or palate pruritis at 7, 15, and 20 minutes post-CAC.

Visit 4B, 8-hour Rechallenge: the CAC was repeated after the initial CAC at Visit 4A. Itching was subject-evaluated at 3, 5, and 7 minutes post-CAC. Redness and chemosis were graded by the investigator at 7, 15 and 20 minutes post-CAC. The subject graded lid swelling, watery eyes, rhinorrhea, nasal pruritis, nasal congestion, and ear or palate pruritis at 7, 15, and 20 minutes post-CAC.

Primary Efficacy Endpoints

The primary efficacy endpoints were ocular itching and conjunctival redness, evaluated at Visit 3, Visit 4A, and Visit 4B.

Subjects evaluated ocular itching at 3, 5, and 7 minutes post CAC. Ocular itching was assessed by the subject using the scale and descriptors using the standard 0-4 scale. The investigator evaluated conjunctival redness at 7, 15, and 20 minutes post CAC. Conjunctival redness was assessed by the standard 0-4 scale Severity scales for both measures were based on a 5-point (9-step) scale with half-unit (1-step) increments allowed. The average score of both eyes from each subject was the value used for further comparisons among the combination ophthalmic suspension, the 2 components individually, and the vehicle control.

Secondary Efficacy Measurements

All secondary efficacy measures were evaluated at Visit 3, Visit 4A and Visit 4B.

Ciliary redness and episcleral redness were evaluated by the investigator at 7, 15, and 20 minutes post-CAC using a 5-point (9-step) scale.

Chemosis was evaluated by the investigator at 7, 15 and 20 minutes post-CAC using a 5-point (9-step) scale.

Lid swelling was evaluated by the subject at 7, 15, and 20 minutes post-CAC using a 4-point (0-3) scale.

Tearing/watery eyes was evaluated by the subject at 7, 15, and 20 minutes post-CAC using a 5-point (0-4) scale.

Rhinorrhea (rhinorrhea, nasal pruritis, ear or palate pruritis, and nasal congestion) was evaluated by the subject at 7, 15, and 20 minutes post-CAC using a 5-point (0-4) scale.

Nasal pruritis was evaluated by the subject at 7, 15, and 20 minutes post-CAC using a 5-point (0-4) scale.

Ear or palate pruritis was evaluated by the subject at 7, 15, and 20 minutes post-CAC using a 5-point (0-4) scale.

Nasal congestion was evaluated by the subject at 7, 15, and 20 minutes post-CAC using a 5-point (0-4) scale.

Diary scores (daily morning and evening assessments performed by the subject): (0-4 scale for all)

Ocular
  ocular itching
  ocular redness
  eyelid swelling
  tearing/watery eyes Nasal
  nasal itching
  nasal congestion
  runny nose
  ear/palate itching Safety Measurements The safety measurements were:

Visual Acuity: Visual acuity (best corrected if necessary) was measured using an ETDRS chart. Visual acuity was evaluated at the beginning of each study visit (i.e. prior to slit lamp examination). At Visit 4B, in addition to the baseline visual acuity measurement, an additional measurement was performed post-CAC as part of the safety exit evaluation.

Slit Lamp Biomicroscopy: Slit-lamp biomicroscopy was used to examine the lids, conjunctiva, cornea, lens, and anterior chamber. Examinations were conducted at the beginning of each study visit. At Visit 4B, in addition to the baseline slit lamp examination, an additional examination was performed post-CAC as part of the safety exit evaluation.

Tolerability Measures: All subjects were asked to complete a 2-part Drop Assessment Questionnaire.

Subject Reported prop Comfort: Subjects were asked to rate the comfort of the drop in each eye upon instillation, at 1 minute, and at 2 minutes after instillation of study medication. The assessment used a 10-point scale with 0 as very comfortable and 10 as very uncomfortable.

Description of Drop Comfort: Subjects were asked to choose 3 words (from a list of 12) that described how each drop felt in the eye. The assessment was performed for each eye at 3 minutes after instillation of study medication. Subjects were also able to write their own descriptor if they chose to do so.

Dilated Ophthalmoscopy: Dilated ophthalmoscopy was used to examine the vitreous, retina, macula, choroid and optic nerve. Examinations were conducted post-CAC at Visit 1 and post-CAC at Visit 4B as part of the safety exit examination.

Intraocular Pressure: IOP was measured using applanation tonometry with a Goldmann tonometer according to the manufacturer's instructions. IOP measurements were performed post-CAC at Visit 1 and post-CAC at Visit 4B as part of the safety exit examination.

Pregnancy Test: A pregnancy test was performed on all females of childbearing potential at Visit 1, prior to enrollment and instillation of study drug, and pre-CAC at Visit 4B.

Digital Photographs: Digital photographs were taken of both eyes at Visit 4B pre- and post-CAC.

Adverse Events: All adverse events, regardless of relationship to the study drug, were monitored and reported throughout the entire course of the study. Adverse events were to be recorded on the source document and, when applicable, on the adverse event form of the case report form.

Statistical Methods

Hierarchical statistical hypothesis testing was performed at a significance level of 0.05 to control type I error in the case that only one endpoint was significant. The primary efficacy variables were compared between Combo treated eyes and Vehicle treated eyes in the following order: 1) There is difference in ocular itching between Combo and Vehicle treated eyes. 2) There is difference in conjunctival redness between Combo and Vehicle treated eyes.

All hypotheses testing was two-sided and performed at type I error (a) of 0.05. Specific statistical tests are described below.

Analysis Populations:

The Intent-to-Treat (ITT) population consisted of subjects who were randomized. All data was included and no subjects were excluded because of protocol violations. The ITT population was analyzed as randomized and was used for efficacy analyses. Missing data was imputed using LOCF for this population. For sensitivity analysis, Markov Chain Monte Carlo (MCMC) imputation was also applied.

The Per Protocol (PP) was a subset of the ITT population and consisted of subjects who completed all four visits with no major protocol violations. This population was analyzed as treated using observed data only and was used for confirmatory analyses.

The Safety population included all randomized subjects who received at least one dose of any investigational treatment. The Safety population was analyzed as treated and was used for safety analyses; no data exclusion was allowed for any reason.

Demographic Data:

The demographic data was summarized for each treatment group and for overall subjects. Medical history was summarized separately for ocular and non-ocular data for each treatment group. All baseline characteristic data was summarized using ITT population.

Primary Efficacy Variables:

For the primary efficacy variables, descriptive statistics, such as, number of subjects, mean, standard deviation, minimum, maximum, and median for the primary efficacy variables were summarized by visit, time point and treatment group. In order to demonstrate efficacy, for all post-CAC assessments using ITT population with LOCF, the mean difference of ocular itching and conjunctival redness scores between the Combo treated eyes and Vehicle treated eyes were compared using a parametric two-sample t-test, at a two-sided significance level of 0.05. The non-parametric Wilcoxon rank sum test and an analysis of covariance (ANCOVA) model with treatment effects accounting for repeated measurements with baseline adjustment were performed as supportive analyses. Assessments measured at Visit 3 pre-CAC were used as baseline in the ANCOVA model. Least Square Means (LS Means) for each treatment, the corresponding 95% confidence intervals, and the estimated treatment difference between the Combo treated eyes and Vehicle treated eyes were calculated from this ANCOVA model. For sensitivity analysis, the ITT population was analyzed with Markov Chain Monte Carlo (MCMC) imputation implemented using the MI procedure within SAS®. A supportive analysis was also performed on the per protocol population with observed data only. The mean difference between the Combo treated eyes and its individual component treated eyes was analyzed in a similar manner.

Secondary Efficacy Variables:

For the secondary efficacy variables, analyses were performed in a manner similar to primary endpoints, for both the ITT population with observed data only and the per protocol population.

Diary Data:

Diary data was analyzed to assess any environmental treatment effect. The score of each ocular symptom and nasal symptom was summarized using descriptive statistics (number of subjects, mean, standard deviation, minimum, maximum, and median) by assessment time, day, and treatment. The mean difference between Combo treated eyes and Vehicle treated eyes was tested using a two-sample t-test and the non-parametric Wilcoxon rank sum test at a significance level of 0.05. For a given symptom, Combo treated eyes must have had statistically significantly lower mean symptom severity scores on the majority of days (7 out of 12 days) compared to Vehicle treated eyes in order to claim superiority. The mean difference between the Combo treated eyes and its individual component treated eyes were analyzed in a similar manner.

In addition, an analysis of covariance (ANCOVA) was applied to analyze the overall diary mean scores (Day 1-Day 12). Treatment effect, diary day, and pollen count by site were considered as covariates in the model with adjustment for repeated measurements within subject. Least Square Means (LS Means) for each treatment, the corresponding 95% confidence intervals, and the estimated treatment difference between test article and control were calculated from this ANCOVA model. All analyses of diary data were conducted on the ITT population with observed data only. In addition, the same statistical analyses were conducted on the per protocol population.

Safety Analyses:

All safety analyses were performed on the safety population. Descriptive statistics (number of observations, mean, median, standard deviation, minimum, and maximum) were provided for visual acuity and intraocular pressure. Frequencies and percentages were provided for categorical variables in slit lamp biomicroscopy and dilated ophthalmoscopy.

Adverse events were coded to a system organ class and preferred term using the Medical Dictionary for Regulatory Activities, version 12.1 (MedDRA). Frequencies and percentages were provided per treatment group for treatment-emergent adverse events (TEAEs), serious TEAEs, and TEAE causing premature discontinuation. An adverse event was treatment emergent if it occurred or worsened after the first dose of study treatment up through Day 14. All adverse events were assigned a severity grade of mild, moderate, or severe. Furthermore, frequencies were given for subjects with TEAEs by: system organ class; system organ class and preferred term; system organ class, preferred term and maximal severity; system organ class, preferred term and strongest relationship. AEs were classified as either being related to treatment or not related. AEs related to treatment were to include AEs classified as definite, probable, possible or unknown. AEs classified as not related or unlikely were considered unrelated.

Tolerability Variables:

The tolerability variables were analyzed for the ITT population. Drop comfort was summarized using mean, median, standard deviation, minimum and maximum and was analyzed using a two-sample t-test to compare Combo group to its components and Vehicle groups. Drop descriptor assessment were summarized using counts and percentages and were analyzed using Fisher's exact test or Chi-Square as appropriate to compare Combo group to its components and Vehicle groups.

Efficacy Results

All efficacy analyses were performed on data collected at Visits 3, 4A, and 4B. Primary and secondary efficacy analyses were performed on both the ITT population and the PP population.

ITT population:

Eighty three (83) subjects were randomized at Visit 2B and comprised the ITT population. No subjects were excluded from the ITT population because of protocol violations. The ITT population was analyzed as randomized; all data were included. Missing data were imputed using the last observation carried forward method (LOCF) for the ITT population.

PP Population:

The PP population was a subset of the ITT population and consisted of subjects who completed all four visits with no major protocol violations. This population was analyzed as treated using observed data only and was used for confirmatory analyses. Fourteen (14) subjects in the ITT population were excluded from the PP population; 12 of these subjects did not complete the study.

All safety analyses were performed on the safety population.

Safety population:

The Safety population included all randomized subjects who received at least one dose of any investigational treatment. All 83 subjects randomized at Visit 2B also received their first dose of assigned study medication post CAC at Visit 2B, and thus comprise the Safety population. The Safety population was analyzed as treated; no data exclusion was allowed for any reason.

Criteria for Effectiveness

The study design allowed the evaluation of three aspects of the allergic reaction.

Early Allergic Reaction:
Onset of Action (Visit 3, CAC administered 15 min after Visit 3 dose)
Early Allergic Reaction:
Duration of Action (Visit 4A, CAC administered 16 hours after Visit 3 dose, Visit 4 dose given 30 min after the CAC)
Late Inflammatory Reaction:
(Visit 4B, no dose at Visit 4B, CAC administered 8 hours after Visit 4A dose)

The primary clinical efficacy evaluation of this study was the determination of superiority of cetirizine 0.1%/fluticasone 0.005% ophthalmic suspension (Combo) over the Vehicle. A mean difference of 1.0 unit was considered clinically significant at a single time point. In order to demonstrate efficacy at a single visit, Combo-treated eyes must have shown statistical and clinical superiority over Vehicle-treated eyes by at least 0.5 units on a 5-point scale at all post-CAC time points and at least 1 unit at a majority (i.e., 2 out of 3) of post-CAC time points. At each post-CAC time point, a treatment difference was considered statistically significant if it was significant at a two-sided significance level of 0.05.

Primary Efficacy Endpoints

The primary efficacy measures were ocular itching (at 3, 5, and 7 minutes post-CAC) and conjunctival redness (at 7, 15, and 20 minutes post-CAC).

Table 14 presents an overview of the Active treatments (Combo, cetirizine 0.1%, fluticasne 0.005%) vs Vehicle data for the primary and secondary CAC data. The shadings in the individual cells represent the endpoints for which the comparisons of Active treatment to Vehicle were clinically significant, statistically significant-only, or trending towards statistical significance (0.05<P<0.10). The numbers within the cells represent the treatment difference from the ANCOVA model (LS mean Active minus LS mean Vehicle).

Table 15 thru 26 present the details of the comparisons between Combo and the active components, as well as between Combo and Vehicle, for ocular itching and for conjunctival redness in both the ITT with LOCF population and the PP population at study Visits 3, 4A, and 4B.

Combo demonstrated clinical efficacy in the prevention of ocular itching. The mean itching scores for Combo were significantly lower (P<0.05) than vehicle at all 3 time points at all 3 visits (Visits 3, 4A and 4B). The treatment differences (Combo mean minus Vehicle mean) were greater than 1 unit at all 3 time points at all 3 visits. See Tables 14-20 for the detailed ocular itching data in the ITT with LOCF population and the PP populations at Visits 3, 4A, and 4B.

Combo demonstrated statistical superiority over vehicle in the prevention of conjunctival redness. The mean conjunctival redness scores for Combo were significantly lower (P<0.05) than vehicle at all 3 time points at all 3 visits. The magnitude of the treatment differences (Combo mean minus Vehicle mean) was greater than 0.5 units, but less than 1 unit, for all 3 time points at Visits 3 and 4B, and for 2 of the 3 time points at Visit 4A. See Tables 21-26 for the detailed conjunctival redness data in the ITT with LOCF population and the PP populations at Visits 3, 4A, and 4B.

Combo demonstrated statistical superiority over cetirizine in the prevention of conjunctival redness at all 3 time points of Visit 4B (PP population). See Table 26 for the detailed conjunctival redness data in the PP population at Visit 4B.

Combo demonstrated statistically superiority over fluticasone in the prevention of ocular itching (Visit 3 and Visit 4B) and in the prevention of conjunctival redness (Visit 3 and Visit 4B). See Tables 15, 16, 19, and 20 for the details of the ocular itching data. See Tables 21, 22, 25, and 26 for the details of the conjunctival redness data.

Secondary Efficacy Endpoints (CAC Data)

Results for all of the secondary efficacy assessments at the Visit 3, Visit 4A, and Visit 4B CAC studies are summarized in Table 25, Combo demonstrated clinical efficacy in the prevention of lid swelling. The mean lid swelling scores for Combo were significantly lower (P<0.05) than vehicle at all 3 time points at all 3 visits (Visits 3, 4A and 4B). The treatment differences (Combo mean minus Vehicle mean) were greater than 0.5 unit at all 3 time points at all 3 visits, and greater than 1.0 unit for at least 2 out of 3 time points at all 3 visits. See Tables 29-31 for the detailed lid swelling data in the PP population at Visits 3, 4A, and 4B, respectively.

TABLE 14

Overview of CAC data

| Parameter | Combo: Visit 3 Onset | Cetirizine Visit 3 Onset | Fluticasone Visit 3 Onset | Combo: Visit 4A Duration | Cetirizine: Visit 4A Duration | Fluticasone: Visit 4A Duration | Combo: Visit 4B Late | Cetirizine Visit 4B Late | Fluticasone: Visit 4B Late |
|---|---|---|---|---|---|---|---|---|---|
| Ocular Itching | -1.76 | -1.70 | -0.77 | -1.37 | -1.04 | -1.11 | -1.48 | -1.18 | -0.84 |
| Conj. Red | -0.62 | | | -0.46 | | | -0.69 | -0.31 | |
| Cil. Red | -0.70 | | | -0.57 | | -0.33 | -0.95 | -0.43 | -0.40 |
| Epi. Red | -0.63 | | | -0.61 | | | -0.74 | -0.48 | |
| Total Red | -1.92 | | | -1.62 | | | -2.36 | -1.23 | -0.93 |
| Chemosis | -0.30 | -0.29 | | | | | | | |
| Lid Swelling | -1.10 | -0.70 | | -1.00 | | -0.40 | -1.10 | -0.70 | -0.50 |
| Tearing | -0.50 | | | -0.60 | | | -0.80 | | |
| Nasal Itch | -0.50 | -0.60 | | | | | -0.50 | -0.50 | |
| Rhinorrh. | -0.60 | | | | | | -0.60 | | |
| Congest. | -0.70 | -0.60 | | -0.60 | | | -0.60 | | |
| Ear/Palate Itch | -0.90 | -1.10 | -0.80 | -1.00 | -0.90 | -1.00 | -0.90 | -0.60 | -0.70 |

TABLE 14-continued

Overview of CAC data

LEGEND
- Clinically significant and P < 0.05
- P < 0.05
- 0.05 < P < 0.10

Numbers within cells represent the treatment differences calculated with the ANCOVA model
(LS mean active minus LS mean Vehicle).

TABLE 15

Ocular Itching, Visit 3, 15-min Onset of Action, ITT Population with LOCF

| Time Point | 1.1.1.1.1 Combo (N = 21) | 1.1.1.1.2 Cetirizine 0.1% (N = 21) | Fluticasone 0.005% (N = 20) | 1.1.1.1.3 Vehicle 1.1.1.1.4 (N = 21) |
|---|---|---|---|---|
| Pre-CAC | | | | |
| N | 20 | 20 | 19 | 19 |
| mean (SD) | 0.06 (0.228) | 0.20 (0.616) | 0.11 (0.459) | 0.13 (0.403) |
| 3 min post-CAC | | | | |
| N | 20 | 19 | 18 | 18 |
| mean (SD) | 1.33 (0.974) | 0.99 (0.752) | 2.11 (1.173) | 2.90 (0.967) |
| P value[1] | — | 0.2315 | 0.0324 | <0.0001 |
| P value[2] | — | 0.3486 | 0.0487 | 0.0001 |
| 5 min post CAC | | | | |
| N | 20 | 19 | 18 | 18 |
| mean (SD) | 1.44 (1.076) | 1.33 (0.590) | 2.25 (1.057) | 3.11 (0.944) |
| P value[1] | — | 0.6968 | 0.0246 | <0.0001 |
| P value[2] | — | 0.9662 | 0.0272 | 0.0001 |
| 7 min post-CAC | | | | |
| N | 20 | 19 | 18 | 18 |
| mean (SD) | 1.31 (1.066) | 1.59 (0.894) | 2.03 (1.131) | 2.97 (1.018) |
| P value[1] | — | 0.3800 | 0.0533 | <0.0001 |
| P value[2] | — | 0.4535 | 0.0935 | 0.0001 |
| ANCOVA | | | | |
| LS mean | 1.33 | 1.29 | 2.09 | 2.95 |
| 95% CI | (0.92, 1.75) | (0.86, 1.71) | (1.65, 2.52) | (2.52, 3.38) |
| TRT difference[3] | — | −0.05 | −0.75 | −1.62 |
| P value[4] | — | 0.8719 | 0.0148 | <0.0001 |

[1]P value calculated using a two-sample t-test to compare Combo to Vehicle and to the individual components.
[2]P value calculated using a Wilcoxon rank sum test to compare Combo to Vehicle and to the individual components.
[3]TRT difference: difference in the LS means (Combo LS mean − vehicle LS mean or component LS mean).
[4]P value from the ANCOVA analysis, with treatment and baseline score (Visit 3 pre-CAC) as covariates, comparing Combo to vehicle and to its individual components.

TABLE 16

Ocular Itching, Visit 3, 15-min Onset of Action, PP Population

| Time Point | 1.1.1.1.5 Combo (N = 21) | 1.1.1.1.6 Cetirizine 0.1% (N = 21) | Fluticasone 0.005% (N = 20) | 1.1.1.1.7 Vehicle 1.1.1.1.8 (N = 21) |
|---|---|---|---|---|
| Pre-CAC | | | | |
| N | 18 | 17 | 17 | 17 |
| mean (SD) | 0.07 (0.240) | 0.24 (0.664) | 0.12 (0.485) | 0.15 (0.424) |
| 3 min post-CAC | | | | |
| N | 18 | 17 | 17 | 17 |
| mean (SD) | 1.19 (0.922) | 1.00 (0.795) | 2.24 (1.081) | 2.93 (0.991) |

TABLE 16-continued

Ocular Itching, Visit 3, 15-min Onset of Action, PP Population

| | Group | | | |
|---|---|---|---|---|
| Time Point | 1.1.1.1.5 Combo (N = 21) | 1.1.1.1.6 Cetirizine 0.1% (N = 21) | Fluticasone 0.005% (N = 20) | 1.1.1.1.7 Vehicle 1.1.1.1.8 (N = 21) |
| TRT difference | | | | |
| P value[1] | — | 0.5081 | 0.0045 | <0.0001 |
| P value[2] | — | 0.6520 | 0.0087 | 0.0001 |
| 5 min post CAC | | | | |
| N | 18 | 17 | 17 | 17 |
| mean (SD) | 1.29 (1.030) | 1.31 (0.616) | 2.35 (0.992) | 3.12 (0.973) |
| P value[1] | — | 0.9524 | 0.0039 | <0.0001 |
| P value[2] | — | 0.6654 | 0.0045 | 0.0001 |
| 7 min post-CAC | | | | |
| N | 18 | 17 | 17 | 17 |
| mean (SD) | 1.18 (1.042) | 1.54 (0.936) | 2.12 (1.097) | 2.97 (1.049) |
| P value[1] | — | 0.2851 | 0.0143 | <0.0001 |
| P value[2] | — | 0.2805 | 0.0219 | 0.0001 |
| ANCOVA | | | | |
| LS mean | 1.20 | 1.27 | 2.19 | 2.96 |
| 95% CI | (0.77, 1.63) | (0.82, 1.71) | (1.75, 2.63) | (2.52, 3.40) |
| TRT difference[3] | — | −0.06 | −0.99 | −1.76 |
| P value[4] | — | 0.8719 | 0.0020 | <0.0001 |

[1] P value calculated using a two-sample t-test to compare Combo to Vehicle and to the individual components.
[2] P value calculated using a Wilcoxon rank sum test to compare Combo to Vehicle and to the individual components.
[3] TRT difference: difference in the LS means (Combo LS mean − vehicle LS mean or component LS mean).
[4] P value from the ANCOVA analysis, with treatment and baseline score (Visit 3 pre-CAC) as covariates, comparing Combo to vehicle and to its individual components.

TABLE 17

Ocular Itching, Visit 4A, 16-hr Duration of Action, ITT Population with LOCF

| | Group | | | |
|---|---|---|---|---|
| Time Point | 1.1.1.1.9 Combo (N = 21) | 1.1.1.1.10 Cetirizine 0.1% (N = 21) | Fluticasone 0.005% (N = 20) | 1.1.1.1.11 Vehicle 1.1.1.1.12 (N = 21) |
| Pre-CAC | | | | |
| N | 20 | 20 | 19 | 19 |
| mean (SD) | 0.06 (0.228) | 0.38 (0.651) | 0.12 (0.357) | 0.41 (0.535) |
| 3 min post-CAC | | | | |
| N | 20 | 19 | 18 | 18 |
| mean (SD) | 1.75 (1.112) | 1.92 (1.131) | 1.88 (1.082) | 3.04 (0.693) |
| P value[1] | — | 0.6369 | 0.7277 | 0.0001 |
| P value[2] | — | 0.6402 | 0.7131 | 0.0006 |
| 5 min post CAC | | | | |
| N | 20 | 19 | 18 | 18 |
| mean (SD) | 1.95 (1.160) | 2.24 (0.991) | 2.21 (1.132) | 3.18 (0.706) |
| P value[1] | — | 0.4111 | 0.4920 | 0.0004 |
| P value[2] | — | 0.4889 | 0.6178 | 0.0015 |
| 7 min post-CAC | | | | |
| N | 20 | 19 | 18 | 18 |
| mean (SD) | 1.98 (1.067) | 2.12 (1.156) | 2.11 (1.231) | 3.18 (0.727) |
| P value[1] | — | 0.6899 | 0.7194 | 0.0002 |
| P value[2] | — | 0.8655 | 0.8831 | 0.0005 |
| ANCOVA | | | | |
| LS mean | 1.87 | 2.03 | 2.00 | 3.11 |
| 95% CI | (1.42, 2.31) | (1.57, 2.49) | (1.54, 2.47) | (2.65, 3.58) |

TABLE 17-continued

Ocular Itching, Visit 4A, 16-hr Duration of Action, ITT Population with LOCF

| Time Point | 1.1.1.1.9 Combo (N = 21) | 1.1.1.1.10 Cetirizine 0.1% (N = 21) | Fluticasone 0.005% (N = 20) | 1.1.1.1.11 Vehicle 1.1.1.1.12 (N = 21) |
|---|---|---|---|---|
| TRT difference[3] | — | −0.16 | −0.14 | −1.25 |
| P value[4] | — | 0.6156 | 0.6746 | 0.0003 |

[1]P value calculated using a two-sample t-test to compare Combo to Vehicle and to the individual components.
[2]P value calculated using a Wilcoxon rank sum test to compare Combo to Vehicle and to the individual components.
[3]TRT difference: difference in the LS means (Combo LS mean − vehicle LS mean or component LS mean).
[4]P value from the ANCOVA analysis, with treatment and baseline score (Visit 4A pre-CAC) as covariates, comparing Combo to vehicle and to its individual components.

TABLE 18

Ocular Itching, Visit 4A, 16-hr Duration of Action, PP Population

| Time Point | 1.1.1.1.13 Combo (N = 21) | 1.1.1.1.14 Cetirizine 0.1% (N = 21) | Fluticasone 0.005% (N = 20) | 1.1.1.1.15 Vehicle 1.1.1.1.16 (N = 21) |
|---|---|---|---|---|
| Pre-CAC | | | | |
| N | 18 | 17 | 17 | 17 |
| mean (SD) | 0.07 (0.240) | 0.34 (0.679) | 0.13 (0.376) | 0.46 (0.547) |
| 3 min post-CAC | | | | |
| N | 18 | 17 | 17 | 17 |
| mean (SD) | 1.61 (1.085) | 1.96 (1.187) | 1.90 (1.111) | 3.04 (0.714) |
| P value[1] | — | 0.3772 | 0.4471 | 0.0001 |
| P value[2] | — | 0.3340 | 0.3876 | 0.0004 |
| 5 min post CAC | | | | |
| N | 18 | 17 | 17 | 17 |
| mean (SD) | 1.81 (1.130) | 2.26 (1.033) | 2.22 (1.166) | 3.16 (0.723) |
| P value[1] | — | 0.2179 | 0.2930 | 0.0002 |
| P value[2] | — | 0.2457 | 0.3451 | 0.0009 |
| 7 min post-CAC | | | | |
| N | 18 | 16 | 17 | 17 |
| mean (SD) | 1.86 (1.051) | 2.14 (1.255) | 2.07 (1.259) | 3.16 (0.744) |
| P value[1] | — | 0.4899 | 0.5928 | 0.0002 |
| P value[2] | — | 0.5673 | 0.8032 | 0.0004 |
| ANCOVA | | | | |
| LS mean | 1.74 | 2.07 | 2.00 | 3.11 |
| 95% CI | (1.26, 2.22) | (1.57, 2.56) | (1.51, 2.49) | (2.61, 3.60) |
| TRT difference[3] | — | −0.33 | −0.26 | −1.37 |
| P value[4] | — | 0.3507 | 0.4576 | 0.0002 |

[1]P value calculated using a two-sample t-test to compare Combo to Vehicle and to the individual components.
[2]P value calculated using a Wilcoxon rank sum test to compare Combo to Vehicle and to the individual components.
[3]TRT difference: difference in the LS means (Combo LS mean − vehicle LS mean or component LS mean).
[4]P value from the ANCOVA analysis, with treatment and baseline score (Visit 3 pre-CAC) as covariates, comparing Combo to vehicle and to its individual components.
Source Table 14.2.1.3

TABLE 19

Ocular Itching, Visit 4B, 8-hour Rechallenge, ITT Population with LOCF

| Time Point | 1.1.1.1.17 Combo (N = 21) | 1.1.1.1.18 Cetirizine 0.1% (N = 21) | Fluticasone 0.005% (N = 20) | 1.1.1.1.19 Vehicle 1.1.1.1.20 (N = 21) |
|---|---|---|---|---|
| Pre-CAC | | | | |
| N | 20 | 20 | 19 | 19 |
| mean (SD) | 0.08 (0.245) | 0.38 (0.631) | 0.11 (0.254) | 0.28 (0.463) |

TABLE 19-continued

Ocular Itching, Visit 4B, 8-hour Rechallenge, ITT Population with LOCF

| Time Point | 1.1.1.1.17 Combo (N = 21) | 1.1.1.1.18 Cetirizine 0.1% (N = 21) | Fluticasone 0.005% (N = 20) | 1.1.1.1.19 Vehicle 1.1.1.1.20 (N = 21) |
|---|---|---|---|---|
| 3 min post-CAC | | | | |
| N | 20 | 19 | 18 | 18 |
| mean (SD) | 1.43 (1.007) | 1.53 (0.916) | 2.01 (0.872) | 2.99 (0.627) |
| P value[1] | — | 0.7441 | 0.0613 | <0.0001 |
| P value[2] | — | 0.7344 | 0.0615 | <0.0001 |
| 5 min post CAC | | | | |
| N | 20 | 19 | 18 | 18 |
| mean (SD) | 1.56 (1.022) | 1.83 (0.954) | 2.17 (0.899) | 2.90 (0.703) |
| P value[1] | — | 0.4503 | 0.0605 | <0.0001 |
| P value[2] | — | 0.5061 | 0.0905 | 0.0001 |
| 7 min post-CAC | | | | |
| N | 20 | 19 | 18 | 18 |
| mean (SD) | 1.64 (1.071) | 1.86 (0.925) | 2.03 (0.935) | 2.79 (0.792) |
| P value[1] | — | 0.5006 | 0.2384 | 0.0006 |
| P value[2] | — | 0.7342 | 0.3843 | 0.0010 |
| ANCOVA | | | | |
| LS mean | 1.53 | 1.70 | 2.03 | 2.89 |
| 95% CI | (1.15, 1.92) | (1.30, 2.10) | (1.62, 2.43) | (2.49, 3.29) |
| TRT difference[3] | — | −0.17 | −0.50 | −1.36 |
| P value[4] | — | 0.5500 | 0.0804 | <0.0001 |

[1]P value calculated using a two-sample t-test to compare Combo to Vehicle and to the individual components.
[2]P value calculated using a Wilcoxon rank sum test to compare Combo to Vehicle and to the individual components.
[3]TRT difference: difference in the LS means (Combo LS mean − vehicle LS mean or component LS mean).
[4]P value from the ANCOVA analysis, with treatment and baseline score (Visit 4A pre-CAC) as covariates, comparing Combo to vehicle and to its individual components.
Source Table 14.2.1.1

TABLE 20

Ocular Itching, Visit 4B, 8-hour Rechallenge, PP Population

| Time Point | 1.1.1.1.21 Combo (N = 21) | 1.1.1.1.22 Cetirizine 0.1% (N = 21) | Fluticasone 0.005% (N = 20) | 1.1.1.1.23 Vehicle 1.1.1.1.24 (N = 21) |
|---|---|---|---|---|
| Pre-CAC | | | | |
| N | 18 | 17 | 17 | 17 |
| mean (SD) | 0.08 (0.257) | 0.34 (0.655) | 0.12 (0.267) | 0.31 (0.480) |
| 3 min post-CAC | | | | |
| N | 18 | 17 | 17 | 17 |
| mean (SD) | 1.22 (0.831) | 1.50 (0.964) | 2.04 (0.889) | 2.99 (0.646) |
| P value[1] | — | 0.3694 | 0.0081 | <0.0001 |
| P value[2] | — | 0.4647 | 0.0104 | <0.0001 |
| 5 min post CAC | | | | |
| N | 18 | 17 | 17 | 17 |
| mean (SD) | 1.40 (0.948) | 1.81 (0.994) | 2.18 (0.926) | 2.87 (0.708) |
| P value[1] | — | 0.2255 | 0.0201 | <0.0001 |
| P value[2] | — | 0.3028 | 0.0272 | 0.0001 |
| 7 min post-CAC | | | | |
| N | 18 | 17 | 17 | 17 |
| mean (SD) | 1.54 (1.089) | 1.85 (0.956) | 1.99 (0.946) | 2.75 (0.795) |
| P value[1] | — | 0.3748 | 0.2065 | 0.0007 |
| P value[2] | — | 0.5611 | 0.3427 | 0.0015 |
| ANCOVA | | | | |
| LS mean | 1.38 | 1.68 | 2.02 | 2.87 |
| 95% CI | (0.98, 1.79) | (1.27, 2.10) | (1.61, 2.44) | (2.45, 3.28) |

TABLE 20-continued

Ocular Itching, Visit 4B, 8-hour Rechallenge, PP Population

| | Group | | | |
|---|---|---|---|---|
| Time Point | 1.1.1.1.21 Combo (N = 21) | 1.1.1.1.22 Cetirizine 0.1% (N = 21) | Fluticasone 0.005% (N = 20) | 1.1.1.1.23 Vehicle 1.1.1.1.24 (N = 21) |
| TRT difference[3] | — | −0.30 | −0.64 | −1.48 |
| P value[4] | — | 0.3099 | 0.0307 | <0.0001 |

[1]P value calculated using a two-sample t-test to compare Combo to Vehicle and to the individual components.
[2]P value calculated using a Wilcoxon rank sum test to compare Combo to Vehicle and to the individual components.
[3]TRT difference: difference in the LS means (Combo LS mean − vehicle LS mean or component LS mean).
[4]P value from the ANCOVA analysis, with treatment and baseline score (Visit 3 pre-CAC) as covariates, comparing Combo to vehicle and to its individual components.
Source Table 14.2.1.3

TABLE 21

Conjunctival Redness, Visit 3, 15-min Onset of Action, ITT Population with LOCF

| | Group | | | |
|---|---|---|---|---|
| Time Point | 1.1.1.1.25 Combo (N = 21) | 1.1.1.1.26 Cetirizine 0.1% (N = 21) | Fluticasone 0.005% (N = 20) | 1.1.1.1.27 Vehicle 1.1.1.1.28 (N = 21) |
| Pre-CAC | | | | |
| N | 20 | 20 | 19 | 19 |
| mean (SD) | 0.74 (0.286) | 0.93 (0.514) | 0.84 (0.410) | 0.88 (0.403) |
| 7 min post-CAC | | | | |
| N | 20 | 19 | 18 | 18 |
| mean (SD) | 1.70 (0.677) | 1.97 (0.812) | 2.18 (0.835) | 2.49 (0.639) |
| P value[1] | — | 0.2618 | 0.0615 | 0.0008 |
| P value[2] | — | 0.2700 | 0.0450 | 0.0010 |
| 15 min post CAC | | | | |
| N | 20 | 19 | 18 | 18 |
| mean (SD) | 2.04 (0.704) | 2.25 (0.997) | 2.44 (0.770) | 2.58 (0.733) |
| P value[1] | — | 0.4494 | 0.0991 | 0.0253 |
| P value[2] | — | 0.5249 | 0.1048 | 0.0207 |
| 20 min post-CAC | | | | |
| N | 20 | 19 | 18 | 18 |
| mean (SD) | 2.04 (0.745) | 2.37 (0.980) | 2.51 (0.838) | 2.58 (0.733) |
| P value[1] | — | 0.2453 | 0.0738 | 0.0290 |
| P value[2] | — | 0.1796 | 0.0594 | 0.0182 |
| ANCOVA | | | | |
| LS mean | 1.97 | 2.10 | 2.36 | 2.51 |
| 95% CI | (1.67, 2.27) | (1.79, 2.41) | (2.04, 2.67) | (2.19, 2.82) |
| TRT difference[3] | — | −0.13 | −0.39 | −0.53 |
| P value[4] | — | 0.5520 | 0.0806 | 0.0174 |

[1]P value calculated using a two-sample t-test to compare Combo to Vehicle and to the individual components.
[2]P value calculated using a Wilcoxon rank sum test to compare Combo to Vehicle and to the individual components.
[3]TRT difference: difference in the LS means (Combo LS mean − vehicle LS mean or component LS mean).
[4]P value from the ANCOVA analysis, with treatment and baseline score (Visit 4A pre-CAC) as covariates, comparing Combo to vehicle and to its individual components.
Source Table 14.2.2.1

TABLE 22

Conjunctival Redness, Visit 3, 15-min Onset of Action, PP Population

| | Group | | | |
|---|---|---|---|---|
| Time Point | 1.1.1.1.29 Combo (N = 21) | 1.1.1.1.30 Cetirizine 0.1% (N = 21) | Fluticasone 0.005% (N = 20) | 1.1.1.1.31 Vehicle 1.1.1.1.32 (N = 21) |
| Pre-CAC | | | | |
| N | 18 | 17 | 17 | 17 |
| mean (SD) | 0.75 (0.297) | 0.99 (0.519) | 0.85 (0.424) | 0.90 (0.415) |

TABLE 22-continued

Conjunctival Redness, Visit 3, 15-min Onset of Action, PP Population

| | Group | | | |
|---|---|---|---|---|
| Time Point | 1.1.1.1.29 Combo (N = 21) | 1.1.1.1.30 Cetirizine 0.1% (N = 21) | Fluticasone 0.005% (N = 20) | 1.1.1.1.31 Vehicle 1.1.1.1.32 (N = 21) |
| 7 min post-CAC | | | | |
| N | 18 | 17 | 17 | 17 |
| mean (SD) | 1.65 (0.697) | 2.09 (0.760) | 2.28 (0.744) | 2.50 (0.656) |
| P value[1] | — | 0.0873 | 0.0151 | 0.0008 |
| P value[2] | — | 0.0841 | 0.0157 | 0.0013 |
| 15 min post CAC | | | | |
| N | 18 | 17 | 17 | 17 |
| mean (SD) | 1.97 (0.712) | 2.38 (0.944) | 2.50 (0.755) | 2.62 (0.740) |
| P value[1] | — | 0.1590 | 0.0413 | 0.0130 |
| P value[2] | — | 0.1896 | 0.0330 | 0.0082 |
| 20 min post-CAC | | | | |
| N | 18 | 17 | 17 | 17 |
| mean (SD) | 1.97 (0.757) | 2.50 (0.914) | 2.53 (0.861) | 2.62 (0.740) |
| P value[1] | — | 0.0732 | 0.0509 | 0.0156 |
| P value[2] | — | 0.0428 | 0.0347 | 0.0088 |
| ANCOVA | | | | |
| LS mean | 1.92 | 2.20 | 2.42 | 2.54 |
| 95% CI | (1.60, 2.24) | (1.88, 2.53) | (2.10, 2.75) | (2.22, 2.86) |
| TRT difference[3] | — | −0.28 | −0.50 | −0.62 |
| P value[4] | — | 0.2254 | 0.0298 | 0.0083 |

[1]P value calculated using a two-sample t-test to compare Combo to Vehicle and to the individual components.
[2]P value calculated using a Wilcoxon rank sum test to compare Combo to Vehicle and to the individual components.
[3]TRT difference: difference in the LS means (Combo LS mean − vehicle LS mean or component LS mean).
[4]P value from the ANCOVA analysis, with treatment and baseline score (Visit 3 pre-CAC) as covariates, comparing Combo to vehicle and to its individual components.
Source Table 14.2.2.3

TABLE 23

Conjunctival Redness, Visit 4A, 16-hr Duration of Action, ITT Population with LOCF

| | Group | | | |
|---|---|---|---|---|
| Time Point | 1.1.1.1.33 Combo (N = 21) | 1.1.1.1.34 Cetirizine 0.1% (N = 21) | Fluticasone 0.005% (N = 20) | 1.1.1.1.35 Vehicle 1.1.1.1.36 (N = 21) |
| Pre-CAC | | | | |
| N | 20 | 20 | 19 | 19 |
| mean (SD) | 0.84 (0.327) | 0.93 (0.354) | 0.91 (0.303) | 1.03 (0.343) |
| 7 min post-CAC | | | | |
| N | 20 | 19 | 18 | 18 |
| mean (SD) | 1.56 (0.451) | 1.78 (0.478) | 1.83 (0.485) | 2.01 (0.348) |
| P value[1] | — | 0.1596 | 0.0843 | 0.0014 |
| P value[2] | — | 0.1326 | 0.0627 | 0.0023 |
| 15 min post CAC | | | | |
| N | 20 | 19 | 18 | 18 |
| mean (SD) | 1.68 (0.507) | 1.84 (0.410) | 1.97 (0.484) | 2.15 (0.322) |
| P value[1] | — | 0.2642 | 0.0730 | 0.0014 |
| P value[2] | — | 0.2680 | 0.0542 | 0.0024 |
| 20 min post-CAC | | | | |
| N | 20 | 19 | 18 | 18 |
| mean (SD) | 1.66 (0.424) | 1.88 (0.567) | 1.81 (0.511) | 2.04 (0.386) |
| P value[1] | — | 0.1827 | 0.3574 | 0.0065 |
| P value[2] | — | 0.0793 | 0.2251 | 0.0053 |
| ANCOVA | | | | |
| LS mean | 1.63 | 1.82 | 1.83 | 2.03 |
| 95% CI | (1.45, 1.82) | (1.63, 2.01) | (1.64, 2.03) | (1.84, 2.23) |

TABLE 23-continued

Conjunctival Redness, Visit 4A, 16-hr Duration of Action, ITT Population with LOCF

| Time Point | 1.1.1.1.33 Combo (N = 21) | 1.1.1.1.34 Cetirizine 0.1% (N = 21) | Fluticasone 0.005% (N = 20) | 1.1.1.1.35 Vehicle 1.1.1.1.36 (N = 21) |
|---|---|---|---|---|
| TRT difference[3] | — | −0.19 | −0.20 | −0.40 |
| P value[4] | — | 0.1742 | 0.1441 | 0.0045 |

[1]P value calculated using a two-sample t-test to compare Combo to Vehicle and to the individual components.
[2]P value calculated using a Wilcoxon rank sum test to compare Combo to Vehicle and to the individual components.
[3]TRT difference: difference in the LS means (Combo LS mean − vehicle LS mean or component LS mean).
[4]P value from the ANCOVA analysis, with treatment and baseline score (Visit 4A pre-CAC) as covariates, comparing Combo to vehicle and to its individual components.
Source Table 14.2.2.1

TABLE 24

Conjunctival Redness, Visit 4A, 16-hr Duration of Action, PP Population

| Time Point | 1.1.1.1.37 Combo (N = 21) | 1.1.1.1.38 Cetirizine 0.1% (N = 21) | Fluticasone 0.005% (N = 20) | 1.1.1.1.39 Vehicle 1.1.1.1.40 (N = 21) |
|---|---|---|---|---|
| Pre-CAC | | | | |
| N | 18 | 17 | 17 | 17 |
| mean (SD) | 0.83 (0.343) | 0.93 (0.383) | 0.90 (0.319) | 1.01 (0.359) |
| 7 min post-CAC | | | | |
| N | 18 | 17 | 17 | 17 |
| mean (SD) | 1.50 (0.429) | 1.82 (0.482) | 1.81 (0.488) | 2.00 (0.354) |
| P value[1] | — | 0.0443 | 0.0560 | 0.0007 |
| P value[2] | — | 0.0263 | 0.0385 | 0.0009 |
| 15 min post CAC | | | | |
| N | 18 | 17 | 17 | 17 |
| mean (SD) | 1.61 (0.487) | 1.90 (0.396) | 1.94 (0.504) | 2.15 (0.331) |
| P value[1] | — | 0.0649 | 0.0575 | 0.0006 |
| P value[2] | — | 0.0581 | 0.0413 | 0.0011 |
| 20 min post-CAC | | | | |
| N | 18 | 17 | 17 | 17 |
| mean (SD) | 1.60 (0.385) | 1.97 (0.514) | 1.79 (0.525) | 2.03 (0.394) |
| P value[1] | — | 0.0219 | 0.2176 | 0.0025 |
| P value[2] | — | 0.0079 | 0.1283 | 0.0025 |
| ANCOVA | | | | |
| LS mean | 1.57 | 1.88 | 1.82 | 2.02 |
| 95% CI | (1.38, 1.76) | (1.69, 2.08) | (1.62, 2.01) | (1.83, 2.22) |
| TRT difference[3] | — | −0.32 | −0.25 | −0.46 |
| P value[4] | — | 0.0278 | 0.0765 | 0.0016 |

[1]P value calculated using a two-sample t-test to compare Combo to Vehicle and to the individual components.
[2]P value calculated using a Wilcoxon rank sum test to compare Combo to Vehicle and to the individual components.
[3]TRT difference: difference in the LS means (Combo LS mean − vehicle LS mean or component LS mean).
[4]P value from the ANCOVA analysis, with treatment and baseline score (Visit 3 pre-CAC) as covariates, comparing Combo to vehicle and to its individual components.
Source Table 14.2.2.3

TABLE 25

Conjunctival Redness, Visit 4B, 8-hour Rechallenge, ITT Population with LOCF

| Time Point | 1.1.1.1.41 Combo (N = 21) | 1.1.1.1.42 Cetirizine 0.1% (N = 21) | Fluticasone 0.005% (N = 20) | 1.1.1.1.43 Vehicle 1.1.1.1.44 (N = 21) |
|---|---|---|---|---|
| Pre-CAC | | | | |
| N | 20 | 20 | 19 | 19 |
| mean (SD) | 0.71 (0.424) | 0.96 (0.454) | 0.88 (0.268) | 1.21 (0.292) |

TABLE 25-continued

Conjunctival Redness, Visit 4B, 8-hour Rechallenge, ITT Population with LOCF

| | Group | | | |
|---|---|---|---|---|
| Time Point | 1.1.1.1.41 Combo (N = 21) | 1.1.1.1.42 Cetirizine 0.1% (N = 21) | Fluticasone 0.005% (N = 20) | 1.1.1.1.43 Vehicle 1.1.1.1.44 (N = 21) |
| 7 min post-CAC | | | | |
| N | 20 | 19 | 18 | 18 |
| mean (SD) | 1.39 (0.610) | 1.66 (0.560) | 1.81 (0.442) | 1.96 (0.346) |
| P value[1] | — | 0.1574 | 0.0201 | 0.0011 |
| P value[2] | — | 0.1493 | 0.0299 | 0.0042 |
| 15 min post CAC | | | | |
| N | 20 | 19 | 18 | 18 |
| mean (SD) | 1.39 (0.626) | 1.70 (0.518) | 1.85 (0.557) | 2.14 (0.366) |
| P value[1] | — | 0.0998 | 0.0218 | 0.0001 |
| P value[2] | — | 0.0924 | 0.0264 | 0.0004 |
| 20 min post-CAC | | | | |
| N | 20 | 19 | 18 | 18 |
| mean (SD) | 1.44 (0.617) | 1.70 (0.581) | 1.81 (0.546) | 2.14 (0.395) |
| P value[1] | — | 0.1837 | 0.0589 | 0.0002 |
| P value[2] | — | 0.1524 | 0.0514 | 0.0006 |
| ANCOVA | | | | |
| LS mean | 1.44 | 1.66 | 1.81 | 2.04 |
| 95% CI | (1.21, 1.66) | (1.43, 1.89) | (1.58, 2.04) | (1.81, 2.28) |
| TRT difference[3] | — | −0.22 | −0.37 | −0.61 |
| P value[4] | — | 0.1659 | 0.0230 | 0.0003 |

[1]P value calculated using a two-sample t-test to compare Combo to Vehicle and to the individual components.
[2]P value calculated using a Wilcoxon rank sum test to compare Combo to Vehicle and to the individual components.
[3]TRT difference: difference in the LS means (Combo LS mean − vehicle LS mean or component LS mean).
[4]P value from the ANCOVA analysis, with treatment and baseline score (Visit 4A pre-CAC) as covariates, comparing Combo to vehicle and to its individual components.
Source Table 14.2.2.1

TABLE 26

Conjunctival Redness, Visit 4B, 8-hr Rechallenge, PP Population

| | Group | | | |
|---|---|---|---|---|
| Time Point | 1.1.1.1.45 Combo (N = 21) | 1.1.1.1.46 Cetirizine 0.1% (N = 21) | Fluticasone 0.005% (N = 20) | 1.1.1.1.47 Vehicle 1.1.1.1.48 (N = 21) |
| Pre-CAC | | | | |
| N | 18 | 17 | 17 | 17 |
| mean (SD) | 0.69 (0.442) | 0.99 (0.488) | 0.87 (0.281) | 1.22 (0.305) |
| 7 min post-CAC | | | | |
| N | 18 | 17 | 17 | 17 |
| mean (SD) | 1.31 (0.585) | 1.72 (0.558) | 1.78 (0.441) | 1.94 (0.348) |
| P value[1] | — | 0.0392 | 0.0107 | 0.0005 |
| P value[2] | — | 0.0376 | 0.0128 | 0.0013 |
| 15 min post CAC | | | | |
| N | 18 | 17 | 17 | 17 |
| mean (SD) | 1.29 (0.577) | 1.76 (0.504) | 1.82 (0.564) | 2.13 (0.376) |
| P value[1] | — | 0.0143 | 0.0094 | <0.0001 |
| P value[2] | — | 0.0144 | 0.0116 | 0.0001 |
| 20 min post-CAC | | | | |
| N | 18 | 17 | 17 | 17 |
| mean (SD) | 1.35 (0.576) | 1.78 (0.551) | 1.79 (0.561) | 2.13 (0.406) |
| P value[1] | — | 0.0300 | 0.0263 | 0.0001 |
| P value[2] | — | 0.0230 | 0.0229 | 0.0002 |
| ANCOVA | | | | |
| LS mean | 1.35 | 1.73 | 1.79 | 2.04 |
| 95% CI | (1.12, 1.58) | (1.49, 1.96) | (1.56, 2.03) | (1.80, 2.27) |

TABLE 26-continued

Conjunctival Redness, Visit 4B, 8-hr Rechallenge, PP Population

| Time Point | Group | | | |
|---|---|---|---|---|
| | 1.1.1.1.45 Combo (N = 21) | 1.1.1.1.46 Cetirizine 0.1% (N = 21) | Fluticasone 0.005% (N = 20) | 1.1.1.1.47 Vehicle 1.1.1.1.48 (N = 21) |
| TRT difference[3] | — | −0.37 | −0.44 | −0.69 |
| P value[4] | — | 0.0272 | 0.0086 | 0.0001 |

[1] P value calculated using a two-sample t-test to compare Combo to Vehicle and to the individual components.
[2] P value calculated using a Wilcoxon rank sum test to compare Combo to Vehicle and to the individual components.
[3] TRT difference: difference in the LS means (Combo LS mean − vehicle LS mean or component LS mean).
[4] P value from the ANCOVA analysis, with treatment and baseline score (Visit 3 pre-CAC) as covariates, comparing Combo to vehicle and to its individual components.
Source Table 14.2.2.3

TABLE 27

Lid Swelling, Visit 3, 15-min Onset of Action PP Population

| Time Point | Group | | | |
|---|---|---|---|---|
| | 1.1.1.1.49 Combo (N = 21) | 1.1.1.1.50 Cetirizine 0.1% (N = 21) | Fluticasone 0.005% (N = 20) | 1.1.1.1.51 Vehicle 1.1.1.1.52 (N = 21) |
| Pre-CAC | | | | |
| N | 18 | 17 | 17 | 17 |
| mean (SD) | 0.1 (0.24) | 0.0 (0.00) | 0.1 (0.24) | 0.1 (0.33) |
| 7 min post-CAC | | | | |
| N | 18 | 17 | 17 | 17 |
| mean (SD) | 0.2 (0.43) | 0.5 (0.50) | 1.2 (0.88) | 1.4 (0.63) |
| P value[1] | — | 0.0879 | 0.0005 | <0.0001 |
| P value[2] | — | 0.0817 | 0.0006 | <0.0001 |
| 15 min post CAC | | | | |
| N | 18 | 17 | 17 | 17 |
| mean (SD) | 0.4 (0.61) | 0.7 (0.75) | 1.1 (0.97) | 1.5 (0.74) |
| P value[1] | — | 0.1456 | 0.0174 | <0.0001 |
| P value[2] | — | 0.1419 | 0.0178 | 0.0002 |
| 20 min post-CAC | | | | |
| N | 18 | 17 | 17 | 17 |
| mean (SD) | 0.4 (0.62) | 0.9 (0.75) | 1.1 (0.86) | 1.5 (0.85) |
| P value[1] | — | 0.0543 | 0.0128 | 0.0002 |
| P value[2] | — | 0.0579 | 0.0145 | 0.0004 |
| ANCOVA | | | | |
| LS mean | 0.3 | 0.7 | 1.1 | 1.4 |
| 95% CI | (0.0, 0.6) | (0.4, 1.0) | (0.8, 1.5) | (1.1, 1.7) |
| TRT difference[3] | — | −0.4 | −0.8 | −1.1 |
| P value[4] | — | 0.0916 | 0.0006 | <0.0001 |

[1] P value calculated using a two-sample t-test to compare Combo to Vehicle and to the individual components.
[2] P value calculated using a Wilcoxon rank sum test to compare Combo to Vehicle and to the individual components.
[3] TRT difference: difference in the LS means (Combo LS mean − vehicle LS mean or component LS mean).
[4] P value from the ANCOVA analysis, with treatment and baseline score (Visit 4A pre-CAC) as covariates, comparing Combo to vehicle and to its individual components.
Source Table 14.2.6.2

TABLE 28

Lid Swelling, Visit 4A, 16-hr Duration of Action, PP Population

| Time Point | Group | | | |
|---|---|---|---|---|
| | 1.1.1.1.53 Combo (N = 21) | 1.1.1.1.54 Cetirizine 0.1% (N = 21) | Fluticasone 0.005% (N = 20) | 1.1.1.1.55 Vehicle 1.1.1.1.56 (N = 21) |
| Pre-CAC | | | | |
| N | 18 | 17 | 17 | 17 |
| mean (SD) | 0.3 (0.59) | 0.2 (0.35) | 0.2 (0.40) | 0.5 (0.62) |

TABLE 28-continued

Lid Swelling, Visit 4A, 16-hr Duration of Action, PP Population

| Time Point | Group | | | |
|---|---|---|---|---|
| | 1.1.1.1.53 Combo (N = 21) | 1.1.1.1.54 Cetirizine 0.1% (N = 21) | Fluticasone 0.005% (N = 20) | 1.1.1.1.55 Vehicle 1.1.1.1.56 (N = 21) |
| 7 min post-CAC | | | | |
| N | 18 | 17 | 17 | 17 |
| mean (SD) | 0.6 (0.51) | 1.2 (0.95) | 1.1 (0.86) | 1.5 (0.66) |
| P value[1] | — | 0.0252 | 0.0274 | 0.0001 |
| P value[2] | — | 0.0399 | 0.0398 | 0.0002 |
| 15 min post CAC | | | | |
| N | 18 | 17 | 17 | 17 |
| mean (SD) | 0.7 (0.59) | 1.3 (1.00) | 1.1 (0.86) | 1.6 (0.70) |
| P value[1] | — | 0.0340 | 0.0827 | 0.0001 |
| P value[2] | — | 0.0548 | 0.1071 | 0.0003 |
| 20 min post-CAC | | | | |
| N | 18 | 17 | 17 | 17 |
| mean (SD) | 0.7 (0.59) | 1.3 (0.92) | 1.2 (0.95) | 1.7 (0.68) |
| P value[1] | — | 0.0314 | 0.0564 | 0.0001 |
| P value[2] | — | 0.0396 | 0.0740 | 0.0002 |
| ANCOVA | | | | |
| LS mean | 0.6 | 1.2 | 1.2 | 1.6 |
| 95% CI | (0.3, 1.0) | (0.9, 1.6) | (0.8, 1.5) | (1.2, 1.9) |
| TRT difference[3] | — | −0.6 | −0.5 | −1.0 |
| P value[4] | — | 0.0152 | 0.0298 | 0.0002 |

[1] P value calculated using a two-sample t-test to compare Combo to Vehicle and to the individual components.
[2] P value calculated using a Wilcoxon rank sum test to compare Combo to Vehicle and to the individual components.
[3] TRT difference: difference in the LS means (Combo LS mean − vehicle LS mean or component LS mean).
[4] P value from the ANCOVA analysis, with treatment and baseline score (Visit 4A pre-CAC) as covariates, comparing Combo to vehicle and to its individual components.
Source Table 14.2.6.2

TABLE 29

Lid Swelling, Visit 4B, 8-hour Rechallenge, PP Population

| Time Point | Group | | | |
|---|---|---|---|---|
| | 1.1.1.1.57 Combo (N = 21) | 1.1.1.1.58 Cetirizine 0.1% (N = 21) | Fluticasone 0.005% (N = 20) | 1.1.1.1.59 Vehicle 1.1.1.1.60 (N = 21) |
| Pre-CAC | | | | |
| N | 18 | 17 | 17 | 17 |
| mean (SD) | 0.1 (0.32) | 0.3 (0.59) | 0.2 (0.53) | 0.4 (0.79) |
| 7 min post-CAC | | | | |
| N | 18 | 17 | 17 | 17 |
| mean (SD) | 0.4 (0.51) | 0.7 (0.58) | 1.1 (1.03) | 1.6 (0.93) |
| P value[1] | — | 0.2216 | 0.0183 | 0.0002 |
| P value[2] | — | 0.2575 | 0.0352 | 0.0003 |
| 15 min post CAC | | | | |
| N | 18 | 17 | 17 | 17 |
| mean (SD) | 0.5 (0.50) | 1.0 (0.76) | 1.1 (1.00) | 1.6 (0.70) |
| P value[1] | — | 0.0306 | 0.0194 | <0.0001 |
| P value[2] | — | 0.0421 | 0.0311 | 0.0001 |
| 20 min post-CAC | | | | |
| N | 18 | 17 | 17 | 17 |
| mean (SD) | 0.5 (0.50) | 1.0 (0.88) | 1.0 (0.94) | 1.6 (0.66) |
| P value[1] | — | 0.0407 | 0.0405 | <0.0001 |
| P value[2] | — | 0.0635 | 0.0683 | 0.0001 |
| ANCOVA | | | | |
| LS mean | 0.5 | 0.8 | 1.1 | 1.6 |
| 95% CI | (0.1, 0.8) | (0.5, 1.2) | (0.8, 1.4) | (1.2, 1.9) |

TABLE 29-continued

Lid Swelling, Visit 4B, 8-hour Rechallenge, PP Population

| Time Point | 1.1.1.1.57 Combo (N = 21) | 1.1.1.1.58 Cetirizine 0.1% (N = 21) | Fluticasone 0.005% (N = 20) | 1.1.1.1.59 Vehicle 1.1.1.1.60 (N = 21) |
|---|---|---|---|---|
| TRT difference[3] | — | −0.4 | −0.6 | −1.1 |
| P value[4] | — | 0.1269 | 0.0102 | <0.0001 |

[1]P value calculated using a two-sample t-test to compare Combo to Vehicle and to the individual components.
[2]P value calculated using a Wilcoxon rank sum test to compare Combo to Vehicle and to the individual components.
[3]TRT difference: difference in the LS means (Combo LS mean − vehicle LS mean or component LS mean).
[4]P value from the ANCOVA analysis, with treatment and baseline score (Visit 4A pre-CAC) as covariates, comparing Combo to vehicle and to its individual components.
Source Table 14.2.6.2

TABLE 30

Ciliary Redness, Visit 3, 15-min Onset of Action, PP Population

| Time Point | 1.1.1.1.61 Combo (N = 21) | 1.1.1.1.62 Cetirizine 0.1% (N = 21) | Fluticasone 0.005% (N = 20) | 1.1.1.1.63 Vehicle 1.1.1.1.64 (N = 21) |
|---|---|---|---|---|
| Pre-CAC | | | | |
| N | 18 | 17 | 17 | 17 |
| mean (SD) | 0.39 (0.335) | 0.59 (0.423) | 0.59 (0.374) | 0.51 (0.576) |
| 7 min post-CAC | | | | |
| N | 18 | 17 | 17 | 17 |
| mean (SD) | 1.44 (0.898) | 1.84 (0.852) | 2.35 (0.834) | 2.37 (0.857) |
| P value[1] | — | 0.1921 | 0.0039 | 0.0038 |
| P value[2] | — | 0.1313 | 0.0054 | 0.0065 |
| 15 min post CAC | | | | |
| N | 18 | 17 | 17 | 17 |
| mean (SD) | 1.89 (0.956) | 2.25 (0.940) | 2.47 (0.865) | 2.54 (0.880) |
| P value[1] | — | 0.2679 | 0.0677 | 0.0424 |
| P value[2] | — | 0.2962 | 0.0711 | 0.0484 |
| 20 min post-CAC | | | | |
| N | 18 | 17 | 17 | 17 |
| mean (SD) | 1.94 (1.100) | 2.29 (0.953) | 2.51 (0.946) | 2.56 (0.788) |
| P value[1] | — | 0.3214 | 0.1090 | 0.0658 |
| P value[2] | — | 0.2817 | 0.1196 | 0.0738 |
| ANCOVA | | | | |
| LS mean | 1.77 | 2.04 | 2.40 | 2.47 |
| 95% CI | (1.36, 2.18) | (1.63, 2.46) | (1.99, 2.82) | (2.05, 2.88) |
| TRT difference[3] | — | −0.27 | −0.63 | −0.70 |
| P value[4] | — | 0.3558 | 0.0348 | 0.0189 |

[1]P value calculated using a two-sample t-test to compare Combo to Vehicle and to the individual components.
[2]P value calculated using a Wilcoxon rank sum test to compare Combo to Vehicle and to the individual components.
[3]TRT difference: difference in the LS means (Combo LS mean − vehicle LS mean or component LS mean).
[4]P value from the ANCOVA analysis, with treatment and baseline score (Visit 3 pre-CAC) as covariates, comparing Combo to vehicle and to its individual components.
Source Table 14.2.3.2

TABLE 31

Ciliary Redness, Visit 4A, 16-hr Duration of Action, PP Population

| Time Point | 1.1.1.1.65 Combo (N = 21) | 1.1.1.1.66 Cetirizine 0.1% (N = 21) | Fluticasone 0.005% (N = 20) | 1.1.1.1.67 Vehicle 1.1.1.1.68 (N = 21) |
|---|---|---|---|---|
| Pre-CAC | | | | |
| N | 18 | 17 | 17 | 17 |
| mean (SD) | 0.56 (0.359) | 0.75 (0.451) | 0.63 (0.344) | 0.79 (0.532) |

TABLE 31-continued

Ciliary Redness, Visit 4A, 16-hr Duration of Action, PP Population

| Time Point | 1.1.1.1.65 Combo (N = 21) | 1.1.1.1.66 Cetirizine 0.1% (N = 21) | Fluticasone 0.005% (N = 20) | 1.1.1.1.67 Vehicle 1.1.1.1.68 (N = 21) |
|---|---|---|---|---|
| 7 min post-CAC | | | | |
| N | 18 | 17 | 17 | 17 |
| mean (SD) | 1.38 (0.577) | 1.81 (0.616) | 1.71 (0.626) | 2.03 (0.499) |
| P value[1] | — | 0.0393 | 0.1143 | 0.0011 |
| P value[2] | — | 0.0499 | 0.0893 | 0.0026 |
| 15 min post CAC | | | | |
| N | 18 | 17 | 17 | 17 |
| mean (SD) | 1.51 (0.578) | 1.90 (0.600) | 1.84 (0.712) | 2.10 (0.434) |
| P value[1] | — | 0.0633 | 0.1506 | 0.0017 |
| P value[2] | — | 0.0494 | 0.0731 | 0.0018 |
| 20 min post-CAC | | | | |
| N | 18 | 17 | 17 | 17 |
| mean (SD) | 1.53 (0.629) | 1.91 (0.637) | 1.72 (0.667) | 2.04 (0.461) |
| P value[1] | — | 0.0823 | 0.3860 | 0.0092 |
| P value[2] | — | 0.0889 | 0.3558 | 0.0122 |
| ANCOVA | | | | |
| LS mean | 1.48 | 1.85 | 1.71 | 2.04 |
| 95% CI | (1.21, 1.74) | (1.58, 2.12) | (1.44, 1.98) | (1.77, 2.31) |
| TRT difference[3] | — | −0.38 | −0.23 | −0.57 |
| P value[4] | — | 0.0551 | 0.2294 | 0.0043 |

[1] P value calculated using a two-sample t-test to compare Combo to Vehicle and to the individual components.
[2] P value calculated using a Wilcoxon rank sum test to compare Combo to Vehicle and to the individual components.
[3] TRT difference: difference in the LS means (Combo LS mean − vehicle LS mean or component LS mean).
[4] P value from the ANCOVA analysis, with treatment and baseline score (Visit 3 pre-CAC) as covariates, comparing Combo to vehicle and to its individual components.
Source Table 14.2.3.2

TABLE 32

Ciliary Redness, Visit 4B, 8-hour Rechallenge, PP Population

| Time Point | 1.1.1.1.69 Combo (N = 21) | 1.1.1.1.70 Cetirizine 0.1% (N = 21) | Fluticasone 0.005% (N = 20) | 1.1.1.1.71 Vehicle 1.1.1.1.72 (N = 21) |
|---|---|---|---|---|
| Pre-CAC | | | | |
| N | 18 | 17 | 17 | 17 |
| mean (SD) | 0.57 (0.444) | 0.79 (0.478) | 0.53 (0.341) | 0.97 (0.413) |
| 7 min post-CAC | | | | |
| N | 18 | 17 | 17 | 17 |
| mean (SD) | 1.04 (0.759) | 1.65 (0.673) | 1.68 (0.557) | 2.01 (0.437) |
| P value[1] | — | 0.0176 | 0.0080 | 0.0001 |
| P value[2] | — | 0.0177 | 0.0107 | 0.0003 |
| 15 min post CAC | | | | |
| N | 18 | 17 | 17 | 17 |
| mean (SD) | 1.08 (0.702) | 1.69 (0.693) | 1.74 (0.603) | 2.18 (0.393) |
| P value[1] | — | 0.0146 | 0.0058 | <0.0001 |
| P value[2] | — | 0.0158 | 0.0061 | 0.0001 |
| 20 min post-CAC | | | | |
| N | 18 | 17 | 17 | 17 |
| mean (SD) | 1.15 (0.713) | 1.63 (0.650) | 1.68 (0.717) | 2.10 (0.566) |
| P value[1] | — | 0.0453 | 0.0377 | 0.0001 |
| P value[2] | — | 0.0487 | 0.0463 | 0.0004 |
| ANCOVA | | | | |
| LS mean | 1.11 | 1.63 | 1.67 | 2.06 |
| 95% CI | (0.82, 1.41) | (1.34, 1.93) | (1.37, 1.97) | (1.77, 2.36) |

TABLE 32-continued

Ciliary Redness, Visit 4B, 8-hour Rechallenge, PP Population

| Time Point | 1.1.1.1.69 Combo (N = 21) | 1.1.1.1.70 Cetirizine 0.1% (N = 21) | Fluticasone 0.005% (N = 20) | 1.1.1.1.71 Vehicle 1.1.1.1.72 (N = 21) |
|---|---|---|---|---|
| TRT difference[3] | — | −0.52 | −0.56 | −0.95 |
| P value[4] | — | 0.0161 | 0.0101 | <0.0001 |

[1]P value calculated using a two-sample t-test to compare Combo to Vehicle and to the individual components.
[2]P value calculated using a Wilcoxon rank sum test to compare Combo to Vehicle and to the individual components.
[3]TRT difference: difference in the LS means (Combo LS mean − vehicle LS mean or component LS mean).
[4]P value from the ANCOVA analysis, with treatment and baseline score (Visit 3 pre-CAC) as covariates, comparing Combo to vehicle and to its individual components.
Source Table 14.2.3.2

TABLE 33

Ear or Palate Pruritis, Visit 3, 15-min Onset of Action, PP Population

| Time Point | 1.1.1.1.73 Combo (N = 21) | 1.1.1.1.74 Cetirizine 0.1% (N = 21) | Fluticasone 0.005% (N = 20) | 1.1.1.1.75 Vehicle 1.1.1.1.76 (N = 21) |
|---|---|---|---|---|
| Pre-CAC | | | | |
| N | 18 | 17 | 17 | 17 |
| mean (SD) | 0.1 (0.24) | 0.3 (0.59) | 0.2 (0.53) | 0.0 (0.00) |
| 7 min post-CAC | | | | |
| N | 18 | 17 | 17 | 17 |
| mean (SD) | 0.4 (0.78) | 0.3 (0.59) | 0.5 (0.94) | 1.2 (1.39) |
| P value[1] | — | 0.6859 | 0.6350 | 0.0372 |
| P value[2] | — | 0.7953 | 0.8031 | 0.0613 |
| 15 min post CAC | | | | |
| N | 18 | 17 | 17 | 17 |
| mean (SD) | 0.4 (0.85) | 0.6 (0.93) | 0.7 (1.10) | 1.4 (1.33) |
| P value[1] | — | 0.3988 | 0.3509 | 0.0118 |
| P value[2] | — | 0.2771 | 0.3726 | 0.0101 |
| 20 min post-CAC | | | | |
| N | 18 | 17 | 17 | 17 |
| mean (SD) | 0.6 (1.04) | 0.8 (0.90) | 1.0 (1.27) | 1.5 (1.42) |
| P value[1] | — | 0.6429 | 0.3314 | 0.0379 |
| P value[2] | — | 0.3846 | 0.3593 | 0.0283 |
| ANCOVA | | | | |
| LS mean | 0.6 | 0.4 | 0.7 | 1.5 |
| 95% CI | (0.1, 1.0) | (−0.1, 0.8) | (0.3, 1.2) | (1.1, 2.0) |
| TRT difference[3] | — | 0.2 | −0.2 | −0.9 |
| P value[4] | — | 0.5701 | 0.6294 | 0.0034 |

[1]P value calculated using a two-sample t-test to compare Combo to Vehicle and to the individual components.
[2]P value calculated using a Wilcoxon rank sum test to compare Combo to Vehicle and to the individual components.
[3]TRT difference: difference in the LS means (Combo LS mean − vehicle LS mean or component LS mean).
[4]P value from the ANCOVA analysis, with treatment and baseline score (Visit 4A pre-CAC) as covariates, comparing Combo to vehicle and to its individual components.
Source Table 14.2.10.2

TABLE 34

Ear or Palate Pruritis, Visit 4A, 16-hr Duration of Action, PP Population

| Time Point | 1.1.1.1.77 Combo (N = 21) | 1.1.1.1.78 Cetirizine 0.1% (N = 21) | Fluticasone 0.005% (N = 20) | 1.1.1.1.79 Vehicle 1.1.1.1.80 (N = 21) |
|---|---|---|---|---|
| Pre-CAC | | | | |
| N | 18 | 17 | 17 | 17 |
| mean (SD) | 0.2 (0.73) | 0.2 (0.56) | 0.1 (0.24) | 0.4 (0.61) |

TABLE 34-continued

Ear or Palate Pruritis, Visit 4A, 16-hr Duration of Action, PP Population

| Time Point | Group | | | |
|---|---|---|---|---|
| | 1.1.1.1.77 Combo (N = 21) | 1.1.1.1.78 Cetirizine 0.1% (N = 21) | Fluticasone 0.005% (N = 20) | 1.1.1.1.79 Vehicle 1.1.1.1.80 (N = 21) |
| 7 min post-CAC | | | | |
| N | 18 | 17 | 17 | 17 |
| mean (SD) | 0.4 (0.85) | 0.4 (0.62) | 0.4 (0.87) | 1.5 (1.33) |
| P value[1] | — | 0.9277 | 0.9378 | 0.0057 |
| P value[2] | — | 0.5321 | 0.9463 | 0.0023 |
| 15 min post CAC | | | | |
| N | 18 | 17 | 17 | 17 |
| mean (SD) | 0.7 (1.13) | 1.3 (0.99) | 0.6 (1.11) | 1.5 (1.37) |
| P value[1] | — | 0.1191 | 0.8441 | 0.0677 |
| P value[2] | — | 0.0930 | 0.9377 | 0.0458 |
| 20 min post-CAC | | | | |
| N | 18 | 17 | 17 | 17 |
| mean (SD) | 0.7 (1.08) | 1.2 (1.03) | 0.9 (1.43) | 1.5 (1.23) |
| P value[1] | — | 0.1216 | 0.5298 | 0.0355 |
| P value[2] | — | 0.0737 | 0.6064 | 0.0240 |
| ANCOVA | | | | |
| LS mean | 0.6 | 0.7 | 0.6 | 1.6 |
| 95% CI | (0.2, 1.1) | (0.3, 1.2) | (0.2, 1.1) | (1.2, 2.1) |
| TRT difference[3] | — | −0.1 | 0.0 | −1.0 |
| P value[4] | — | 0.7055 | 0.9348 | 0.0024 |

[1]P value calculated using a two-sample t-test to compare Combo to Vehicle and to the individual components.
[2]P value calculated using a Wilcoxon rank sum test to compare Combo to Vehicle and to the individual components.
[3]TRT difference: difference in the LS means (Combo LS mean − vehicle LS mean or component LS mean).
[4]P value from the ANCOVA analysis, with treatment and baseline score (Visit 4A pre-CAC) as covariates, comparing Combo to vehicle and to its individual components.
Source Table 14.2.10.2

TABLE 35

Ear or Palate Pruritis, Visit 4B, 8-hour Rechallenge, PP Population

| Time Point | Group | | | |
|---|---|---|---|---|
| | 1.1.1.1.81 Combo (N = 21) | 1.1.1.1.82 Cetirizine 0.1% (N = 21) | Fluticasone 0.005% (N = 20) | 1.1.1.1.83 Vehicle 1.1.1.1.84 (N = 21) |
| Pre-CAC | | | | |
| N | 18 | 17 | 17 | 17 |
| mean (SD) | 0.2 (0.65) | 0.2 (0.56) | 0.2 (0.73) | 0.3 (0.47) |
| 7 min post-CAC | | | | |
| N | 18 | 17 | 17 | 17 |
| mean (SD) | 0.3 (0.69) | 0.7 (0.85) | 0.6 (1.06) | 1.2 (1.24) |
| P value[1] | — | 0.1648 | 0.4099 | 0.0206 |
| P value[2] | — | 0.1409 | 0.4419 | 0.0213 |
| 15 min post CAC | | | | |
| N | 18 | 17 | 17 | 17 |
| mean (SD) | 0.4 (0.78) | 1.1 (1.05) | 0.8 (1.24) | 1.2 (1.15) |
| P value[1] | — | 0.0412 | 0.2915 | 0.0250 |
| P value[2] | — | 0.0366 | 0.3785 | 0.0256 |
| 20 min post-CAC | | | | |
| N | 18 | 17 | 17 | 17 |
| mean (SD) | 0.5 (0.86) | 1.2 (1.01) | 0.8 (1.20) | 1.3 (1.16) |
| P value[1] | — | 0.0416 | 0.4612 | 0.0292 |
| P value[2] | — | 0.0227 | 0.4933 | 0.0246 |
| ANCOVA | | | | |
| LS mean | 0.5 | 0.8 | 0.6 | 1.4 |
| 95% CI | (0.1, 0.9) | (0.4, 1.2) | (0.2, 1.1) | (0.9, 1.8) |

TABLE 35-continued

Ear or Palate Pruritis, Visit 4B, 8-hour Rechallenge, PP Population

| Time Point | 1.1.1.1.81 Combo (N = 21) | 1.1.1.1.82 Cetirizine 0.1% (N = 21) | Fluticasone 0.005% (N = 20) | 1.1.1.1.83 Vehicle 1.1.1.1.84 (N = 21) |
|---|---|---|---|---|
| TRT difference[3] | — | −0.3 | −0.2 | −0.9 |
| P value[4] | — | 0.2954 | 0.5919 | 0.0036 |

[1]P value calculated using a two-sample t-test to compare Combo to Vehicle and to the individual components.
[2]P value calculated using a Wilcoxon rank sum test to compare Combo to Vehicle and to the individual components.
[3]TRT difference: difference in the LS means (Combo LS mean − vehicle LS mean or component LS mean).
[4]P value from the ANCOVA analysis, with treatment and baseline score (Visit 4A pre-CAC) as covariates, comparing Combo to vehicle and to its individual components.
Source Table 14.2.10.2

Secondary Efficacy Endpoints (Diary Data)

During the 12 days between Visits 3 and 4A, subjects self-administered study medication QD and rated their ocular and nasal symptoms in the morning and in the evening using a 5-point scale (0 to 4, where 0=None/Absent; 1=Mild; 2=Moderate; 3=Severe; and 4=Very Severe). Table 36 shows an overview of the diary data analysis (ANCOVA). The numbers within cells in Table 36 represent the treatment difference calculated with the ANCOVA model, which included both morning and evening data from all 12 days of diary data.

Combo demonstrated significantly lower (P<0.05) scores than vehicle for ocular itching, lid swelling, tearing/watery eyes, nasal itching, nasal congestion, rhinorrhea, ear/palate itching, and total nasal symptom scores (TNSS).

Combo arm had lower scores than vehicle for ocular redness (statistical trend)

The ocular itching data from the diary scores, while not reaching the level of clinical efficacy, showed the same trend as was observed in the CAC data. The diary data represent subjects' response to environmental allergens and tend to validate the modified CAC model.

TABLE 36

Diary Data: Overall Results for all Treatments vs Vehicle

| Parameter | Combo | Cetirizine | Fluticasone |
|---|---|---|---|
| Ocular Redness | -0.30 | | |
| Ocular Itching | -0.50 | -0.50 | -0.40 |
| Lid Swelling | -0.40 | -0.30 | |
| Tearing/Watery Eye | -0.30 | -0.40 | -0.30 |
| Nasal Itching | -0.30 | -0.30 | -0.30 |
| Nasal Congestion | -0.40 | | -0.30 |
| Rhinorrhea | -0.30 | -0.20 | -0.40 |
| Ear/Palate Itching | -0.40 | | -0.20 |
| TNSS | -1.30 | -0.90 | -1.20 |

LEGEND
 P < 0.05
 0.05 < P < 0.10

Combo demonstrated clinical efficacy in the prevention of ciliary redness at Visit 4B. The mean ciliary redness scores for Combo were significantly lower (P<0.05) than vehicle at all 3 time points at Visit 4B. The treatment differences (Combo mean minus Vehicle mean) at Visit 4B were −0.97, −1.1, and −0.95 units at 7, 15, and 20 minutes post CAC, respectively. At Visit 3, 2 of 3 time points were significantly lower (P<0.05) than Vehicle. At Visit 4A, all 3 time points were significantly lower than Vehicle, but the magnitudes of the treatment differences were not greater than 1.0 unit at any of the 3 time points. See Tables 30-32 for the detailed ciliary redness data in the PP population at Visits 3, 4A, and 4B, respectively.

Combo demonstrated clinical efficacy in the prevention of ear/palate itching at Visit 4A. The mean ear/palate itching scores for Combo were significantly lower (P<0.05) than vehicle at all 3 time points at Visit 4A. The treatment differences (Combo mean minus Vehicle mean) at Visit 4A were −1.1, −0.8, and −0.8 units at 7, 15, and 20 minutes post CAC, respectively. The treatment difference from the ANCOVA model was −1.0 units. At Visits 3 and 4B, all 3 time points were significantly lower (P<0.05) than Vehicle. At Visits 3 and 4B, the magnitudes of the treatment differences were all greater than 0.5 units, but the majority were <1.0 unit. See Tables 33-35 for the detailed ear/palate itching data in the PP population at Visits 3, 4A, and 4B, respectively.

Combo demonstrated significant lower (P<0.05) scores for episcleral redness, tearing/watery eyes, rhinorrhea, and nasal congestion compared to Vehicle.

See Table 16 for the overview.

All efficacy analyses were performed on data collected at Visits 3, 4A, and 4B. Primary and secondary efficacy analyses were performed on both the ITT population and the PP population.

ITT population:

Eighty three (83) subjects were randomized at Visit 2B and comprised the ITT population. No subjects were excluded from the ITT population because of protocol violations. The ITT population was analyzed as randomized; all data were included. Missing data were imputed using the last observation carried forward method (LOCF) for the ITT population.

PP Population:

The PP population was a subset of the ITT population and consisted of subjects who completed all four visits with no major protocol violations. This population was analyzed as treated using observed data only and was used for confirmatory analyses. Fourteen (14) subjects in the ITT population were excluded from the PP population; 12 of these subjects did not complete the study. The reasons for discontinuation included: subject noncompliance (missed study visit, or did not return study drug or diary, n=9); tech error: subject given wrong drug (n=2), or subject should have screen failed at Visit 1 (n=1).

All safety analyses were performed on the safety population.

Safety Population:

The Safety population included all randomized subjects who received at least one dose of any investigational treatment. All 83 subjects randomized at Visit 2B also received their first dose of assigned study medication post CAC at Visit 2B, and thus comprise the Safety population. The Safety population was analyzed as treated; no data exclusion was allowed for any reason.

Conclusion

The low dose combination of 0.1% Cetirizine/0.005% Fluticasone was the most effective at preventing signs of allergic conjunctivitis in the human modified conjunctival allergen challenge (CAC) compared to components of the combination used alone at the same concentration.

The data described herein demonstrate clinical and statistical superiority of the combination of 0.1% Cetirizine/0.005% Fluticasone. The combination had clinically and statistically significant lower itching scores and conjunctival redness scores than vehicle at all visits and timepoints. The combination was statistically superior to cetirizine in the prevention of conjunctival redness (Visit 4B at all timepoints). The combination was statistically superior to fluticasone in the prevention of ocular itching (Visit 3 and Visit 4B) and in the prevention of conjunctival redness (Visit 3 and Visit 4B)

The combination also had statistically significantly lower scores than vehicle for ocular itching, lid swelling, tearing/watery eyes, nasal itching, nasal congestion, rhinorrhea, ear/palate itching, and total nasal symptom scores surprisingly, even though the concentrations were much lower than that used for currently marketed nasal preparations of fluticasone Additionally, at 0.005% Fluticasone did not contribute to elevated intraocular pressure (IOP) as one may have expected from ocular administration of a steroid, yet a dose of the active ingredients was identified that was highly efficacious with only QD dosing.

Lastly, the low dose combination worked better than well known, leading ocular antihistamine and ocular steroid—these results confirm the effectiveness of the specific combination of cetirizine/fluticasone at the preferred low dose concentrations.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A topical ophthalmic formulation comprising 0.1% to 0.25% cetirizine (w/v), 0.005% to 0.01% fluticasone (w/v), 1% Polyethylene Glycol 400, NF, 0.2% Dibasic Sodium Phosphate, Anhydrous, USP, 0.25% Hypromellose, USP, 0.1% Polysorbate 80, NF, 1.8% Glycerin, USP, 0.025% Edetate Disodium, USP and 0.01% Benzalkonium Chloride, NF.

2. The formulation of claim 1, wherein the pH is about 5.0-8.0.

3. The formulation of claim 1, wherein the pH is 7.0.

4. A method of treating a sign or symptom of an ocular or nasal allergic disorder by topically administering to the eye of a subject in need of such treatment the ophthalmic formulation of claim 1.

5. The method of claim 4, wherein the allergic disorder is against an airborne allergen.

6. The method of claim 4, wherein the sign or symptom is selected from the group comprising, ocular itching, redness, lid swelling, chemosis, tearing rhinorrhea, sneezing, nasal congestion, nasal itching, itching of the palate, or itching of the ear itching, redness, lid swelling, chemosis, tearing rhinorrhea, sneezing, nasal congestion, nasal itching, itching of the palate, or itching of the ear.

7. The method of claim 4, wherein the allergic disorder is allergic conjunctivitis, allergic rhinoconjuntivitis or rhinitis.

8. A method for treating a sign or a symptom of allergic conjunctivitis by topically administering to the eye of a subject in need of such treatment the ophthalmic formulation of claim 1.

9. The method of claim 8, wherein said sign and symptom is selected from the group consisting of ocular itching, redness, lid swelling, chemosis or tearing.

10. A method for treating a sign or a symptom of allergic rhinoconjunctivitis by topically administering to the eye of a subject in need of such treatment the ophthalmic formulation of claim 1.

11. The method of claim 10, wherein said sign and symptom is selected from the group consisting of ocular itching, redness, lid swelling, chemosis, tearing, rhinorrhea, sneezing, nasal congestion, nasal itching, itching of the palate, or itching of the ear.

12. A method for treating a sign or a symptom of rhinitis by topically administering to the eye of a subject in need of such treatment the ophthalmic formulation of claim 1.

13. The method of claim 12, wherein said sign and symptom is selected from the group consisting of rhinorrhea, sneezing, nasal congestion, nasal itching, itching of the palate, or itching of the ear.

14. The method of claim of any one of claims 4 to 13, wherein the ophthalmic formulation is administered once daily.

* * * * *